US 10,648,044 B2
May 12, 2020

(12) United States Patent
Vervecken et al.

(54) METHODS AND MATERIALS FOR TREATMENT OF POMPE'S DISEASE

(71) Applicant: Oxyrane UK Limited, Manchester (GB)

(72) Inventors: Wouter Vervecken, Landskouter (BE); Kathleen Camilla Telesphore Alida Maria Piens, Ghent (BE); Jan Robert Ludo Stout, Asper-Gavere (BE); Gwenda Noëlla Pynaert, Aalter (BE)

(73) Assignee: Oxyrane UK Limited, Manchester (GB)

(*) Notice: Subject to any disclaimer, the term of this patent is extended or adjusted under 35 U.S.C. 154(b) by 0 days.

(21) Appl. No.: 14/981,123

(22) Filed: Dec. 28, 2015

(65) Prior Publication Data
US 2016/0279254 A1 Sep. 29, 2016

Related U.S. Application Data

(62) Division of application No. 13/831,368, filed on Mar. 14, 2013, now Pat. No. 9,249,399.

(60) Provisional application No. 61/611,485, filed on Mar. 15, 2012.

(51) Int. Cl.
*C12N 9/24* (2006.01)
*C12N 9/26* (2006.01)
*C12N 1/15* (2006.01)
*C12N 15/55* (2006.01)
*C12P 21/06* (2006.01)
*C12P 21/02* (2006.01)
*A61K 38/47* (2006.01)
*C12N 9/62* (2006.01)
*A61K 38/43* (2006.01)
*C12N 9/44* (2006.01)
*A61K 47/64* (2017.01)
*C07K 14/65* (2006.01)
*A61K 38/00* (2006.01)

(52) U.S. Cl.
CPC ...... *C12Y 302/01003* (2013.01); *A61K 38/43* (2013.01); *A61K 38/47* (2013.01); *A61K 47/64* (2017.08); *C12N 9/2408* (2013.01); *C12N 9/2451* (2013.01); *C12N 9/62* (2013.01); *C12P 21/02* (2013.01); *C12P 21/06* (2013.01); *C12Y 302/0102* (2013.01); *A61K 38/00* (2013.01); *C07K 14/65* (2013.01); *C07K 2319/70* (2013.01)

(58) Field of Classification Search
None
See application file for complete search history.

(56) References Cited

U.S. PATENT DOCUMENTS

| | | |
|---|---|---|
| 4,307,717 A | 12/1981 | Hymes et al. |
| 4,352,883 A | 10/1982 | Lim |
| 4,353,888 A | 10/1982 | Sefton |
| 4,407,957 A | 10/1983 | Lim |
| 4,704,362 A | 11/1987 | Itakura et al. |
| 4,837,148 A | 6/1989 | Cregg |
| 4,879,231 A | 11/1989 | Stroman et al. |
| 4,882,279 A | 11/1989 | Cregg |
| 4,883,666 A | 11/1989 | Sabel et al. |
| 4,929,555 A | 5/1990 | Cregg et al. |
| 4,968,733 A | 11/1990 | Miller et al. |
| 4,976,859 A | 12/1990 | Wechs |
| 5,084,350 A | 1/1992 | Chang et al. |
| 5,158,881 A | 10/1992 | Aebischer et al. |
| 5,272,070 A | 12/1993 | Lehrman et al. |
| 5,284,761 A | 2/1994 | Aebischer et al. |
| 5,585,089 A | 12/1996 | Queen et al. |
| 5,798,113 A | 8/1998 | Dionne et al. |
| 5,800,828 A | 9/1998 | Dionne et al. |
| 6,110,703 A | 8/2000 | Egel et al. |
| 6,265,185 B1 | 7/2001 | Muller et al. |
| 6,699,658 B1 | 3/2004 | Wittrup et al. |
| 6,803,225 B2 | 10/2004 | Contreras et al. |
| 6,872,392 B2 | 3/2005 | Nakamura et al. |
| 7,029,872 B2 | 4/2006 | Gerngross |
| 7,259,007 B2 | 8/2007 | Bobrowicz et al. |
| 7,262,287 B2 | 8/2007 | Kang et al. |
| 7,326,681 B2 | 2/2008 | Gerngross |
| 7,390,884 B2 | 6/2008 | Segal et al. |
| 7,422,742 B2 | 9/2008 | Greenfeder et al. |
| 7,422,890 B2 | 9/2008 | Gopalakrishnakone et al. |
| 7,431,927 B2 | 10/2008 | Couto et al. |
| 7,442,772 B2 | 10/2008 | Goddard et al. |
| 7,449,308 B2 | 11/2008 | Gerngross et al. |

(Continued)

FOREIGN PATENT DOCUMENTS

| | | |
|---|---|---|
| AU | 2012206984 | 8/2012 |
| EP | 1408117 | 4/2004 |

(Continued)

OTHER PUBLICATIONS

Prince et al., Lipoprotein Receptor Binding, Cellular Uptake, and Lysosomal Delivery of Fusions between the Receptor-associated Protein (RAP) and alpha-L-Iduronidase or Acid alpha-Glucosidase, J. Biol. Chem., 2004, 279, 35037-46.*

Zhu et al., Carbohydrate-remodeled acid α-glucosidase with higher affinity for the cation-independent mannose 6-phosphate receptor demonstrates improved delivery to muscles of Pompe mice, Biochem. J., 2005, 389, 619-28.*

Zhu et al., Conjugation of Mannose 6-Phosphate-containing Oligosaccharides to Acid α-Glucosidase Improves the Clearance of Glycogen in Pompe Mice, J. Biol. Chem., 2004, 279, 50336-41.*

(Continued)

*Primary Examiner* — Robert B Mondesi
*Assistant Examiner* — Todd M Epstein
(74) *Attorney, Agent, or Firm* — Fish & Richardson P.C.

(57) ABSTRACT

This document relates to molecular complexes having acid alpha glucosidase activity and at least one modification that results in enhanced ability of the molecular complex to be transported to the interior of a mammalian cell.

10 Claims, 15 Drawing Sheets

Specification includes a Sequence Listing.

(56) References Cited

U.S. PATENT DOCUMENTS

| | | |
|---|---|---|
| 7,488,591 B2 | 2/2009 | Miura et al. |
| 7,785,856 B2 | 8/2010 | LeBowitz et al. |
| 8,026,083 B2 | 9/2011 | Callewaert et al. |
| 8,597,906 B2 | 12/2013 | Callewaert et al. |
| 9,206,408 B2 | 12/2015 | Callewaert et al. |
| 9,222,083 B2 | 12/2015 | Callewaert et al. |
| 9,249,399 B2 | 2/2016 | Vervecken et al. |
| 9,598,682 B2 | 3/2017 | Callewaert et al. |
| 9,689,015 B2 | 6/2017 | Piens et al. |
| 2002/0127219 A1 | 9/2002 | Okkels et al. |
| 2002/0137125 A1 | 9/2002 | Zhu |
| 2003/0147868 A1 | 8/2003 | Treco et al. |
| 2003/0186374 A1 | 10/2003 | Hufton et al. |
| 2004/0018588 A1 | 1/2004 | Contreras et al. |
| 2004/0018590 A1 | 1/2004 | Gerngross et al. |
| 2005/0014270 A1 | 1/2005 | Picataggio et al. |
| 2005/0064539 A1 | 3/2005 | Chiba et al. |
| 2005/0170452 A1 | 8/2005 | Wildt et al. |
| 2005/0265988 A1 | 12/2005 | Choi et al. |
| 2006/0014264 A1 | 1/2006 | Sauer et al. |
| 2006/0030521 A1 | 2/2006 | Defrees et al. |
| 2006/0040353 A1 | 2/2006 | Davidson et al. |
| 2006/0148039 A1 | 7/2006 | Kobayashi et al. |
| 2006/0286637 A1 | 12/2006 | Hamilton |
| 2007/0037248 A1 | 2/2007 | Bobrowicz et al. |
| 2008/0081035 A1* | 4/2008 | Parmely .................. C12N 9/62 424/94.63 |
| 2008/0171359 A1 | 7/2008 | Botes et al. |
| 2009/0186011 A1 | 7/2009 | Vellard et al. |
| 2010/0291059 A1 | 11/2010 | Sakuraba et al. |
| 2012/0135461 A1 | 5/2012 | Cook et al. |
| 2013/0053550 A1 | 2/2013 | Geysens et al. |
| 2013/0096281 A1 | 4/2013 | Ryckaert et al. |
| 2013/0158239 A1 | 6/2013 | Callewaert et al. |
| 2013/0195835 A1 | 8/2013 | Callewaert et al. |
| 2013/0267473 A1 | 10/2013 | Piens et al. |
| 2013/0295603 A1 | 11/2013 | Piens et al. |
| 2015/0031081 A1 | 1/2015 | Vervecken et al. |
| 2015/0337273 A1 | 11/2015 | Geysens et al. |
| 2016/0251693 A1 | 9/2016 | Piens et al. |
| 2017/0226493 A1 | 8/2017 | Callewaert et al. |
| 2017/0306379 A1 | 10/2017 | Piens et al. |

FOREIGN PATENT DOCUMENTS

| | | |
|---|---|---|
| FR | 2954349 | 6/2011 |
| JP | 57-054588 | 4/1982 |
| JP | 2002-369679 | 12/2002 |
| JP | 2004-313074 | 11/2004 |
| KR | 10-2004-0026663 | 3/2004 |
| KR | 20040062304 | 7/2004 |
| WO | WO 1992/019195 | 11/1992 |
| WO | WO 1995/005452 | 2/1995 |
| WO | WO 1996/004378 | 2/1996 |
| WO | WO 1996/021038 | 7/1996 |
| WO | WO 1998/001473 | 1/1998 |
| WO | WO 1998/001535 | 1/1998 |
| WO | WO 1998/048025 | 10/1998 |
| WO | WO 1999/036569 | 7/1999 |
| WO | WO 1999/037758 | 7/1999 |
| WO | WO 2001/049830 | 7/2001 |
| WO | WO 2001/088143 | 11/2001 |
| WO | WO 2002/018570 | 3/2002 |
| WO | WO 2003/029456 | 4/2003 |
| WO | WO 2003/056914 | 7/2003 |
| WO | WO 2004/003194 | 1/2004 |
| WO | WO 2004/074458 | 9/2004 |
| WO | WO 2004/074461 | 9/2004 |
| WO | WO 2004/074498 | 9/2004 |
| WO | WO 2004/074499 | 9/2004 |
| WO | WO 2005/100584 | 10/2005 |
| WO | WO 2005/106010 | 11/2005 |
| WO | WO 2007/035930 | 3/2007 |
| WO | WO 2008/100816 | 8/2008 |
| WO | WO 2008/120107 | 10/2008 |
| WO | WO 2009/105357 | 8/2009 |
| WO | WO 2009137721 | 11/2009 |
| WO | WO 2010/099195 | 9/2010 |
| WO | WO 2011/039634 | 4/2011 |
| WO | WO 2011/061629 | 5/2011 |
| WO | WO 2012/042386 | 4/2012 |
| WO | WO 2012/042387 | 4/2012 |
| WO | WO 2013/098651 | 7/2013 |

OTHER PUBLICATIONS

Van Hove et al., High-level production of recombinant human lysosomal acid alpha-glucosidase in Chinese hamster ovary cells which targets to heart muscle and corrects glycogen accumulation in fibroblasts from patients with Pompe disease, Proc. Natl. Acad. Sci. USA, 1996, 93, 65-70.*

Kishnani et al., Chinese Hamster Ovary Cell-Derived Recombinant Human Acid alpha-Glucosidase in Infantile-Onset Pompe Disease, J. Pediatr., 2006, 149, 89-97.*

Togawa et al., Comparative study on mannose 6-phosphate residue contents of recombinant lysosomal enzymes, Molecular Genetics Metabolism, 2014, 111, 369-73.*

Van der Ploeg et al., Intravenous Administration of Phosphorylated Acid a-Glucosidase Leads to Uptake of Enzyme in Heart and Skeletal Muscle of Mice, J. Clin. Invest., 1991, 87, 513-18.*

Database Geneseq, "Aspergillus oryzae alkaline protease, SEQ ID 1.", retrieved from EBI accession No. GSP:ARW11112, Database accession No. ARW11112, 1 page, Aug. 7, 2008.

García-Gómez et al., "Advantages of a proteolytic extract by Aspergillus myzae from fish flour over a commercial proteolytic preparation," Food Chemistry, 112(3):604-608, Feb. 1, 2009.

GenBank Accession No. AA034683, "mi41c04.r1 Soares mouse embryo NbME13.5 14.5 Mus musculus cDNA clone Image:466086 5-, mRNA sequence," Aug. 23, 1996, 2 pages.

GenBank Accession No. BAJ83907, "sulfatase modifying factor 1 [Hemicentrotus pulcherrimus]," Nov. 10, 2011, 2 pages.

GenBank Accession No. ELW48757.1, GI: 444707484, "Sulfatase-modifying factor 1 [Tupaia chinensis]," Jan. 31, 2013, 2 pages.

GenBank Accession No. ENN77245.1, GI: 478257082, "hypothetical protein YQE_06075, partial [Dendroctonus ponderosae]," Apr. 10, 2013, 2 pages.

GenBank Accession No. NP_001069544, "sulfatase-modifying factor 1 precursor [Bos taurus]," Jan. 23, 2012, 2 pages.

GenBank Accession No. NP_215226.1, "unnamed protein product [*Mycobacterium tuberculosis* H37Rv]," Jan. 19, 2012, 2 pages.

GenBank Accession No. NP_631591.1, "hypothetical protein SCO7548 [Streptomyces coelicolor A3(2)]," Jan. 19, 2012, 2 pages.

GenBank Accession No. XP_001374411, GI: 126336367, "Predicted: sulfatase-modifying factor 1-like [Monodelphis domestica]," May 31, 2011, 1 page.

GenBank Accession No. XP_003642070.1, GI: 363738801, "Predicted: sulfatase-modifying factor 1-like [Gallus gallus]," Dec. 16, 2011, 1 pages.

GenBank Accession No. XP_005511340.1, GI: 543740918, "Predicted: sulfatase-modifying factor 1 [Columba livia]," Sep. 15, 2013, 2 pages.

GenBank Accession No. XP_504265.1, GI: 50553708, "YALI0E22374p [Yarrowia lipolytica CLIB122]," Oct. 29, 2008, 2 pages.

Herscovics., "Processing glycosidases of *Saccharomyces cerevisiae*," Biochimica Biophysica. Acta, 1426(2):275-285, Jan. 6, 1999.

Hosokawa et al., "EDEM1 accelerates the trimming of alpha1,2-linked mannose on the C branch of N-glycans," Glycobiology., 20(5):567-575, Epub Jan. 11, 2010.

Kim et al., "Functional characterization of the Hansenula polymorpha HOC1, OCH1, and OCR1 genes as members of the yeast OCH1 mannosyltransferase family involved in protein glycosylation," J Biol Chem., 281(10):6261-6272, Epub Jan. 10, 2006.

Moreland et al., "Species-specific differences in the processing of acid α-glucosidase are due to the amino acid identity at position 201," Gene, 491(1):25-30, Jan. 1, 2012.

Odani et al., "Cloning and analysis of the MNN4 gene required for phosphorylation of N-linked oligosaccharides in *Saccharomyces cerevisiae*," Glycobiology., 6(8):805-810, Dec. 1996.

(56) References Cited

OTHER PUBLICATIONS

Odani et al., "Mannosylphosphate transfer to cell wall mannan is regulated by the transcriptional level of the MNN4 gene in *Saccharomyces cerevisiae*," FEBS Letters., 420(2-3):186-190, Dec. 29, 1997.
UniProtKB/Swiss-Prot: P01588, "Erythropoietin precursor (Epoetin)," Jul. 21, 1986, 7 pages.
UniProtKB/Swiss-Prot: P04062, "Glucosylceramidase precursor (Beta-glucocerebrosidase) (Acid beta-glucosidase) (D-glucosyl-N-acylsphingosine glucohydrolase) (Alglucerase) (Imiglucerase)," Nov. 1, 1986, 31 pages.
Korean Grounds for Rejection in Korean Patent Application No. 10-2009-7022979, dated Feb. 10, 2017, 4 pages with English translation.
Korean Grounds for Rejection in Korean Patent Application No. 10-2015-7035851, dated Feb. 10, 2017, 4 pages with English translation.
"Arxula adeninivorans," Wikipedia [online] Jan. 13, 2010 [retrieved on Jan. 31, 2010]. Retrieved from the Internet <URL: http://en.wikipedia.org/wiki/Arxula_adeninivorans>, 2 pages.
"Eukaryotes Genomes—Yarrowia Lipolytica," The European Bioinformatics Institute [online] [retrieved on Jun. 26, 2012]. Retrieved from the Internet: <URL: http://www.ebi.ac.uk/2can/genomes/eukaiyotes/Yarrowia_lipolytica.html>, 1 page.
"Glycoside Hydrolase Family 38," cazy.org [online] captured Sep. 11, 2010. Retrieved from the Internet: <URL: http://www.cazy.org/GH38.html>, 1 page.
"Glycoside Hydrolase Family 47," cazy.org [online] captured Sep. 12, 2010. Retrieved from the Internet: <URL: http://www.cazy.org/GH47.html>, 1 page.
"Glycoside Hydrolase Family 92," cazy.org [online] captured Sep. 12, 2010. Retrieved from the Internet: <URL: http://www.cazy.org/GH92.html>, 1 page.
Abe et al., "In vitro oligosaccharide synthesis using intact yeast cells that display glycosyltransferases at the cell surface through cell wall-anchored protein Pir.," *Glycobiology*, 13(2):87-95, print Feb. 2003, ePub Nov. 2002.
Ackerman et al., "Highly avid magnetic bead capture: an efficient selection method for de novo protein engineering utilizing yeast surface display," *Biotechnol Prog.*, 25(3):774-783, May-Jun. 2009.
Aebi et al., "Cloning and characterization of the ALG3 gene of *Saccharomyces cerevisiae*," Glycobiology, vol. 6, No. 4, (1996), pp. 439-444.
Akcapinar et al., "Effect of codon optimization on the expression of Trichoderma reesei endoglucanase 1 in Pichia pastoris." Biotechnol Prog., Sep.-Oct. 2011; 27(5):1257-1263. doi: 10.1002/btpr.663. Epub Jul. 2011.
Akeboshi et al., "Production of Recombinant Beta-Hexosaminidase A, a Potential Enzyme for Replacement Therapy for Tay-Sachs and Sandhoff Diseases, in the Methylotrophic Yeast *Ogataea minuta*", Appl. Environ. Microbiol., 73( 15):4805-4812 (2007).
Alessandrini et al., "Alterations of Glucosylceramide-b-Glucosidase Levels in the Skin of Patients with Psoriasis Vulgaris," J. Invest. Dermatol., 23(6):1030-1036, 2004.
Almeciga et al., "Production of an active recombinant human N-acetylgalactosamine-6-sulfate sulfatase enzyme in Pichia pastoris," *Molecular Genetics and Metabolism*, 111(2): S19, Abstract 11, Jan. 27, 2014.
Andrés et al., "Use of the cell wall protein Pir4 as a fusion partner for the expression of *Bacillus* sp. BP-7 xylanase A in *Saccharomyces cerevisiae*," Biotechnol Bioeng, 89(6): 690-697, Mar. 2005.
Aravind and Koonin, "The fukutin family—predicted enzymes modifying cell-surface molecules," Curr Biol., 9(22):R836-R837, Nov. 18, 1999.
Bagiyan et al., "The Action of α-Mannosidase from *Oerskovia* sp. on the Mannose-Rich O-Linked Sugar Chains of Glycoproteins," Eur. J. Biochem., 249(1):286-292, 1997.

Baharaeen and Vishniac, "A fixation method for visualization of yeast ultrastructure in the electron microscope ," Mycopathologia, 77(1):19-22, 1982.
Ballou, "Isolation, characterization, and properties of *Saccharomyces cerevisiae* mnn mutants with nonconditional protein glycosylation defects," Methods in Enzymology, vol. 185, (1990) pp. 440-470.
Barnay-Verdier et al., "Identification and characterization of two alpha-1,6-mannosyltmnsferases, Anllp and Ochlp, in the yeast yarrowia lipolytica", *Microbiology*, 150:2185-2195 (2004).
Barth and Gaillardin, "Physiology and genetics of the dimorphic fungus *Yarrowia lipolytica*," FEMS Microbiology Reviews, 19(4):219-237, Apr. 1997 [print], Jan. 2006 [online].
Bennetzen and Hall, "Codon Selection in Yeast" J. Biol. Chem., 257(6):3026-3031, 1982.
Bentley et al., "Complete genome sequence of the model actinomycete Streptomyces coelicolor A3(2)," Nature, 417:141-147, (May 2002).
Bijvoet et al., "Recombinant human acid alpha-glucosidase: high level production in mouse milk, biochemical characteristics, correction of enzyme deficiency in GSDII KO mice," Hum Mol Genet., 7(11):1815-1824, Oct. 1998.
Bobrowicz et al., "Engineering of an artificial glycosylation pathway blocked in core oligosaccharide assembly in the yeast *Pichia pastoris*: production of complex humanized glycoproteins with terminal galactose," *Glycobiology*, 14(9):757-766 (2004).
Boder and Wittrup, "Yeast surface display for screening combinatorial polypeptide libraries," *Nat. Biotechnol.*, 15, 553-557, Jun. 1997.
Boder et al. "Directed evolution of antibody fragments with monovalent femtomolar antigen-binding affinity," *Proc Natl Acad Sci U S A.*, 97(20):10701-5, Sep. 2000.
Boisrame et al. "Sls1p, an endoplasmic reticulum component, is involved in the protein translocation process in the yeast *Yarrowia lipolytica*," J. Biol. Chem. 271(20):11668-75, 1996.
Bourbonnais et al., "Production of full-length human pre-elafin, an elastase specific inhibitor, from yeast requires the absence of a functional yapsin 1 (Yps1p) endoprotease," *Protein Expr Purif.*, 20(3):485-491, Dec. 2000.
Brady, "Enzyme replacement for lysosmal diseases," *Annu. Rev. Med.*, 57:283-296, 2006.
Brady, "The lipid storage diseases: new concepts and control," *Ann Intern Med.*, 82(2):257-61, Feb. 1975.
Bretthauer, "Genetic engineering of Pichia pastoris to humanize N-glycosylation of proteins," TRENDS in Biotechnology, 21(11): 459-462 (Nov. 2003).
Burda et al., "Ordered assembly of the asymmetrically branched lipid-linked oligosaccharide in the endoplasmic reticulum is ensured by the substrate specificity of the individual glycosyltransferases", *Glycobiology*, 9(6):617-625 (1999).
Burton and Harding, "Hydrophobic charge induction chromatography: salt independent protein adsorption and facile elution with aqueous buffers.," J. Chromatogr. A 814(1-2):71-81, Jul. 1998.
Callewaert et al, "Use of HDEL-tagged Trichoderma reesei mannosyl oligosaccharide 1,2-alpha-D-mannosidase for N-glycan engineering in Pichia pastoris.," FEBS Lett., 503(2-3):173-178, (Aug. 2001).
Callewaert et al., "Ultmsensitive profiling and sequencing of N-linked oligosaccharides using standard DNA-sequencing equipment," Glycobiology 11(4):275-281, Apr. 2001.
Cantarel et al., "The Carbohydrate-Active EnZymes database (CAZy): an expert resource for Glycogenomics," *Nucleic Acids Res.*, 37(Database issue):D233-D238, Epub Oct. 5, 2008.
Cardone et al., "Abnormal mannose-6-phosphate receptor trafficking impairs recombinant alpha-glucosidase uptake in Pompe disease fibroblasts," Pathogenetics, 1(1):6, Dec. 1, 2008.
Carlson et al., "Function and structure of a prokaryotic formylglycine-generating enzyme," *J Biol Chem.*, 283(29):20117-20125, Epub Apr. 4, 2008.
Carter et al., "Humanization of an anti-p185HER2 antibody for human cancer therapy," *Proc Natl Acad Sci USA*, 89(10): 4285-4289, (May 1992).
Chao et al., "Isolating and engineering human antibodies using yeast surface display," *Nat. Protoc.*, 1(2):755-768, 2006.

(56) References Cited

OTHER PUBLICATIONS

Chiba et al., "Production of human compatible high mannose-type (Man5GlcNAc2) sugar chains in *Saccharomyces cerevisiae*," *J Biol Chem.*, 273(41):26298-26304, Oct. 9, 1998.
Chiba et al., "Production in yeast of alpha-galactosidase A, a lysosomal enzyme applicable to enzyme replacement therapy for Fabry disease," *Glycobiology*, 12(12):821-828 (2002).
Cho et al., "Structure of the extracellular region of HER2 alone and in complex with the Herceptin," *Nature*, 421(6924):756-760, Feb. 2003.
Choi et al "Use of combinatorial genetic libraries to humanize N-linked glycosylation in the yeast Pichia pastoris," Proc. Natl. Acad. Sci. USA, 100(9):5022-5027, Apr. 2003.
Choi, "Structural analysis of N-linked oligosaccharides assembled on recombinant proteins secreted from Yarrowia lipolytica Yloch1 and Yloch1 Ylmnn4 mutants," Thesis, Chungnam National University: Department of Microbiology, Republic of Korea, pp. 1-39, XP008160421, Retrieved from the Internet: URL: http://www.riss.kr/search/detail/DetailView.do?p_mat_type=75f99de66db18cf6&control_no=4cbf0006e9061fb5ffe0bdc3ef48d419 (2006).
Choi, et al., "Structural analysis of N-linked oligosaccharides assembled on recombinant proteins secreted from Yarrowia lipolytica Yloch1 and Yloch1 Ylmnn4 mutants.," XXIIth International Conference on Yeast Genetics and Molecular Biology, 09—Protein biosynthesis, maturation, modification and degradation, Yeast, 22:5131, Abstract 9-35, 2005.
Cipollo and Trimble, "The accumulation of Man(6)GlcNAc(2)-PP-dolichol in the *Saccharomyces cerevisiae* Deltaalg9 mutant reveals a regulatory role for the Alg3p alpha1,3-Man middle-arm addition in downstream oligosaccharide-lipid and glycoprotein glycan processing," J Biol Chem., 275(6):4267-4277, (Feb. 2000).
Cobucci-Ponzano et al., "The molecular characterization of a novel GH38 alpha-mannosidase from the crenarchaeon Sulfolobus solfataricus revealed its ability in de-mannosylating glycoproteins," Biochimie., 92(12):1895-1907, (Aug. 2010).
Codon usage table: Yarrowia lipolytica CLIB122 [gbpln]: 5967 CDS's (2945919 codons), Codon Usage Database [online], [retrieved on Jul. 10, 2012]. Retrieved from the Internet< URL: http://www.kazusa.or.jp/codon/cgi-bin/showcodon.cgi?species=284591>, 1 page.
Connock et al., "A systematic review of the clinical effectiveness and cost-effectiveness of enzyme replacement therapies for Fabry's disease and mucopolysaccharidosis type 1," Health Technol Assess., 10(20):iii-iv, ix-113, 2006.
Database Accession No. P41546, UniProt (online), "RecName: Full Transcriptionmanal Activator HAC1"; XP002509286, Nojima et al., Nov. 1, 1995, 3 pages.
Database UniProt[Online] Aug. 1, 1998 (Aug. 1, 1998), "SubName: Full= Putative secreted protein;" XP002628929 retrieved from EBI accession No. UNIPROT:069822 Database accession No. 069822, 3 pages.
Database UniProt[Online] Jul. 11, 2006 (Jul. 11, 2006), "SubName: Full= Alpha-1, 2-mannosidase, putative; Flags: Precursor;" XP002628931 retrieved from EBI accession No. UNIPROT:Q1ASW5 Database accession No. Q1ASW5, 2 pages.
Database UniProt[Online] Apr. 29, 2008 (Apr. 29, 2008), "SubName: Full= Putative uncharacterized protein;" XP002628930 retrieved from EBI accession No. UNIPROT:B1BZG6 Database accession No. B1BZG6, 2 pages.
Davidow et al., "Cloning and sequencing of the alkaline extracellular protease gene of Yarrowia lipolytica," *J. Bacteriol.*, 169(10):4621-4629, Oct. 1987.
Davies et al, "Nomenclature for sugar-binding subsites in glycosyl hydrolases," Biochem. J., 321:557-559 (1997).
De Pourcq et al, "Engineering Yarrowia lipolytica to produce glycoproteins homogeneously modified with the universal Man3GlcNAc2 N-glycan core," PLoS One, 7(6):e39976, 12 pages, Epub Jun. 29, 2012.
De Pourcq et al., "Engineering of glycosylation in yeast and other fungi: current state and perspectives," *Appl Microbiol Biotechnol.*, 87(5):1617-1631. Epub Jun. 29, 2010.
De Pourcq et al., "Engineering the yeast *Yarrowia lipoytica* for the production of therapeutic proteins homogeneously glycosylated with Man8GlcNAc2 and MansGIcNAc2," *Microbial Cell Factories*, 11:53, 1-12, May 1, 2012.
Devos and Valencia, "Practical limits of function prediction," *Proteins.*, 41(1):98-107, Oct. 1, 2000.
Dragosits et al., "The effect of temperature on the proteome of recombinant Pichia pastoris," *J. Proteome Res.*, 8(3):1380-1392, Mar. 2009.
Ekici et al., "Unconventional serine proteases: variations on the catalytic Ser/His/Asp triad configuration," *Protein Sci.*, 17(12):2023-2037, Epub Sep. 29, 2008.
Ettinger et al., "Intrathecal methotrexate overdose without neurotoxicity: case report and literature review," Cancer, 41(4):1270-1273, Apr. 1978.
Fickers et al. "New disruption cassettes for rapid gene disruption and marker rescue in the yeast *Yarrowia lipolytica*," J. Microbiol. Methods. 55(3):727-737, Dec. 2003.
Fickers et al., "Carbon and nitrogen sources modulate lipase production in the yeast *Yarrowia lypolytica*," J. of Applied Microbiology, vol. 96, No. 4 (2004), pp. 742-749.
Fickers, P. et al. "Hydrophobic substrate utilization by the yeast *Yarrowia lipolytica* and its potential applications," *FEMS Yeast Research*, Apr. 2005, vol. 5, No. 6-7, pp. 527-543.
Fournier et al.' "Scarcity of ars sequences isolated in a morphogenesis mutant of the yeast *Yarrowia lipolytica,*" Yeast, 7(1):25-36, Jan. 1991.
Freire et al. "Efficient monitoring of enzymatic conjugation reaction by surface-enhanced laser desorption/ionization time of flight mass spectrometry for process optimization," Bioconjug. Chem. 17(2):559-564, 2006.
Fujii, "Antibody Affinity Maturation by Random Mutagenesis," *Antibody Engineering*, vol. 248, pp. 345-359, 2004.
Fujita and Takegawa, "Chemoenzymatic Synthesis of Neoglycoproteins Using Transglycosylation with Endo-Beta-N-acetylglucosaminidase A," Biochem. Biophys. Res. Commun., 282(3):678-682, (Apr. 2001).
Gagnon-Arsenault et al., "Activation mechanism, functional role and shedding of glycosylphosphatidylinositol-anchored Yps1p at the *Saccharomyces cerevisiae* cell surface," Mol Microbiol., 69(4):982-993, Epub Jun. 28, 2008.
Gagnon-Arsenault et al., "Fungal yapsins and cell wall: a unique family of aspartic peptidases for a distinctive cellular function," FEMS Yeast Res., 6(7):966-978, Nov. 2006.
Gao et al. "UpGene: Application of a web-based DNA codon optimization algorithm," Biotechnol. Prog., 20(2): 443-448, 2004.
Gasser et al., "Engineering of Pichia pastoris for improved production of antibody fragments," *Biotechnol. Bioeng.*, 94(2):353-361, Jun. 2006.
Gatlin et al., "Automated identification of amino acid sequence variations in proteins by HPLC/microspray tandem mass spectrometry," Anal Chem., 72(4):757-763, Feb. 15, 2000.
Gellissen, et al., "New yeast expression platforms based on methylotrophic Hansenula polymorpha and Pichia pastoris and on dimorphic Arxula adeninivorans and Yarrowia lipolytica—A comparison," FEMS Yeast Res., 5(11): 1079-1096, 2005.
Genbank Acccession No. XM_502922 GI:50550898, "Yarrowia lipolytica YALI0D17028p (YALI0D17028g) mRNA, complete cds," Oct. 29, 2008, 2 pages.
Genbank Acccession No. XM_503217 GI:50551486, "Yarrowia lipolytica YALI0D24101p (YALI0D24101g) mRNA, complete cds," Oct. 29, 2008, 2 pages.
Genbank Accession No. AAF34579 GI:6979644, "1,2-a-D-mannosidase [Trichoderma reesei]" Feb. 16, 2000, 1 page.
GenBank Accession No. AAO78636, "putative alpha-1,2-mannosidase [Bacteroides thetaiotaomicron VPI-5482]," 1 page, Oct. 24, 2007.
Genbank Accession No. AAO78636.1 GI:29340846, putative alpha-1,2-mannosidase [Bacteroides thetaiotaomicron VPI-5482] Feb. 8, 2011, 2 pages.
Genbank Accession No. AAO79070.1 GI:29341282, "putative alpha-1,2-mannosidase [Bacteroides thetaiotaomicron VPI-5482]," Feb. 8, 2011, 2 pages.

(56) References Cited

OTHER PUBLICATIONS

Genbank Accession No. AAO79099.1, "putative alpha-1,2-mannosidase [Bacteroides thetaiotaomicron VPI-5482]," Feb. 8, 2011, 2 pages.
Genbank Accession No. AF212153 GI:6979643, "Hypocrea jecorina 1,2-a-D-mannosidase (MDS1) mRNA, complete cds," Feb. 16, 2000, 2 pages.
GenBank Accession No. AF441127 GI:16974782, "Yarrowia lipolytica Mnn9p (mnn9) gene, complete cds," Apr. 11, 2003, 2 pages.
GenBank Accession No. AJ563920 GI:38488499, "Yarrowia lipolytica och1 gene for alpha 1,6 mannosyltransferase," Nov. 20, 2003, 2 pages.
GenBank Accession No. AJ865333 GI:56266607, "Trypanosoma brucei brucei glcaseIIa gene for glucosidase II alpha subunit precursor," Oct. 25, 2005, 2 pages.
GenBank Accession No. BAA00258.1 GI:217809, "alkaline protease, partial [Aspergillus olyzae]," Dec. 20, 2002, 2 pages.
GenBank Accession No. BAA08634 GI:1171477, "alpha-mannosidase [Aspergillus saitoi]" Feb. 10, 1999, 1 page.
GenBank Accession No. NP_630514 GI:21224735, "hypothetical protein SCO6428 [Streptomyces coelicolor A3(2)]," Jan. 19, 2012, 3 pages.
GenBank Accession No. NP_630514, "secreted protein [Streptomyces coelicolor A3(2)]," 2 pages, Sep. 26, 2008.
GenBank Accession No. NP_812442 GI:29348939, "alpha-1,2-mannosidase [Bacteroides thetaiotaomicron VPI-5482]" Jan. 20, 2012, 2 pages.
Genbank Accession No. XM_499811 GI:50543289, "Yarrowia lipolytica YALI0A06589p (YALI0A06589g) mRNA, complete cds," Oct. 29, 2008, 2 pages.
GenBank Accession No. XM_500574 GI:50546093, "Yarrowia lipolytica YALI0B06600p (YALI0B06600g) mRNA, complete cds," Oct. 29, 2008, 2 pages.
Genbank Accession No. XM_500811 GI:50546682, "Yarrowia lipolytica YALI0B12716p (YALI0B12716g) mRNA, complete cds," Oct. 29, 2008, 2 pages.
GenBank Accession No. XM_503488 GI:50552026, "Yarrowia lipolytica YALI0E03190p (YALI0E03190g) mRNA, complete cds," Oct. 29, 2008, 2 pages.
GenBank Accession No. XP_503768, GI: 50552716, "YALI0E10175p [Yarrowia lipolytica CLIB122]," Oct. 29, 2008, 2 pages.
GenBank Accession No. YP_003013376 YP_003013376, "alpha-1,2-mannosidase [*Paenibacillus* sp. JDR-2]" Jun. 15, 2012, 3 pages.
GenBank Accession No. YP_003120664 GI:256420011, "alpha-1,2-mannosidase [Chitinophaga pinensis DSM 2588]," Jun. 18, 2012, 2 pages.
GenBank Accession No. YP_003584502 GI:295133826, "alpha-1,2-mannosidase [Zunongwangia profunda SM-A87]," Nov. 21, 2011, 2 pages.
GenBank Accession No. Z49631 GI:1015863, "*S.cerevisiae* chromosome X reading frame ORF YJR131w," Aug. 11, 1997, 2 pages.
GenBank Accession No. ZP_01061975 GI:86143590, "putative alpha-1,2-mannosidas [Leeuwenhoekiella blandensis MED217]," Nov. 9, 2010, 1 page.
GenBank Accession No. ZP_01885202 GI:149279069, "putative alpha-1,2-mannosidase [*Pedobacter* sp. BAL39]," Nov. 9, 2010, 1 page.
GenBank Accession No. ZP_02866543 GI:169349605, "hypothetical protein CLOSPI_00343 [Clostridium spiroforme DSM 1552]," Nov. 9, 2010, 2 pages.
GenBank Accession No. ZP_03677957 GI: 224537418, "hypothetical protein BACCELL_02296 [Bacteroides cellulosilyticus DSM 14838]," Nov. 10, 2010, 1 page.
GenBank Accession No. ZP_04848482 GI:253571075, "conserved hypothetical protein [*Bacteroides* sp. 1_1_6]" Jun. 9, 2010, 2 pages.
GenBank Accession No. ZP_05522540 GI:256784109, "secreted protein [Streptomyces lividans TK24]," Dec. 9, 2010, 2 pages.
GenBank Accession No. ZP_06527366 GI:289767988, "secreted protein [Streptomyces lividans TK24]" Oct. 26, 2010, 3 pages.

GenBank Accession No. ZP_07083984 GI:300774115, "probable alpha-1,2-mannosidase [Sphingobacterium spiritivorum ATCC 33861]," Dec. 1, 2010, 1 page.
GenBank, "Yarrowia lipolytica CLIB122 [gbpln]: 5967 CDS's (2945919 codons)," Codon Usage Database, [online], Jun. 15, 2007 [retrieved on Aug. 15, 2014]. Retrieved from the Internet: <URL: http://www.kazusa.or.jp/codon/cgi-bin/showcodon.cgi?species=284591>, 1 page.
Gentzsch and Tanner, "The PMT gene family: protein O-glycosylation in *Saccharomyces cerevisiae* is vital," Embo J, 15(21):5752-5759, (1996).
Gerngross, "Advances in the production of human therapeutic proteins in yeasts and filamentous fungi," Nature Biotech., 22(11):1409-1414, (2004).
Ghaemmaghami et al., "Global analysis of protein expression in yeast." Nature. vol. 425, No. 6959 (Oct. 2003) pp. 737-741.
Gilbert, "Glycoside Hydrolase Family 92," CAZypedia [online], Mar. 4, 2010. Retrieved from the Internet: <URL: http://www.cazypedia.org/index.php/Glycoside_Hydrolase_Family_92>, 3 pages.
Gonzalez and Jordan, "The alpha-mannosidases: Phylogeny and adaptive diversification," Mol Biol Evol., 17(2):292-300, (Feb. 2000).
Gossen and Bujard, "Studying gene function in eukaryotes by conditional gene inactivation," Ann. Rev. Genetics 36:153-173, (2002).
Grinna and Robbins, "Substrate specificities of rat liver microsomal glucosidases which process glycoproteins," J. Biol. Chem., 255(6):2255-2258, (1980).
Grubb et al., "New strategies for enzyme replacement therapy for lysosomal storage diseases," *Rejuvenation Res.*, 13(2-3):229-236, Apr.-Jun. 2010.
Guarente et al., "A GAL10-CYC1 hybrid yeast promoter identifies the GAL4 regulatory region as an upstream site," *Proc Natl Acad Sci U S A.*, 79(23):7410-7414, Dec. 1982.
Hamilton and Gerngross, "Glycosylation engineering in yeast: the advent of fully humanized yeast," Curr Opin Biotechnol., 18(5):387-392, (Oct. 2007).
Hamilton et al, "Production of complex human glycoproteins in yeast," Science, 301(5637):1244-1246, Aug. 2003.
Hedstrom, "Serine protease mechanism and specificity," *Chem Rev.*, 102(12):4501-4524, Dec. 2002.
Henderson and Finn, "Human tumor antigens are ready to fly," Advances in Immunology, 62:217-256 (1996).
Henrissat, "A classification of glycosyl hydrolases based on amino acid sequence similarities," *Biochem J.*, 280 ( Pt 2):309-316, Dec. 1, 1991.
Hermans et al., "Human lysosomal alpha-glucosidase: functional characterization of the glycosylation sites," Biochem J., 289 ( Pt 3):681-686, (Feb. 1993).
Hinnen et al. "Transformation of yeast," *Proc Natl Acad Sci U S A.*, 75(4):1929-1933, Apr. 1978.
Howard et al., "Identification of the Active Site Nucleophile in Jack Bean alpha-Mannosidase Using 5-Fluoro-beta-L-Gulosyl Fluoride," J. Biol. Chem., 273(4):2067-2072, 1998.
Hudson and Kora, "High avidity scFv multimers; diabodies and triabodies," J. Immunol. Methods, 231(1-2):177-189, (1999).
Huston et al. "Engineered antibodies take center stage," Hum. Antibodies, 10(3-4):127-142, (2001).
Ichishima et al., "Molecular and enzymic properties of recombinant 1,2-alpha-mannosidase from Aspergillus saitoi overexpressed in Aspergillus oryzae cells," Biochem. J., 339: 589-597, (1999).
Inoue et al., "Molecular cloning and nucleotide sequence of the 1,2-alpha-D-mannosidase gene, msdS, from Aspergillus saitoi and expression of the gene in yeast cells," Biochim Biophys Acta. 1253(2):141-145, Dec. 6, 1995.
Ito et al., "Transformation of intact yeast cells treated with alkali cations," J. Bacteriol., 153(1):163-168, (1983).
Jaafar et al., "Isolation of the MNN9 gene of Yarrowia lipolytica (Y1MNN9) and phenotype analysis of a mutant y1mnn9 Delta strain," Yeast, 20(7):633-644, May 2003.
Jacobs et al. "Engineering complex-type N-glycosylation in Pichia pastoris using GlycoSwitch technology," Nat Protoc., 2009;4(1):58-70., Epub Dec. 18, 2008.

(56) References Cited

OTHER PUBLICATIONS

Klis et al., "Cell wall construction in *Saccharomyces cerevisiae*," *Yeast*, 23(3):185-202, 2006.

Komeda et al., "Construction of protease-deficient Candida boidinii strains useful for recombinant protein production: cloning and disruption of proteinase A gene (PEP4) and proteinase B gene (PRBI)," Biosci Biotechnol Biochem., 66(3):628-631, Mar. 2002.

Kornfeld and Kornfeld, "Assembly of asparagine-linked oligosaccharides," Annu Rev Biochem., 54:631-664, (1985).

Kotula and Curtis, "Evaluation of foreign gene codon optimization in yeast: expression of a mouse IG kappa chain," Biotechnology (N Y)., 9(12):1386-1389, (1991).

Kuroda et al., "Production of Man5GlcNAc2-type sugar chain by the methylotrophic yeast *Ogataea minuta*," FEMS Yeast Res., 6:1052-1062 (2006).

Kuroda et al., "Antibody expression in protease-deficient strains of the methylotrophic yeast *Ogataea minuta*," FEMS Yeast Res., 7(8):1307-1316. Epub Aug. 22, 2007.

Landgrebe et al., "The human SUMF1 gene, required for post-translational sulfatase modification, defines a new gene family which is conserved from pro- to eukaryotes," *Gene.*, 316:47-56, Oct. 16, 2003.

Laroy et al., "Glycome mapping on DNA sequencing equipment," Nature Protocols, 1: 397-405 (2006).

Le Dall et al., "Multiple-copy integration in the yeast *Yarrowia lipolytica*," Curr Genet., 26(1):38-44, Jul. 1994.

Lee and Park, "Enzymatic in vitro glycosylation using peptide-N-glycosidase F," Enzyme and Microbial Technology, 30(6):716-720, (2002).

Li et al., "Optimization of humanized IgGs in glycoengineered Pichia pastoris," *Nat Biotechnol.*, 24(2):210-215, Epub Jan. 22, 2006.

Liang et al., "The crystal structures of two cuticle-degrading proteases from nematophagous fungi and their contribution to infection against nematodes," *FASEB J.*, 24(5):1391-1400, Epub Dec. 9, 2009.

Liao et al., "Cloning, expression, purification, and characterization of the human broad specificity lysosomal acid alpha-mannosidase," J. Biol Chem., 271(45):28348-28358, (Nov. 1996).

Lin et al., "Display of a functional hetero-oligomeric catalytic antibody on the yeast cell surface," *App. Microbiol Biotechol.*, 62(2-3): 226-232, print Aug. 2003, Epub Mar. 2003.

Liu et al., "Disruption of the OCH1 and MNN1 genes decrease N-glycosylation on glycoprotein expressed in Kluyveromyces lactis," J Biotechnol., 143(2):95-102, Epub Jun. 24, 2009.

Lobsanov et al., "Modulation of activity by Arg407: structure of a fungal alpha-1,2-mannosidase in complex with a substrate analogue," Acta Crystallogr D Biol Crystallogr., 64(Pt 3):227-236, (2008).

Luer and Hatton, "Vancomycin administration into the cerebrospinal fluid: a review," Annals of Pharmacotherapy, 27:912-921, 1993.

Madzak et al., "Heterologous protein expression and secretion in the non-conventional yeast *Yarrowia lipolytica*: a review," J Biotechnol., 109(1-2):63-81, Apr. 8, 2004.

Madzak et al., "Strong hybrid promoters and integrative expression/secretion vectors for quasi-constitutive expression of heterologous proteins in the yeast *Yarrowia lipolytica*," J Mol Microbiol Biotechnol., 2(2):207-216, (Apr. 2000).

Maras et al., "Molecular cloning and enzymatic characterization of a Trichoderma reesei 1, 2-alpha-D-mannosidase," J. Biotechnol, 77: 255-263 (2000).

Martinet et al., "Protection of mice against a lethal influenza challenge by immunization with yeast-derived recombinant influenza neuraminidase," Eur J Biochem., 247(1):332-338, (Jul. 1997).

Mast and Moremen, "Family 47 alpha-mannosidases in N-glycan processing," *Methods Enzymol.*, 415:31-46, 2006.

Matsuoka et al., "Analysis of regions essential for the function of chromosomal replicator sequences from Yarrowia lipolytica," *Mol. Gen. Genet.*, 237(3):327-333, Mar. 1993.

Merkle et al., Cloning, expression, purification, and characterization of the murine lysosomal acid alpha-mannosidase, Biochim Biophys Acta, 1336(2):132-146, (Aug. 1997).

Mille et al., "Identification of a new family of genes involved in beta-1,2-mannosylation of glycans in Pichia pastoris and Candida albicans," J Biol Chem., 283(15):9724-9736. Epub Jan. 30, 2008.

Moreau and Morré, "Cell-free transfer of membrane lipids. Evidence for lipid processing," *J Biol Chem.*, 266(7):4329-4333, Mar. 5, 1991.

Moreau et al., "Trafficking of lipids from the endoplasmic reticulum to the Golgi apparatus in a cell-free system from rat liver," *J Biol Chem.*, 266(7):4322-4328, Mar. 5, 1991.

Moreland et al., "Lysosomal acid alpha-glucosidase consists of four different peptides processed from a single chain precursor," *J Biol Chem.*, 280(8):6780-6791, Epub Nov. 1, 2004.

Mori et al., "Signalling from endoplasmic reticulum to nucleus: transcription factor with a basic-leucine zipper motif is required for the unfolded protein-response pathway," Genes Cells, vol. 1, No. 9 (Sep. 1996), pp. 803-817.

Morya et al., "In silico characterization of alkaline proteases from different species of *Aspergillus*," *Appl Biochem Biotechnol.*, 166(1):243-257, Epub Nov. 10, 2011.

Nakadai et al., "Purification and Properties of Alkaline Proteinase from Aspergillus myzae," Agr. Biol. Chem., 37(12): 2685-2694, 1973.

Newman and Ferro-Novick, "Characterization of new mutants in the early part of the yeast secretory pathway isolated by a [3H]mannose suicide selection," J. Cell Biol., 105(4):1587-1594, (1987).

Nicaud et al., "Protein expression and secretion in the yeast *Yarrowia lipolytica*," FEMS Yeast Res., 2(3):371-379, Aug. 2002.

Orlean et al., "Cloning and sequencing of the yeast gene for dolichol phosphate mannose synthase, an essential protein," J. Biol. Chem., vol. 263, (Nov. 1988), pp. 17499-17507.

Park et al, "Essential role of Y1MPO1, a novel Yarrowia lipolytica homologue of *Saccharomyces cerevisiae* MNN4, in mannosylphosphorylation of N- and O-linked glycans," Appl Environ Microbiol., 77(4):1187-1195, Epub Dec. 23, 2010.

Paulik et al., "Cell-free transfer of the vesicular stomatitis virus G protein from an endoplasmic reticulum compartment of baby hamster kidney cells to a rat liver Golgi apparatus compartment for Man8-9 to Man5 processing," Arch Biochem Biophys., 367(2):265-273, Jul. 15, 1999.

Peberdy et al., "Protein secretion by fungi," Applied Micolog and Biotechnology, Agriculture and Food Production, 1:73-114, 2001.

Penttilä et al., "Expression of two Trichoderma reesei endoglucanases in the yeast *Saccharomyces cerevisiae*," *Yeast.*, 3(3):175-185, Sep. 1987.

Perona and Craik et al., "Structural basis of substrate specificity in the serine proteases," *Protein Sci.*, 4(3):337-360, Mar. 1995.

Pignède et al., "Characterization of an extracellular lipase encoded by LIP2 in Yarrowia lipolytica," *J. Bacteriol.*, 182(10):2802-10, May 2000.

Platt and Lachmann, "Treating lysosomal storage disorders: Current practice and future prospects," Biochim Biophys Acta, 1793(4):737-745, 2009.

Poljak, "Production and structure of diabodies," Structure, 2(12):1121-1123, (1994).

Potgieter et al., "Production of monoclonal antibodies by glycoengineered Pichia pastoris," *J Biotechnol.*, Feb. 23, 2009;139(4):318-325, Epub Dec. 27, 2008.

Protein Data Bank, "Structure of the GH92 Family Glycosylhydrolase CCMAN5" Deposition: Sep. 29, 2010 [retrieved on Jul. 17, 2012]. Retrieved from the Internet: <URL: http://www.pdb.org/pdb/explore/explore.do?structureId=2XSG>, 2 pages.

Rakestraw and Wittrup, "Contrasting secretory processing of simultaneously expressed heterologous proteins in *Saccharomyces cerevisiae*," *Biotechnol. Bioeng.*, 93(5):896-905, Apr. 2006.

Rawlings and Barrett "Evolutionary families of peptidases," *Biochem J.*, 290 ( Pt 1):205-218, Feb. 15, 1993.

Rexach et al., "Distinct biochemical requirements for the budding, targeting, and fusion of ER-derived transport vesicles," *J Cell Biol.*, 114(2):219-229, Jul. 1991.

(56) References Cited

OTHER PUBLICATIONS

Richard et al., "Tagging morphogenetic genes by insertional mutagenesis in the yeast *Yarrowia lipolytica*," J Bacteriol., 183(10):3098-3107, (May 2001).
Rodriguez et al., "Production of recombinant human N-acetylgalactosamine-6-sulfate sulfatase enzyme in Pichia pastoris," *Molecular Genetics and Metabolism*, 108(2): S79-S80, Abstract 197, Feb. 1, 2013.
Rose, "Glycoside Hydrolase Family 38," CAZypedia [online], Feb. 2, 2010. Retrieved from the Internet: <URL: http://www.cazypedia.org/index.php/Glycoside_Hydrolase_Family_38>, 3 pages.
Ruiz-Herrera and Sentandreu, "Different effectors of dimorphism in Yarrowia lipolytica," *Arch. Microbiol.*, 178(6): 477-483, print Dec. 2002, Epub Oct. 2002.
Ryckaert et al., "Isolation of antigen-binding camelid heavy chain antibody fragments (nanobodies) from an immune library displayed on the surface of Pichia pastoris," *J Biotechnol.*, 145(2):93-98, Epub Oct. 2009, print Jan. 2010.
Seffernick et al., "Melamine deaminase and atrazine chlorohydrolase: 98 percent identical but functionally different," J Bacteriol., 183(8):2405-2410, Apr. 2001.
Shusta et al., "Increasing the secretory capacity of *Saccharomyces cerevisiae* for production of single-chain antibody fragments," *Nat. Biotechnol.*, 16(8): 773-777, Aug. 1998.
Shusta et al., "Yeast polypeptide fusion surface display levels predict thermal stability and soluble secretion efficiency," *J. Mol. Biol.*, 292(5):949-956, Oct. 1999.
Siezen et al., "Subtilases: the superfamily of subtilisin-like serine proteases," *Protein Sci.*, 6(3):501-523, Mar. 1997.
Smith and Waterman, "Comparison of biosequences," Adv. Appl. Math., 2(4):482-489, (Dec. 1981).
Song et al., "Characterization of Genes Invoked in N-glycosylation in Yarrowia lipolytica," Yeast, 20:S147 (2003).
Song et al., "Engineering of the Yeast *Yarrowia lipolytica* for the Production of Glycoproteins Lacking the Outer-Chain Mannose Residues of N-Glycans," Appl Environ Microbiol., vol. 73, No. 14 (Jul. 2007), pp. 4446-4454.
Sreekrishna et al., "Invertase gene (SUC2) of *Saccharomyces cerevisiae* as a dominant marker for transformation of Pichia pastoris," *Gene*, 59(1):115-125, 1987.
Stocks, "Intrabodies: production and promise," Drug Discov. Today 9(22): 960-966, (Nov. 2004).
Swennen et al., "Folding proteome of Yarrowia lipolytica targeting with uracil permease mutants," J Proteome Res., 9(12):6169-6179, Epub Nov. 12, 2010.
Swennen et al., "Secretion of active anti-Ras single-chain Fv antibody by the yeasts *Yarrowia lipolytica* and *Kluyveromyces lactis,*" *Microbiology*, 148(Pt 1):41-50, Jan. 2002.
Swiss Protein Accession No. P15291, Nov. 30, 2010, 9 pages.
Swiss Protein Accession No. P26572, Nov. 30, 2010, 4 pages.
Swiss Protein Accession No. P38069, Nov. 30, 2010, 3 pages.
Swiss Protein Accession No. Q09326, Nov. 30, 2010, 3 pages.
Swiss Protein Accession No. Q24451, Nov. 30, 2010, 12 pages.
Tajima et al., "Use of a modified alpha-N-acetylgalactosaminidase in the development of enzyme replacement therapy for Fabry disease," *Am J Hum Genet.*, 85(5):569-580 Epub Oct. 22, 2009.
Tanino et al., "Construction of a Pichia pastoris cell-surface display system using Flo 1p anchor system," *Biotechnol. Prog.*, 22(4): 989-993, Jul.-Aug. 2006.
Tiels et al., "A bacterial glycosidase enables mannose-6-phosphate modification and improved cellular uptake of yeast-produced recombinant human lysosomal enzymes," Nat Biotechnol., 30(12):1225-1231, Epub Nov. 18, 2012.
Tremblay and Herscovics, "Cloning and expression of a specific human alpha 1,2-mannosidase that trims Man9GlcNAc2 to Man8GlcNAc2 isomer B during N-glycan biosynthesis," Glycobiology., 9(10):1073-1078, (Oct. 1999).
Ueda et al "Cell surface engineering of yeast: construction of arming yeast with biocatalyst," *J. Biosci. Bioeng.*, 90(2): 125-136, 2000.

UniProtKB/Swiss-Prot: P06280.1 GI:113499, "RecName: Full=Alpha-galactosidase A; AltName: Full=Alpha-D-galactosidase A; AltName: Full=Alpha-D-galactoside galactohydrolase; AltName: Full=Melibiase; AltName: INN=Agalsidase; Flags: Precursor," Jun. 13, 2012, 26 pages.
UniProtKB/Swiss-Prot: P15291.5 GI:116241264, "RecName: Full=Beta-1,4-galactosyltransferase 1; Short=Beta-1,4-GalTase 1; Short=Beta4Gal-T1; Short=b4Gal-T1; AltName: Full=UDP-Gal:beta-GlcNAc beta-1,4-galactosyltransferase 1; AltName: Full=UDP-galactose:beta-N-acetylglucosamine beta-1,4-galactosyltransferase . . . " Jun. 13, 2012, 10 pages.
UniProtKB/Swiss-Prot: P26572.2 GI:311033399, "RecName: Full=Alpha-1,3-mannosyl-glycoprotein 2-beta-N-acetylglucosaminyltransferase; AltName: Full=N-glycosyl-oligosaccharide-glycoprotein N-acetylglucosaminyltransferase I; Short=GNT-I; Short=GlcNAc-T I," Apr. 18, 2012, 6 pages.
UniProtKB/Swiss-Prot: P27809.1 GI:127214, "RecName: Full=Glycolipid 2-alpha-mannosyltransferase; AltName: Full=Alpha-1,2-mannosyltransferase," Jun. 13, 2012, 8 pages.
UniProtKB/Swiss-Prot: P38069.1 GI:586137, "RecName: Full=Alpha-1,2-mannosyltransferase MNN2; AltName: Full=Calcium resistance and vanadate sensitivity protein 4; AltName: Full=Mannan synthesis protein MNN2," Jun. 13, 2012, 5 pages.
UniProtKB/Swiss-Prot: Q09326.1 GI:1169978, "RecName: Full=Alpha-1,6-mannosyl-glycoprotein 2-beta-N-acetylglucosaminyltransferase; AltName: Full=Beta-1,2-N-acetylglucosaminyltransferase II; AltName: Full=GlcNAc-T II; Short=GNT-II; AltName: Full=Mannoside acetylglucosaminyltransferase 2; AltName: Full=N-g . . . ," Jun. 13, 2012, 3 pages.
UniProtKB/Swiss-Prot: Q24451.2 GI:32130434, "RecName: Full=Alpha-mannosidase 2; AltName: Full=Golgi alpha-mannosidase II; Short=AMan II; Short=Man II; AltName: Full=Mannosyl-oligosaccharide 1,3-1,6-alpha-mannosidase," Apr. 18, 2012, 13 pages.
UniProtKB/Swiss-Prot: Q9Y7X5.1 GI:74698597, "RecName: Full=Uncharacterized protein C365.14c," May 16, 2012, 2 pages.
van den Elsen et al., "Structure of Golgi alpha-mannosidase II: a target for inhibition of growth and metastasis of cancer cells," *EMBO J.*, 20(12):3008-3017, Jun. 15, 2001.
Van Hove et al., "High-level production of recombinant human lysosomal acid alpha-glucosidase in Chinese hamster ovary cells which targets to heart muscle and corrects glycogen accumulation in fibroblasts from patients with Pompe disease," Proc Natl Acad Sci U S A., 93(1):65-70, Jan. 9, 1996.
VanAntwerp and Wittrup, "Fine affinity discrimination by yeast surface display and flow cytometry," *Biotechnol. Prog.*, 16(1): 31-7, Jan.-Feb. 2000.
Vandersall-Nairn et al., "Cloning, expression, purification, and characterization of the acid α-mannosidase from Trypanosoma cruzi," Glycobiology, 8(12):1183-1194, (1998).
Vega et al., "Partial characterization of α-mannosidase from Yarrowia lipolytica," *J Basic Microbiol.*, 28(6):371-379, ePub Jan. 10, 2007.
Vernis et al., "An origin of replication and a centromere are both needed to establish a replicative plasmid in the yeast *Yarrowia lipolytica,*" *Mol. Cell Biol.*, 17(4): 1995-2004, Apr. 1997.
Verostek et al., "Glycoprotein biosynthesis in the alg3 *Saccharomyces cerevisiae* mutant. I. Role of glucose in the initial glycosylation of invertase in the endoplasmic reticulum," The Journal of Biological Chemistry, vol. 268, (Jun. 5, 1993), pp. 12095-12103.
Verostek et al., "Glycoprotein biosynthesis in the alg3 *Saccharomyces cerevisiae* mutant. II. Structure of novel Man6-10GlcNAc2 processing intermediates on secreted invertase," The Journal of Biological Chemistry, vol. 268, pp. 12104-12115, (Jun. 5, 1993).
Vervecken et al. "In Vivo Synthesis of Mammalian-Like, Hybrid-Type N-Glycans in Pichia pastoris," Appl. Environ. Microb., 70(5):2639-2646, (May 2004).
Vervecken et al., "Modification of the N-glycosylation pathway to produce homogeneous, human-like glycans using GlycoSwitch plasmids," Methods Mol Biol., 389:119-138, 2007.
Vocadlo et al., "Mechanistic insights into glycosidase chemistry," Curr. Opin. Chem. Biol., 12:539-555 (2008).

(56) References Cited

OTHER PUBLICATIONS

Wang and Shusta, "The use of scFv-displaying yeast in mammalian cell surface selections," *J. Immunol. Methods*, 304(1-2):30-42, Sep. 2005.
Wang et al.. "A new yeast display vector permitting free scFv amino termini can augment ligand binding affinities," *Protein Eng. Des. Sel.*, 18(7): 337-343, print Jul. 2005, Epub Jun. 2005.
Wang et al., "Construction of a novel Pichia pastoris cell-surface display system based on the cell wall protein Pir1," *Curr. Microbiol.*, 56(4): 352-357, Apr. 2008.
Ward et al., "Characterization of Humanized Antibodies Secreted by Aspergillus niger," Appl. Environ. Microbiol., 70(5):2567-2576, (May 2004).
Wheeler et al. "Intrabody and Intrakine Strategies for Molecular Therapy," Mol. Ther., 8(3):355-366, (Sep. 2003).
Whisstock and Lesk, "Prediction of protein function from protein sequence and structure," *Q Rev Biophys.*, 36(3):307-340, Aug. 2003.
Witkowski et al. "Conversion of a beta-ketoacyl synthase to a malonyl decarboxylase by replacement of the active-site cysteine with glutamine," Biochemistry, 38(36):11643-11650, Sep. 7, 1999.
Wright et al., "Structure of subtilisin BPN' at 2.5 angström resolution," Nature, 221(5177):235-242, Jan. 18, 1969.
Wu et al., Asparagine-linked glycosylational modifications in yeast, Cell Engineering, 3:215-232, 2002.
YALI0A16819g YALI0A16819p[Yarrowia lipolytica CLIB122] Gene ID: 2906333, created on Jul. 24, 2004, 2 pages.
YALI0C10135g YALI0C10135p[Yarrowia lipolytica CLIB122] Gene ID: 7009445, created on Oct. 29, 2008, 2 pages.
YALI0D10835g YALI0D10835p[Yarrowia lipolytica CLIB122] Gene ID: 2910442, created on Jul. 24, 2004, 2 pages.
YALI0E10175g YALI0E10175p[Yarrowia lipolytica CLIB122] Gene ID: 2912589, created on Jul. 28, 2004, 2 pages.
YALI0E20823g YALI0E20823p[Yarrowia lipolytica CLIB122] Gene ID: 2911836, created on Jul. 28, 2004, 2 pages.
YALI0E22374g YALI0E22374p[Yarrowia lipolytica CLIB122] Gene ID: 2912981, created on Jul. 28, 2004, 2 pages.
YALI0E24981g YALI0E24981p[Yarrowia lipolytica CLIB122 Gene ID: 2912672, created on Jul. 28, 2004, 2 pages.
YALI0E34331g YALI0E34331p[Yarrowia lipolytica CLIB122] Gene ID: 2912367, created on Jul. 28, 2004, 2 pages.
Yang et al., "Cell-surface display of the active mannanase in Yarrowia lipolytica with a novel surface-display system," Biotechnol Appl Biochem, vol. 54, No. 3 (Oct. 2009), pp. 171-176.
Yao et al., "Degradation of HSA-AX15(R13K) when expressed in Pichia pastoris can be reduced via the disruption of YPS1 gene in this yeast," *J Biotechnol.*, 139(2):131-136. Epub Oct. 8, 2008.
Yeung and Wittrup, "Quantitative screening of yeast surface-displayed polypeptide libraries by magnetic bead capture," *Biotechnol. Prog.*, 18(2):212-220, Mar.-Apr. 2002.
Ying et al., "Soluble monomeric IgG1 Fc," *J Biol Chem.*, 287(23):19399-19408, Epub Apr. 19, 2012.
Yue et al., "Construction of a new plasmid for surface display on cells of Yarrowia lipolytica," J Microbiol Methods, vol. 72, No. 2 (Feb. 2008), pp. 116-123.
Zhu and Zhang, "SCPD: a promotor database of the yeast *Saccharomyces cerevisiae*," Bioinformatics, 15(7-8):607-611, (1999).
Zhu et al., "Glycoengineered acid alpha-glucosidase with improved efficacy at correcting the metabolic aberrations and motor function deficits in a mouse model of Pompe disease," Mol Ther., 17(6):954-963, Epub Mar. 10, 2009.
Zhu et al., "Mechanistic insights into a Ca2+-dependent family of alpha-mannosidases in a human gut symbiont," Nat. Chem. Biol., 6(2):125-132. Epub Dec. 27, 2009 (2010).
Zimm et al., "Cerebrospinal fluid pharmacokinetics of intraventricular and intravenous aziridinylbenzoquinone," Cancer Research, 44(4):1698-1701, Apr. 1984.
Cregg et al., "Transformation," *Molecular Biology*: Pichia Protocols, Chapter 3, Humana Press, Totowa, N.J., pp. 27-39 (1998).

Dierks et al., "Multiple sulfatase deficiency is caused by mutations in the gene encoding the human C(alpha)-formylglycine generating enzyme," *Cell*, 113(4):435-444, May 16, 2003.
Dierks et al., "Sequence determinants directing conversion of cysteine to formylglycine in eukaryotic sulfatases," *EMBO J.*, 18(8):2084-2091, Apr. 15, 1999.
Diez-Roux and Ballabio, "Sulfatases and human disease," *Annu Rev Genomics Hum Genet.*, 6:355-379, 2005.
Floudas, "Computational methods in protein structure prediction," Biotechnology and Bioengineering, 97(2): 207-213, Jun. 1, 2007.
Fraldi et al., "Multistep, sequential control of the trafficking and function of the multiple sulfatase deficiency gene product, SUMF1 by PDI, ERGIC-53 and ERp44," *Hum Mol Genet.*, 17(17):2610-2621, Epub May 28, 2008.
Gande et al., "Paralog of the formylglycine-generating enzyme-retention in the endoplasmic reticulum by canonical and noncanonical signals," *FEBS J.*, 275(6):1118-1130, Epub Feb. 6, 2008.
GenBank Accession: CAC87611.1, "ERp44 protein [*Homo sapiens*]," 2 pages, Oct. 7, 2008.
Grove et al., "In vitro characterization of AtsB, a radical SAM formylglycine-generating enzyme that contains three [4Fe-4S] clusters," *Biochemistry*, 47(28):7523-7538, Epub Jun. 18, 2008.
Guo et al., "Protein tolerance to random amino acid change," *Proc Natl Acad Sci U S A.*, 101(25):9205-9210, Epub Jun. 14, 2004.
InterPro—Protein sequence anaylsis and classification, "Species: Sulfatase-modifying factor enzyme (IPR005532)," EMBL-EBI, [online]. Retrieved from the Internet: <URL: http://www.ebi.ac.uk/interpro/entry/IPR005532/taxonomy:jsessionid=A50B4C8B868FB85867E9D179F3959BED>, 2 pages, retrieved on Nov. 3, 2015.
Lobsanov et al., "Structure of Penicillium citrinum alpha 1,2-mannosidase reveals the basis for differences in specificity of the endoplasmic reticulum and Golgi class I enzymes," *J Biol Chem.*, 277(7):5620-5630, Epub Nov. 19, 2001.
Mariappan et al., "ERp44 mediates a thiol-independent retention of formylglycine-generating enzyme in the endoplasmic reticulum," *J Biol Chem.*, 283(10):6375-6383, Epub Jan. 4, 2008.
NCBI Reference Sequence: NP_000909.2, "protein disulfide-isomerase precursor [*Homo sapiens*]," Mar. 24, 2012, 4 pages.
NCBI Reference Sequence: XP_502492.1, "YALI0D06589p [Yarrowia lipolytica CL1B122]," 2 pages, Oct. 29, 2008.
NCBI Reference Sequence: XP_502939.1, "YALI0D17424p [Yarrowia lipolytica CLIB122]," 2 pages, Oct. 29, 2008.
Nett et al., "A combinatorial genetic library approach to target heterologous glycosylation enzymes to the endoplasmic reticulum or the Golgi apparatus of Pichia pastoris," *Yeast.*, 28(3):237-252, Epub Jan. 6, 2011.
Rabuka et al., "Site-specific chemical protein conjugation using genetically encoded aldehyde tags," *Nat Protoc.*, 7(6):1052-1067, May 10, 2012.
Roeser et al., "A general binding mechanism for all human sulfatases by the formylglycine-generating enzyme," *Proc Natl Acad Sci U S A.*, 103(1):81-86, Epub Dec. 20, 2005.
Sakuma et al., "HpSumf1 is involved in the activation of sulfatases responsible for regulation of skeletogenesis during sea urchin development," *Dev Genes Evol.*, 221(3):157-166, Epub Jun. 27, 2011.
Sardiello et al., "Sulfatases and sulfatase modifying factors: an exclusive and promiscuous relationship," *Hum Mol Genet.*, 14(21):3203-3217, Epub Sep. 20, 2005.
Voznyi et al., "A fluorimetric enzyme assay for the diagnosis of MPS II (Hunter disease)," *J Inherit Metab Dis.*, 24(6):675-680, Nov. 2001.
Zhu et al., "Mechanistic insights into a Ca2+-dependent family of alpha-mannosidases in a human gut symbiont," Nat. Chem. Biol., 6(2):125-132. Supplementary Information, 25 pages. Epub Dec. 27, 2009, 2010.
Zito et al., "Sulphatase activities are regulated by the interaction of sulphatase-modifying factor 1 with SUMF2," *EMBO Rep.*, 6(7):655-660, Jul. 2005.
International Search Report and Written Opinion for PCT/IB2013/000912, dated Dec. 12, 2013, 21 pages.

(56) References Cited

OTHER PUBLICATIONS

Invitation to pay additional fees and, where applicable, protest fee, for PCT/IB2013/000912, mailed Sep. 30, 2013, 8 pages.
U.S. Appl. No. 12/062,469, filed Apr. 3, 2008, now U.S. Pat. No. 8,026,083, Sep. 27, 2011, Callewaert.
U.S. Appl. No. 13/094,606, filed Apr. 26, 2011, now U.S. Pat. No. 8,597,906, Dec. 3, 2013, Callewaert.
U.S. Appl. No. 13/095,532, filed Apr. 27, 2011, now U.S. Pat. No. 9,222,083, Dec. 29, 2015, Callewaert.
U.S. Appl. No. 13/499,061, filed Sep. 6, 2012, 2013/0158239, Jun. 20, 2013, Callewaert.
U.S. Appl. No. 13/510,527, filed Oct. 31, 2012, 2013/0053550, Feb. 28, 2013, Geysens.
U.S. Appl. No. 13/620,259, filed Sep. 14, 2012, 2013/0195835, Aug. 1, 2013, Callewaert.
U.S. Appl. No. 13/620,306, filed Sep. 14, 2012, now U.S. Pat. No. 9,206,408, Dec. 8, 2015, Callewaert.
U.S. Appl. No. 13/831,368, filed Mar. 14, 2013, now U.S. Pat. No. 9,249,399, Feb. 2, 2016, Vervecken.
U.S. Appl. No. 13/876,730, filed Mar. 28, 2013, 2013/0295603, Nov. 7, 2013, Piens.
U.S. Appl. No. 13/876,769, filed Jun. 19, 2013, 2013/0267473, Oct. 10, 2013, Piens.
U.S. Appl. No. 14/369,324, filed Jun. 27, 2014, 2015/0031081, Jan. 29, 2015, Vervecken.
U.S. Appl. No. 14/641,002, filed Mar. 6, 2015, 2015/0337273, Nov. 26, 2015, Geysens et al.
U.S. Appl. No. 14/773,234, filed Sep. 4, 2015, Vervecken.
Bones et al., "Identification of N-Glycans Displaying Mannose-6-Phosphate and their Site of Attachment on Therapeutic Enzymes for Lysosomal Storage Disorder Treatment," Analytical Chemistry., 83(13):5344-5352, May 23, 2011.
Chinese Office Action in International Application No. 201410681757.1, dated Aug. 11, 2017, 5 pages (with English Translation).
European Office Action in European Application No. EP10782375.9, dated Jun. 16, 2017, 6 pages.
Glycoside Hydrolase Family 38, accessed Jul. 30, 2017 at URL cazypedia.org/index.php/Glycoside_Hydrolase_Family_38, 1 page.
Lee et al., "A biochemical and pharmacological comparison of enzyme replacement therapies for the glycolipid storage disorder Fabry disease," Glycobiology., 13:305-313, 2003.
Russian Office Action in International Application No. 2014139953, dated May 10, 2017, 6 pages (with English Translation).
Tatsumi et al., "Cloning and Sequencing of the Alkaline Protease cDNA from Aspergillus Oryzae," Agric Biol Chem., 52(7):1887-1888, 1988.
European Office Action in International Application No. EP 13729065.6, dated Oct. 17, 2017, 4 pages.
Wisselaar et al., "Structural and functional changes of lysosomal acid a-glucosidase during intracellular transport and maturation," J Biol Chem., 268(3):2223-2231, Jan. 25, 1993.
U.S. Appl. No. 15/350,648, filed Dec. 14, 2016, Callewaert.
U.S. Appl. No. 15/594,256, filed May 12, 2017, Piens.
U.S. Appl. No. 15/087,201, filed Mar. 31, 2016, Piens.
Bohnsack et al., "Cation-independent mannose 6-phosphate receptor," J Biol Chem., 284(50):35215-35226, Dec. 11, 2009.
glycoforum.gr.jp' [online] "α-Mannosidases and EDEM homolog proteins: their roles in glycoprotein ERAD," Jun. 5, 2006, Retrieved online Feb. 15, 2018, Retrieved URL: http://www.glycoforum.gr.jp/science/word/qualitycontrol/QS-A02E.html, 2 pages.
Makde et al., "Structure and Mutational Analysis of the PhoN Protein of *Salmonella typhimurium* Provide Insight into Mechanistic Details," Biochemistry., 46:2079-2090, 2007.
Song et al., "Glycan Microarray analysis of P-type lectins reveals distinct phosphomannose glycan recognition," J Biol Chem., 284(50):35201-35214, Dec. 11, 2009.
Korean Office Action in International Application No. 10-2013-7011113, dated Nov. 14, 2017, 13 pages (with English Translation).
Korean Office Action in International Application No. 10-2013-7011110, dated Nov. 14, 2017, 16 pages (with English Translation).
Japanese Office Action in International Application No. 2017-000348, dated Jan. 17, 2018, 12 pages (with English Translation).
Japanese Office Action in International Application No. 2016-042290, dated Jan. 24, 2018, 19 pages (with English Translation).
Alberts et al's Molecular Biology of the Cell, 4th ed., Garland Science, New York, 2002, ISGN 0-8153-3577-6, 2002, Chapter 3, pp. 129-134.
Canadian Office Action in Canada Application No. 2,775,938, dated Aug. 24, 2018, 7 pages.

* cited by examiner

AAQQGASRPGPRDAQAHPGRPRAVPTQCDVPPNSREDCAPDKAITQEQCEARGCCYIPAKQGL
QGAQMGQPWCFFPPSYPSYKLENLSSSEMGYTATLTRTTPTFFPKDILTLRLDVMMETENRLH
FTIKDPANRRYEVPLETPHVHSRAPSPLYSVEFSEEPFGVIVRRQLDGRVLLNTTVAPLFFAD
QFLQLSTSLPSQYITGLAEHLSPLMLSTSWTRITLWNRDLAPTPGANLYGSHPFYLALEDGGS
AHGVFLLNSNAMDVVLQPSPALSWRSTGGILDVYIFLGPEPKSVVQQYLDVVGYPFMPPYWGL
GFHLCRWGYSSTAITRQVVENMTRAHFPLDVQWNDLDYMDSRRDFTFNKDGFRDFPAMVQELH
QGGRRYMMIVDPAISSSGPAGSYRPYDEGLRRGVFITNETGQPLIGKVWPGSTAFPDFTNPTA
LAWWEDMVAEFHDQVPFDGMWIDMNEPSNFIRGSEDGCPNNELENPPYVPGVVGTLQAATIC
ASSHQFLSTHYNLHNLYGLTEAIASHRALVKARGTRPFVISRSTFAGHGRYAGHWTGDVWSSW
EQLASSVPEILQFNLLGVPLVGADVCGFLGNTSEELCVRWTQLGAFYPFMRNHNSLLSLPQEP
YSFSEPAQQAMRKALTLRYALLPHLYTLFHQAHVAGETVARPLFLEFPKDSSTWTVDHQLLWG
EALLITPVLQAGKAEVTGYFPLGTWYDLQTVPVEALGSLPPPAAPREPAIHSEGQWTLPAP
LDTINVHLRAGYIIPLQGPGLTTESRQQPMALAVALTKGEARGELFWDDGESLEVLERGAY
TQVIEFLARNTIVNELVRVTSEGAGLQLQKVTVLGVATAPQQVLSNGVPVSNFTYSPDTKVLD
ICVSLLMGEQFLVSWC* (SEQ ID NO:1)

FIG. 1

>DsbA-6xHis-CcMan5 (107bp - 5167bp, direct) 5061bp From pLSAHCcMan5

ATGAAAAAGATTTGGCTGGCGCTGGCTGGTTTAGTTTTAGCGTTTAGCGCATCGGCCGGCCATCACCATCATCACCA
CGTGGGGCCCGGCTCGGACGAAGTGGATGCACCGGAACCTCCGAGCGCAGATTATGCAAGCCTGGTTGATGTTTTTG
TTGGCACCGAAGGTGATTTTGGTAATGATATGCCTGCAGCACAGGCACCGAATGGTCTGGCAAAAGTTAATCCGCGT
ACCACACCGGGTCGTAATAATACCGGTTATGATTATGCCCAGAGCAAAATTAGCGGTTTTACCCATACCAATCTGGA
TGGTGTTGGTGGTAGCGGTGGTGGTGGTGATCTGCTGGTTGTTCCGACCAGCGGTAGCTATACCGCACGTCCGGGTA
CAGGCACCTATGCACATCCGTTTAGCCATGATGATGAAGATGCAGGTCCGGGTTTTTATAGCGTTGGTCTGGGTAAT
GTTGCAGGCACCGATGGTGCAATTACCGGTGCTCCGGGTACAATTGAAGCAGAAGTTGCAGCAGCAACCCGTAGCGG
TGTTCATCGTTATGCATTTCCGGCAGGTAGCACCCCGAGCCTGGTTGTTGATCTGGAAACCAATAATACCAGCCGTC
GTAGCAGCAGCGTTCAGGTTGAAACCCGTGCAGATGGCACCGTTGAACTGAGCGGTCAGGTTACCGGCTATTTTTAT
AATGCAGCCTATACCCTGTATTATACCGCACGCACCCTGCAGCCTGCAACCGTTCAGACCTGGGGTGATGATGATCG
TCTGGTTGATGCAACCGCACAGGATGGTGTTGATACCGGTGCAATTCTGACCTTTGATCCGGCAGATGCCGGTGAAA
TTGGTCTGCAGGTTACCCTGTCTCCGGTTAGCGTTGAACAGGCACGTATTGATCAGCAGGTTGAACTGGGTGATCTG
AGCTTTGATGCAATTCGTGATCGTACCCGTGCAGAATGGAATGCAACCCTGGGTCGTGTTGCAATTGATGCAAGCAC
CGCAACCGATCCGACCGGTGAACTGCAGCGTCTGTTTTATACCCATCTGTATCGCATGTTTGCAATGCCGATGAATG
CAACCAGCACCAGCGGCACCTATCGTGGTGTTGATGGTGCAGTTCATGCAGCACAGGGCTTTACCTATTATGATAGC
TGGGCAACCTGGGATGATTTTCGCAAATTTAGCGTGATTGCCTATATTGATCCGGCACTGTATCGTGATATGGTTCA
GAGCCTGGTTTACCTGTTTGCAGATGCAGAAGCAACCGGTACAGGCGGTGGTCTGGGTGGTTTTGTTCATAGCGTTC
CGACCGTTCGTTGGGAACGTAGCAGCGTTGTTGTTGCAGATGCAATTGCCAAAGGCTTTGATGGTTTTGATCGTCTG
GATGAAGCATATCCGGCACTGCAGCGCCTGGTTGGTCAGTATAGCGCAGATGAACTGCGTCGTGGTTATGTTGCAGG
TAATCCGGGTGCAAGCGTTCAGCGTGGTTATGATCAGTATGGTCTGAGCGTTATTGCCGATGAACTGGGTCTGACCG
AAGAAGCAGAAACCCTGCGCGAACAGGCAAGCTGGCCGATTGAAAAACTGACCAAACCGGGTGCATGGACCGCAGCA
GATGGTACACAGGTTGGTCTGCTGACACCGCGTGCAGCCGATGGTAGCTGGCAGAGCGCAGATCATGCCAAATTTGA
AGCAGCAGGTCTGTATCAGGGCACCCTGTGGCAGTATCATTGGTATGATGCCTATGATATGGATGCACTGGTTGAAG
CAATGGGTGGTCATGAAGCAGCCCGTCTGGGTATGCGTCATATGTTTGGTGAACATGCACCGGATGATGGTAAAGCA
ATGCTGCATAGCAATGCCAATGAAATTGATCTGCAGGCACCGTACCTGTTTAATTATACCGGTGAACCGAGCCTGAC
CCAGAAATGGGCACGTGCAATTTATACCAAAGAAACCTGGAATCGCTATATTGCAACCGGTAGCAGCTCTGCAGTTC
CGTCAGGTGGTGGTGAATTTACACCTCCGCTGAAAACCAAAGTTTATCGTCTGGACCCTCGTGGTATGCTGCCGACC
ATGGATAATGATGCAGGTACAATGAGCACCATGTTTGTTGCAGCAGCCGTTGGTCTGTTTCCGGTTACCGCAGGTAG
CAGCCAGTTTCAGGTTGGTAGCCCGTTTTTTGATAGCACCACCATTACCTATGATGATGGTAGCGCATTTACCGTTA
CCGCAGATGGTGTTAGCGAAGATGCCTTTTATGTTCAGAGCGCAAACCCTGGATGGTGCAACCTTTGGTAATACCTGG
GTTGATTATGCAACCGTTGTTGGTGGTGCAGATCTGGCATTTCGTATGGGTGAACAGCCGAGCGATTGGGGCACCGA
TACCGCACCGGCATTTAGCATGAGCACCGCCACCGATGAACCGGCAGAAGGTCCTCGCGTTAGCGCAGAACCGACCA
CCGTGCAGACCGGTGATGGTGGTGCACTGGATGCAACCGTTACCCTGACACTGGATGGCGCACGTCTGGCAGCACCG
GCAGGTACAGATCTGGTTACCAGCGGTGCAGCAAGCGTTGTTGGTCTGCCGGATGGTGTTACCGCAGCAGTTACCGT
TGCAAGCCCGACCGCACTGACCGTTAGCCTGACCGGCACCGCATCAGCAGATGCACGTTTTTTTGTGCATCTGCGTG
ATGCAGCACTGGCCGATGGTGTTGCAGCCGCAAGCCTGCAGGGTCAGGGTGTTAGCGTTCGTTCTCCGCTGCGTCTG
AGCGTTGCAAGCGCAGAACGTGATGCACTGGCAGCACTGGTTGATGATGCCGTTCTGGTTCGTCATGGTAATTATAG
CAGCGTTACCTTTGATCGTTTAGCACCGCTCTGACAAAAGCACAGGAAGCACTGGGCGACGAAGCAGCAACCAGCAT
TGCACTGCGTTTTGCAGCAGATCGTCTGGGTGCAGCAGCAGATGCACTGGATCTGACCGGTGGTGGTTATCGTACCC
TGGAAGCAGAACAGAGCGAAGCATGGTCTGGTGGTGAACTGAAAAATGAAGCCAATAGCAGCAGCGGTAATCTGGGT
GGTGTTCGTAGCGGTAGCTGGGTTCAGTATCGCGATATGACCTTTGAAACCGCAGCCGGTGATACACCTCCGCGTTT
TCTGACCGTTCGTTATGATACCAGCTTTGCACCGACCGATACCCCGAGCACCGTTCGTGTTCATGCCGGTGATGTTT
CTGGTCCGGTTGTTGCAACCGTTGATCTGAAAGGCACCAGCGGTTGGGTAAATATACCGAAGTTACCGCAGAACTG
GGTGATGTTCAGGCCCTGGTTGATGCCCAGGTTGTTACCTTTGAACTGCTGGCACCGAGCGGTCGTAGCTGGGTTGG
TAATTTTGATTGGTTTCGCTTTAGCGCAGAAGATCCGGCAGCACCGGGTCAGCCTGGTGAAAGCCCGACCGTTACCA
TTGAAGCCGAAGATTGGACCGCAAGCAGCGGTCGTGGTCTGAAAAAAGAAAGCAGCACCTGGACCAGCGGTCCGGTG
ACCAATGTTGGTGGTACAGCAGATGGTGATTGGATTGCCTATGGTGAAGTTGATCTGGGTGAACTGCCGCTGGGCGA
ACTGAGCGTTCATTATGTGCATAATAGCAATCGCAGCGGTAATAATAGCGC

FIG. 2A

```
ACTGAGCGTTTATCTGGATGCATTTGATCCGGCTAATCCGGGTGAACCGTTTGTTACCGTTCCGCTGCCGA
CCACCGGTAGCAGTTGGACCAGATGGCCAGATGGCCACAGCCGAACCGTGTTCTGCGAAACCGTGCAGGCACCCAT
GAAGTTTTGTTCGTCTGAGCACCGAACCGTATGCAGATCATCCGTATGTTGCAAATCTGGATAGCCTGAC
CTTTGCACCGGTGGTCCGACCAGCGTTGTTGGTTGAAAGCCTGGACCAGCAATTCTGGTCGTGGCC
TGAAAAATGAATCTTCTACCTGGACCCTCCGGTTACAAATGTGGGTGCACCGCTGATGGCGATTGG
CTGGCATATGCCGAAATTGATCTGGGCAGCGCAGTCAGCTGTCTGTGCATTATGTTCATAATTC
TAATCGCTCTGGTCGTAATTCTGCACTGTCTGGATGCCGTTTGATCCGGCAAATCCGGGTGAAAC
CGTTTGTGACAGTGCCGCTGGCAAATACCGGTAGCTCTTGGACCACCGATGTACTGCAGTGTGGATCTG
CCGTCTACCGTTCGTGGTAAACATCAGGTTTGGGTTCGTCTGTCTACCGAAGCATATGCCGATCATCCGTA
TGTTGGCCAATCTGGATTCTATGCGCTTTTTTTACCGATGCATATGATGTTCCTCCGACCGATACAG
CAGCACTGGCAGCCGTTGTTGATGCAGCAGGTACACCGGAAGCAGAAATTGCACGTTATGGTCGTATTGAT
GCCCGTGTTTTTACCGTGAACTGCTCGTCTGGGTTCTGGCCGATGCCGGTCAACACAGGCACA
GGCAGATGAACGTGCTCGTGGCCAGCGCAGCACTGAGCTTCCGCAGAACAGCTGTCGTCTGG
AAAATCTGGTGCCAGCGCAGAAGCACTGACCGAAGGTTATTCTCCGGAAAGCTGGCAGGCATTTCGT
ACCGGACTGGCTGCAGCCGCTGCGCAACCGGCACCCCTGGATGATGAAGAACATCTGATGAAGCACTGATGATGCACG
TCTGGCGCTGCAGGGTGCAGTTGCACTGAAGAACCGGCAGATGTTGTTCTGGTTGAAGTTGAAGTTT
CTCCGGTTCTGGCAGGTAAACCGTTATGTGCAGTAATGTTTCTGATGCAGCCGTTGAT
GTTGAACTGGCAAGCTCTCTGGCACCCGGTTTGTTGGTGCACCGGGTGCCGAGCGCATATCAGAG
CTTTTGCAGCCCGTAGCGCAACCGGTGATCTGGATGTTACCGTGACCGCAACCGTTGCAGATGGTACTCAGA
CCGTTGAACAGGTTGTGACCCGTTCCGAGCTGTAGCTAATAA (SEQ ID NO:2)
```

FIG. 2A (continued)

ALAVVGLAPATAASAAPEPPSADYASLVDVFVGTEGDFGNDMPAAQAPNGLAKVNP
RTTPGRNNTGYDYAQSKISGFTHTNLDGVGGSGGGDLLVVPTSGSYTARPGTGTY
AHPFSHDDEDAGPGFYSVGLGNVAGTDGAITGAPGTIEAEVAAATRSGVHRYAFPA
GSTPSLVVDLETNNTSRRSSSVQVETRADGTVELSGQVTGYFYNAAYTLYYTARTL
QPATVQTWGDDDRLVDATAQDGVDTGAILTFDPADAGEIGLQVTLSPVSVEQARID
QQVELGDLSFDAIRDRTRAEWNATLGRVAIDASTATDPTGELQRLFYTHLYRMFAM
PMNATSTSGTYRGVDGAVHAAQGFTYYDSWATWDDFRKFSVIAYIDPALYRDMVQS
LVYLFADAEATGTGGGLGGFVHSVPTVRWERSSVVVADAIAKGFDGFDRLDEAYPA
LQRLVGQYSADELRRGYVAGNPGASVQRGYDQYGLSVIADELGLTEEAETLREQAS
WPIEKLTKPGAWTAADGTQVGLLTPRAADGSWQSADHAKFEAAGLYQGTLWQYHWY
DAYDMDALVEAMGGHEAARLGMRHMFGEHAPDDGKAMLHSNANEIDLQAPYLFNYT
GEPSLTQKWARAIYTKETWNRYIATGSSSAVPSGGGEFTPPLKTKVYRLDPRGMLP
TMDNDAGTMSTMFVAAAVGLFPVTAGSSQFQVGSPFFDSTTITYDDGSAFTVTADG
VSEDAFYVQSATLDGATFGNTWVDYATVVGGADLAFRMGEQPSDWGTDTAPAFSMS
TATDEPAEGPRVSAEPTTVQTGDGGALDATVTLTLDGARLAAPAGTDLVTSGAASV
VGLPDGVTAAVTVASPTALTVSLTGTASADARFFVHLRDAALADGVAAASLQGQGV
SVRSPLRLSVASAERDALAALVDDAVLVRHGNYSSVTFDRFSTALTKAQEALGDEA
ATSIALRFAADRLGAAADALDLTGGGYRTLEAEQSEAWSGGELKNEANSSSGNLGG
VRSGSWVQYRDMTFETAAGDTPPRFLTVRYDTSFAPTDTPSTVRVHAGDVSGPVVA
TVDLKGTSGWGKYTEVTAELGDVQALVDAQVVTFELLAPSGRSWVGNFDWFRFSAE
DPAAPGQPGESPTVTIEAEDWTASSGRGLKKESSTWTSGPVTNVGGTADGDWIAYG
EVDLGELPLGELSVHYVHNSNRSGNNSALSVYLDAFDPANPGEPFVTVPLPTTGSS
WTADGTATVVLPETVQGTHEVFVRLSTEPYADHPYVANLDSLTFAPGGPTSVVVES
EAWTSNSGRGLKNESSTWTSGPVTNVGGTADGDWLAYGEIDLGSAALDQLSVHYVH
NSNRSGRNSALSVYLDAFDPANPGEPFVTVPLANTGSSWTTDGTAVVDLPSTVRGK
HQVWVRLSTEAYADHPYVANLDSMRFFTDAYDVEVPPTDTAALAAVVDAAGTPEAE
IARYGRIDARVFTRELAAARSVLADAGATQAQADERARRLGLATDQLVPAERRRLE
NLVASAEALTDEGYSPESWQAFRTALAAATGTLDDAAASDEALHDARLALQGAVDA
LEEPADVVLVEVEVSPRCLAGKPYVAVRAVNVSDAAVDVELASSLGTRSFVGVAPG
ASAYQSFAARSATGDLDVTVTATGADGTQTVEQVVTVPSCS (SEQ ID NO:3)

FIG. 2B

APEPPSADYASLVDVFVGTEGDFGNDMPAAQAPNGLAKVNPRTTPGRNNTGYDYAQSK
ISGFTHTNLDGVGGSGGGGDLLVVPTSGSYTARPGTGTYAHPFSHDDEDAGPGFYSVG
LGNVAGTDGAITGAPGTIEAEVAAATRSGVHRYAFPAGSTPSLVVDLETNNTSRRSSS
VQVETRADGTVELSGQVTGYFYNAAYTLYYTARTLQPATVQTWGDDDRLVDATAQDGV
DTGAILTFDPADAGEIGLQVTLSPVSVEQARIDQQVELGDLSFDAIRDRTRAEWNATL
GRVAIDASTATDPTGELQRLFYTHLYRMFAMPMNATSTSGTYRGVDGAVHAAQGFTYY
DSWATWDDFRKFSVIAYIDPALYRDMVQSLVYLFADAEATGTGGGLGGFVHSVPTVRW
ERSSVVVADAIAKGFDGFDRLDEAYPALQRLVGQYSADELRRGYVAGNPGASVQRGYD
QYGLSVIADELGLTEEAETLREQASWPIEKLTKPGAWTAADGTQVGLLTPRAADGSWQ
SADHAKFEAAGLYQGTLWQYHWYDAYDMDALVEAMGGHEAARLGMRHMFGEHAPDDGK
AMLHSNANEIDLQAPYLFNYTGEPSLTQKWARAIYTKETWNRYIATGSSSAVPSGGGE
FTPPLKTKVYRLDPRGMLPTMDNDAGTMSTMFVAAAVGLFPVTAGSSQFQVGSPFFDS
TTITYDDGSAFTVTADGVSEDAFYVQSATLDGATFGNTWVDYATVVGGADLAFRMGEQ
PSDWGTDTAPAFSMSTATDEPAEGPRVSAEPTTVQTGDGGALDATVTLTLDGARLAAP
AGTDLVTSGAASVVGLPDGVTAAVTVASPTALTVSLTGTASADARFFVHLRDAALADG
VAAASLQGQGVSVRSPLRLSVASAERDALAALVDDAVLVRHGNYSSVTFDRFSTALTK
AQEALGDEAATSIALRFAADRLGAAADALDLTGGYRTLEAEQSEAWSGGELKNEANS
SSGNLGGVRSGSWVQYRDMTFETAAGDTPPRFLTVRYDTSFAPTDTPSTVRVHAGDVS
GPVVATVDLKGTSGWGKYTEVTAELGDVQALVDAQVVTFELLAPSGRSWVGNFDWFRF
SAEDPAAPGQPGESPTVTIEAEDWTASSGRGLKKESSTWTSGPVTNVGGTADGDWIAY
GEVDLGELPLGELSVHYVHNSNRSGNNSALSVYLDAFDPANPGEPFVTVPLPTTGSSW
TADGTATVVLPETVQGTHEVFVRLSTEPYADHPYVANLDSLTFAPGGPTSVVVESEAW
TSNSGRGLKNESSTWTSGPVTNVGGTADGDWLAYGEIDLGSAALDQLSVHYVHNSNRS
GRNSALSVYLDAFDPANPGEPFVTVPLANTGSSWTTDGTAVVDLPSTVRGKHQVWVRL
STEAYADHPYVANLDSMRFFTDAYDVEVPPTDTAALAAVVDAAGTPEAEIARYGRIDA
RVFTRELAAARSVLADAGATQAQADERARRLGLATDQLVPAERRRLENLVASAEALTD
EGYSPESWQAFRTALAAATGTLDDAAASDEALHDARLALQGAVDALEEPADVVLVEVE
VSPRCLAGKPYVAVRAVNVSDAAVDVELASSLGTRSFVGVAPGASAYQSFAARSATGD
LDVTVTATGADGTQTVEQVVTVPSCS (SEQ ID NO:4)

FIG. 2C

MYSHFNNEPVAKRVNNLFTDRLRQFTSDGEYRSLNLPAFYERERLDGKNHVAIETYAVSD
LRRPLFKDALKEADGHWKPAKKGSEYGPSWATHWFKIQVCVPPEWKKNYYKKGDLVVFNW
NLNCEGLVFSESGEALIGLSGEERREWPIPDNWFDGKCHTFYIEASCNGMFGNATGSSIQ
PPSDNRYFRLDSADLVVINSEARHLFVDFWIIGDAAREFPGDSWQRGKALDVANKIMDAF
DPENPDESIAEGRKLAKEYLGDTTKAYKQQLPFADGLVYALGNCHIDTAWLWPFAETRRK
AGRSWASQLELIDKYPEYVFVASQAQQFKWLKEDYPDLFAKIQKQAKKGRFLPVGGAWTE
CDTNLPSGESLLRQFLLGQRFFLEHFGSLSDTFWLPDTFGYSAQVPQLCRLAGMDRFLTQ
KLSWNNINSFPNSTFNWVALDGSQVLCHMPPNNTYTSMANFGDVSRTQKQNKNLDTTRNS
LMLYGHGDGGGGPTAEMLEKLRRCRGVSNTVGELPPVIQGQSVTDFYNELLDQTNNGKDL
VTWVGELYFEFHRGTYTSQAQTKKGNRVSENLLHDVELLATLASIRDSSYKYPFAQLESL
WEDVCLCQFHDVLPGSCIEMVYKDVKKIHGRVIDTASHLIDKAASALGLSGHPSKDSFDC
TPVALNTMPWSRTEVVAVPQPHWDATVELAEGVEIQEDSGNALVMMSESGPVVTTQSVDL
FKSEDAYILENSQVKVTICKDDGTLTSIYDKENDRRVLSGTGNRLVLFDDQPLSWQAWDT
EVFSLGKKQYIGAENVTRHSIVSSGPLRSTVAFTYEFNKSVVTTEISLDANSPLVTFNTR
ADWHETCKFLKVEFPVDVHSESASYESQFGVVKRPTHYNTSWDVAKFEVCCHKFADLSEL
DYGVSILNDCKYGFATHGNLMRLSLLRAPKAPDAHADMGHHEFKYGVLAHKGPLGATTVR
AAYNFNNPLRVKYVGLSEVSTKQAFSLKGPANLVLSQVKRAEVDRSKKSTNVILRVYEAL
GGRTRGKLVIDLPNVVSVTKTCALEYSKEKQVVAKSEGVTSVDISLRAFEVATYKVELA
(SEQ ID NO:5)

FIG. 6

```
  1 mhlpslslsl talaiaspsa ayphfgssqp vlhsssdttq sradaikaaf shawdgylqy
 61 afphdelhpv sngygdsrng wgasavdals tavimrnati vngildhvgk idysktnttv
121 slfettiryl ggmisgydil kgpvsdlvqn sskidviltq skniadvikf afdtpsgvpy
181 nnlnitsggn dgaktnglav tgtlalewtr lsdltgdtty adlsqkaesy llnpqpksae
241 pfpglvgsni nsngqftda qvswnggdds yyeylikmyv ydpkrfglyk drwvaaaqst
301 mqhlashpss rpdltflasy nngtlglssq hitcfdggsf llggtvlnrt dfinfgldlv
361 sgchdtynst ltgigpesfs wdtsdipssq qslyekagfy itsgayiirp eviesfyyaw
421 rvtggetyrd wiwsafsavn dycrtssgfs gltdvnaang gsrydnqesf lfaevmkysy
481 mafaedaawq vqpgsgnqfv fnteahpvrv sst (SEQ ID NO: 6)
```

MTRPLPPGRAVARSGSGRARPLGLVLAAALAVPLGVPLAAPAGALAAAPAAAAEPGDFSSSFESGDPAALPTT
VAERDGAPWQANVGSFTAGLPGSVLGQLKGVTASAQNLPNEGAANLADGSSGTKWLAFASTGWVRYEFAEPVS
FVAYTMTSGDDAAGRDPKTWTVEGSNDGSTWAALDRRTDEDFPNRQQTRTFELEAPTAAYTYLRLNVTANSGD
SIVQLAGWDLSADLSAGPSAAPMTKVGTGPRVSFTNKAGVGFESGLHSLRYDGSHLADGETYATNVLYDDVDV
VVGEDTRLSYTIFPELLDDLQYPSTYAAVDVLFTDGTYLSDLGARDAHETVATAQAQEGKILYADQWNSVRV
DLGDVAEGKTVDQVLLGYDNPGGHAGTKFAGWLDDVEITAEPATIDGSSLANYVDTRRGTLASGSFSRGNNIP
ATATPNGENFWTPYTNASSQSWLYEYHKANNANNKPVLQGFGISHEPSPWMGDRNQLTFLPSTASGTPDATLS
TRGLEFDHADETARPDYGVTFTNGSAIEATPTDHGAVLRFSYPGAKGHVLVDKVDGSSKLTYDQATGTISGW
VENGSGLSVGRTRMFVAGTFDRSPTAVGTAAGNRADARFATFETSSDKTVELRVATSFISLDQARKNLDLEVT
GKTFTEVKAAAAQAWNDRLGVIEVEGASEDQLVTLYSNLYRINLYPNSQFENTGTAQEPVYRYASPVSATTGS
ATDTQTNAKIVDGKIYVNNGFWDTYRTAWPAYSLLYPELAAELVDGFVQQYRDGGWIARWSSPGYADLMTGTS
SDVAFADAYLKGSLPTGTALEAYDAALRNATVAPPSNAVGRKGLQTSPFLGFTPESTHESVSWGLEGLVNDFG
IGNMAAALAEDPATPEERRETLREESAYFLERATHYVELFDPEVDFFVPRHEDGTWAVDPETYDPEAWGGGYT
ETNGWNFAFHAPQDGQGLANLYGGKQGLEDKLDEFFSTPEKGAGNGGIHEQREARDVRMGQWGMSNQVSHHIP
WLYDAAGAPSKAQEKVREVTRRLFVGSEIGQGYPGDEDNGEMSSWWIFASLGFYPLQVGSDQYAVGSPLFDKA
TVHLPDGDLVVNAENNSVDNVYVQSLAVDGEARTSTSLSQADLSGGTTLDFVMGPEPSDWGTGEDDAPPSLTE
GDEPPTPVQDATTAGLGTTTVADGDATTSAAALTDNTSGTRTFATTPSITWAGNGIRPTVGSYTLTSGASG
TASPSAWTLEGSDDGETWTTLDERSGEQFRWALQTRPFTVAEPTAFARYRVTVATSGSGALSLAEVELLADP
KESGAEELTLSAAPDRDGVTGREVSGSFATLTGVEGDVAALDVQVAFGDSEPVAGTLRAGAFGGYAVDAAHT
WTAPGVYPVTVTVSGEGIETVSASSYVSVSLLREGSLLAAYDNVCIGDAGTTVGSCDGQGVFFDRAQLAAKGF
VQGERATVPGTDLAFDVPAVPAGQPDNATGDGQTIELDVPADAEQLSVIGTEKNQQATGTLTFDDGSTQPI
DLSFGDWSGAARNPVFGNIPVAVTDSRLRGGSPQTGTPAAFFATAPITLPEGKRPVSLTLPDQPGELSRDGRI
HVVAVAHDGTFAEHPALEVTAAEGVTLAVGQTSDVALAQVAGGREGADLRAAVTWGDGSDVAAGAVTDGSVSG
SHAYTAAGTYTAYVVVDDGWTSQVVEVPVTVEAEPALAVDVTVSTRCLAGKAYVAVRAENGEDVPLAIRLVT
PFGTKEVAAVAPGANAYSFATRVTAVEAGTVTVEATRGTGDEEVTASIQADYAAVTCG  (SEQ ID NO:7)

MQSIKRTLLLLGAILPAVLGAPVQETRRAAEKLPGKYIVTFKPGIDEAK
IQEHTTWATNIHQRSLERRGATGGDLPVGIERNYKINKFAAYAGSFDDA
TIEEIRKNEDVAYVEEDQIYYLDGLTTQKSAPWGLGSISHKGQQSTDYI
YDTSAGEGTYAYVVDSGVNVDHEEFEGRASKAYNAAGGQHVDSIGHGTH
VSGTIAGKTYGIAKKASILSVKVFQGESSSTSVILDGFNWAANDIVSKK
RTSKAAINMSLGGGYSKAFNDAVENAFEQGVLSVVAAGNENSDAGQTSP
ASAPDAITVAAIQKSNNRASFSNFGKVVDVFAPGQDILSAWIGSSSATN
TISGTSMATPHIVGLSLYLAALENLDGPAAVTKRIKELATKDVVKDVKG
SPNLLAYNGNA (SEQ ID NO:9)

FIG. 9

GGATCCATGCAGTCCATTAAGCGAACTCTGCTGCTGCTGGGAGCCATTCT
GCCCGCCGTGCTGGGAGCCCCCGTTCAGGAGACCCGACGAGCCGCCGAGA
AGCTCCCCGGCAAGTACATTGTCACCTTCAAGCCTGGTATCGACGAGGCT
AAGATTCAGGAGCACACCACTTGGGCCACCAACATCCATCAGCGATCCCT
CGAGCGACGAGGAGCCACCGGCGGTGACCTGCCTGTGGGAATCGAGCGAA
ACTACAAGATTAACAAGTTCGCCGCTTACGCTGGATCTTTTGACGATGCC
ACCATCGAGGAGATTCGAAAGAACGAGGACGTCGCTTACGTGGAGGAAGA
CCAGATCTACTACCTCGATGGTCTGACCACTCAGAAGTCCGCTCCTTGGG
GCCTGGGCTCCATCTCTCACAAGGGACAGCAGTCGACTGACTACATCTAC
GATACCTCCGCTGGCGAGGGTACTTACGCCTACGTCGTGGACTCCGGTGT
TAACGTCGATCACGAGGAGTTTGAGGGACGAGCCTCTAAGGCTTACAACG
CCGCTGGAGGCCAGCATGTGGACTCTATCGGACACGGCACCCATGTTTCG
GGTACTATTGCCGGAAAGACCTACGGCATCGCCAAGAAGGCTTCTATTCT
CTCGGTGAAGGTTTTCCAGGGAGAGTCCTCTTCGACCTCTGTCATCCTGG
ACGGCTTTAACTGGGCCGCTAACGATATTGTGTCTAAGAAGCGAACCTCG
AAGGCCGCTATCAACATGTCCCTCGGTGGAGGCTACTCTAAGGCCTTCAA
CGACGCTGTTGAGAACGCCTTTGAGCAGGGTGTCCTGTCTGTTGTGGCTG
CTGGTAACGAGAACTCTGACGCTGGACAGACCTCCCCTGCTTCTGCTCCT
GATGCCATCACTGTGGCCGCTATTCAGAAGTCCAACAACCGAGCTTCGTT
CTCCAACTTTGGCAAGGTGGTTGACGTTTTCGCCCCGGACAGGATATCC
TCTCTGCTTGGATTGGCTCCTCTTCGGCCACCAACACTATCTCGGGCACC
TCCATGGCCACTCCCCACATTGTCGGTCTGTCCCTCTACCTGGCTGCTCT
GGAGAACCTGGACGGACCTGCCGCTGTTACCAAGCGAATCAAGGAGCTGG
CTACTAAGGACGTCGTGAAGGATGTCAAGGGTTCTCCTAACCTGCTCGCC
TACAACGGCAACGCTTCTGGCGGCGGAGGA*CATCACCACCATCACCATCA
CCACCATCATTGATAACCTAGG* (SEQ ID NO:10)

FIG. 10

SEQUENCE LISTING

<160> NUMBER OF SEQ ID NOS: 12

<210> SEQ ID NO 1
<211> LENGTH: 898
<212> TYPE: PRT
<213> ORGANISM: Homo sapiens

<400> SEQUENCE: 1

```
Ala Ala Gln Gln Gly Ala Ser Arg Pro Gly Pro Arg Asp Ala Gln Ala
1               5                   10                  15

His Pro Gly Arg Pro Arg Ala Val Pro Thr Gln Cys Asp Val Pro Pro
            20                  25                  30

Asn Ser Arg Phe Asp Cys Ala Pro Asp Lys Ala Ile Thr Gln Glu Gln
        35                  40                  45

Cys Glu Ala Arg Gly Cys Cys Tyr Ile Pro Ala Lys Gln Gly Leu Gln
    50                  55                  60

Gly Ala Gln Met Gly Gln Pro Trp Cys Phe Phe Pro Pro Ser Tyr Pro
65                  70                  75                  80

Ser Tyr Lys Leu Glu Asn Leu Ser Ser Ser Glu Met Gly Tyr Thr Ala
                85                  90                  95

Thr Leu Thr Arg Thr Thr Pro Thr Phe Phe Pro Lys Asp Ile Leu Thr
            100                 105                 110

Leu Arg Leu Asp Val Met Met Glu Thr Glu Asn Arg Leu His Phe Thr
        115                 120                 125

Ile Lys Asp Pro Ala Asn Arg Arg Tyr Glu Val Pro Leu Glu Thr Pro
    130                 135                 140

His Val His Ser Arg Ala Pro Ser Pro Leu Tyr Ser Val Glu Phe Ser
145                 150                 155                 160

Glu Glu Pro Phe Gly Val Ile Val Arg Arg Gln Leu Asp Gly Arg Val
                165                 170                 175

Leu Leu Asn Thr Thr Val Ala Pro Leu Phe Phe Ala Asp Gln Phe Leu
            180                 185                 190

Gln Leu Ser Thr Ser Leu Pro Ser Gln Tyr Ile Thr Gly Leu Ala Glu
        195                 200                 205

His Leu Ser Pro Leu Met Leu Ser Thr Ser Trp Thr Arg Ile Thr Leu
    210                 215                 220

Trp Asn Arg Asp Leu Ala Pro Thr Pro Gly Ala Asn Leu Tyr Gly Ser
225                 230                 235                 240

His Pro Phe Tyr Leu Ala Leu Glu Asp Gly Gly Ser Ala His Gly Val
                245                 250                 255

Phe Leu Leu Asn Ser Asn Ala Met Asp Val Val Leu Gln Pro Ser Pro
            260                 265                 270

Ala Leu Ser Trp Arg Ser Thr Gly Gly Ile Leu Asp Val Tyr Ile Phe
        275                 280                 285

Leu Gly Pro Glu Pro Lys Ser Val Val Gln Gln Tyr Leu Asp Val Val
    290                 295                 300

Gly Tyr Pro Phe Met Pro Pro Tyr Trp Gly Leu Gly Phe His Leu Cys
305                 310                 315                 320

Arg Trp Gly Tyr Ser Ser Thr Ala Ile Thr Arg Gln Val Val Glu Asn
                325                 330                 335

Met Thr Arg Ala His Phe Pro Leu Asp Val Gln Trp Asn Asp Leu Asp
            340                 345                 350

Tyr Met Asp Ser Arg Arg Asp Phe Thr Phe Asn Lys Asp Gly Phe Arg
        355                 360                 365
```

-continued

```
Asp Phe Pro Ala Met Val Gln Glu Leu His Gln Gly Gly Arg Arg Tyr
    370                 375                 380

Met Met Ile Val Asp Pro Ala Ile Ser Ser Gly Pro Ala Gly Ser
385                 390                 395                 400

Tyr Arg Pro Tyr Asp Glu Gly Leu Arg Arg Gly Val Phe Ile Thr Asn
                405                 410                 415

Glu Thr Gly Gln Pro Leu Ile Gly Lys Val Trp Pro Gly Ser Thr Ala
                420                 425                 430

Phe Pro Asp Phe Thr Asn Pro Thr Ala Leu Ala Trp Trp Glu Asp Met
            435                 440                 445

Val Ala Glu Phe His Asp Gln Val Pro Phe Asp Gly Met Trp Ile Asp
    450                 455                 460

Met Asn Glu Pro Ser Asn Phe Ile Arg Gly Ser Glu Asp Gly Cys Pro
465                 470                 475                 480

Asn Asn Glu Leu Glu Asn Pro Pro Tyr Val Pro Gly Val Val Gly Gly
                485                 490                 495

Thr Leu Gln Ala Ala Thr Ile Cys Ala Ser Ser His Gln Phe Leu Ser
                500                 505                 510

Thr His Tyr Asn Leu His Asn Leu Tyr Gly Leu Thr Glu Ala Ile Ala
            515                 520                 525

Ser His Arg Ala Leu Val Lys Ala Arg Gly Thr Arg Pro Phe Val Ile
    530                 535                 540

Ser Arg Ser Thr Phe Ala Gly His Gly Arg Tyr Ala Gly His Trp Thr
545                 550                 555                 560

Gly Asp Val Trp Ser Ser Trp Glu Gln Leu Ala Ser Ser Val Pro Glu
                565                 570                 575

Ile Leu Gln Phe Asn Leu Leu Gly Val Pro Leu Val Gly Ala Asp Val
                580                 585                 590

Cys Gly Phe Leu Gly Asn Thr Ser Glu Glu Leu Cys Val Arg Trp Thr
            595                 600                 605

Gln Leu Gly Ala Phe Tyr Pro Phe Met Arg Asn His Asn Ser Leu Leu
    610                 615                 620

Ser Leu Pro Gln Glu Pro Tyr Ser Phe Ser Glu Pro Ala Gln Gln Ala
625                 630                 635                 640

Met Arg Lys Ala Leu Thr Leu Arg Tyr Ala Leu Leu Pro His Leu Tyr
                645                 650                 655

Thr Leu Phe His Gln Ala His Val Ala Gly Glu Thr Val Ala Arg Pro
            660                 665                 670

Leu Phe Leu Glu Phe Pro Lys Asp Ser Ser Thr Trp Thr Val Asp His
    675                 680                 685

Gln Leu Leu Trp Gly Glu Ala Leu Leu Ile Thr Pro Val Leu Gln Ala
    690                 695                 700

Gly Lys Ala Glu Val Thr Gly Tyr Phe Pro Leu Gly Thr Trp Tyr Asp
705                 710                 715                 720

Leu Gln Thr Val Pro Val Glu Ala Leu Gly Ser Leu Pro Pro Pro
                725                 730                 735

Ala Ala Pro Arg Glu Pro Ala Ile His Ser Glu Gly Gln Trp Val Thr
            740                 745                 750

Leu Pro Ala Pro Leu Asp Thr Ile Asn Val His Leu Arg Ala Gly Tyr
            755                 760                 765

Ile Ile Pro Leu Gln Gly Pro Gly Leu Thr Thr Thr Glu Ser Arg Gln
    770                 775                 780

Gln Pro Met Ala Leu Ala Val Ala Leu Thr Lys Gly Gly Glu Ala Arg
```

```
                785               790               795             800
Gly Glu Leu Phe Trp Asp Asp Gly Glu Ser Leu Glu Val Leu Glu Arg
                    805                     810                 815

Gly Ala Tyr Thr Gln Val Ile Phe Leu Ala Arg Asn Asn Thr Ile Val
                820                 825                 830

Asn Glu Leu Val Arg Val Thr Ser Glu Gly Ala Gly Leu Gln Leu Gln
                835                 840                 845

Lys Val Thr Val Leu Gly Val Ala Thr Ala Pro Gln Gln Val Leu Ser
850                 855                 860

Asn Gly Val Pro Val Ser Asn Phe Thr Tyr Ser Pro Asp Thr Lys Val
865                 870                 875                 880

Leu Asp Ile Cys Val Ser Leu Leu Met Gly Glu Gln Phe Leu Val Ser
                885                 890                 895

Trp Cys

<210> SEQ ID NO 2
<211> LENGTH: 5060
<212> TYPE: DNA
<213> ORGANISM: Cellulosimicrobium cellulans

<400> SEQUENCE: 2
```

| | | | | |
|---|---|---|---|---|
| atgaaaaaga | tttggctggc | gctggctggt | ttagttttag | cgtttagcgc atcggccggc | 60 |
| catcaccatc | atcaccacgt | ggggcccggc | tcggacgaag | tggatgcacc ggaacctccg | 120 |
| agcgcagatt | atgcaagcct | ggttgatgtt | tttgttggca | ccgaaggtga ttttggtaat | 180 |
| gatatgcctg | cagcacaggc | accgaatggt | ctggcaaaag | ttaatccgcg taccacaccg | 240 |
| ggtcgtaata | taccggttat | ggactatgcc | cagagcaaaa | ttagcggttt acccatacc | 300 |
| aatctggatg | tgttggtgg | tagcggtggt | ggtggtgatc | tgctggttgt ccgaccagc | 360 |
| ggtagctata | ccgcacgtcc | gggtacaggc | acctatgcac | atccgtttag ccatgatgat | 420 |
| gaagatgcag | tccgggtttt | tatagcgtt | ggtctgggta | tgttgcagg caccgatggt | 480 |
| gcaattaccg | gtgctccggg | tacaattgaa | gcagaagttg | cagcagcaac ccgtagcggt | 540 |
| gttcatcgtt | atgcatttcc | ggcaggtagc | accccgagcc | tggttgttga tctggaaacc | 600 |
| aataatacca | gccgtcgtag | cagcagcgtt | caggttgaaa | cccgtgcaga tggcaccgtt | 660 |
| gaactgagcg | tcaggttac | ggctatttt | tataatgcag | cctataccct gtattatacc | 720 |
| gcacgcaccc | tgcagcctgc | aaccgttcag | acctggggtg | atgatgatcg tctggttgat | 780 |
| gcaaccgcac | aggatggtgt | tgataccggt | gcaattctga | cctttgatcc ggcagatgcc | 840 |
| ggtgaaattg | gtctgcaggt | taccctgtct | ccggttagcg | ttgaacaggc acgtattgat | 900 |
| cagcaggttg | aactgggtga | tctgagcttt | gatgcaattc | gtgatcgtac ccgtgcagaa | 960 |
| tggaatgcaa | ccctgggtcg | tgttgcaatt | gatgcaagca | ccgcaaccga tccgaccggt | 1020 |
| gaactgcagc | gtctgtttta | tacccatctg | tatcgcatgt | ttgcaatgcc gatgaatgca | 1080 |
| accagcacca | gcggcaccta | tcgtggtgtt | gatggtgcag | ttcatgcagc acagggcttt | 1140 |
| acctattatg | atagctgggc | aacctgggat | gattttcgca | atttagcgt gattgcctat | 1200 |
| attgatccgg | cactgtatcg | tgatatggtt | cagagcctgg | tttacctgtt tgcagatgca | 1260 |
| gaagcaaccg | gtacaggcgg | tggtctgggt | ggttttgttc | atagcgttcc gaccgttcgt | 1320 |
| tgggaacgta | gcagcgttgt | tgttgcagat | gcaattgcca | aaggctttga tggttttgat | 1380 |
| cgtctggatg | aagcatatcc | ggcactgcag | cgcctggttg | tcagtatag cgcagatgaa | 1440 |
| ctgcgtcgtg | gttatgttgc | aggtaatccg | ggtgcaagcg | ttcagcgtgg ttatgatcag | 1500 |

```
tatggtctga gcgttattgc cgatgaactg ggtctgaccg aagaagcaga acccctgcgc    1560
gaacaggcaa gctggccgat tgaaaaactg accaaaccgg gtgcatggac cgcagcagat    1620
ggtacacagg ttggtctgct gacaccgcgt gcagccgatg gtagctggca gagcgcagat    1680
catgccaaat ttgaagcagc aggtctgtat cagggcaccc tgtggcagta tcattggtat    1740
gatgcctatg atatggatgc actggttgaa gcaatgggtg gtcatgaagc agcccgtctg    1800
ggtatgcgtc atatgtttgg tgaacatgca ccggatgatg gtaaagcaat gctgcatagc    1860
aatgccaatg aaattgatct gcaggcaccg tacctgttta attataccgg tgaaccgagc    1920
ctgacccaga atgggcacg tgcaatttat accaaagaaa cctggaatcg ctatattgca    1980
accggtagca gctctgcagt tccgtcaggt ggtggtgaat ttacacctcc gctgaaaacc    2040
aaagtttatc gtctggaccc tcgtggtatg ctgccgacca tggataatga tgcaggtaca    2100
atgagcacca tgtttgttgc agcagccgtt ggtctgtttc cggttaccgc aggtagcagc    2160
cagtttcagg ttggtagccc gttttttgat agcaccacca ttacctatga tgatggtagc    2220
gcatttaccg ttaccgcaga tggtgttagc gaagatgcct tttatgttca gagcgcaacc    2280
ctggatggtg caacctttgg taatacctgg gttgattatg caaccgttgt tggtggtgca    2340
gatctggcat ttcgtatggg tgaacagccg agcgattggg gcaccgatac cgcaccggca    2400
tttagcatga gcaccgccac cgatgaaccg gcagaaggtc ctcgcgttag cgcagaaccg    2460
accaccgtgc agaccggtga tggtggtgca ctggatgcaa ccgttaccct gacactggat    2520
ggcgcacgtc tggcagcacc ggcaggtaca gatctggtta ccagcggtgc agcaagcgtt    2580
gttggtctgc cggatggtgt taccgcagca gttaccgttg caagcccgac cgcactgacc    2640
gttagcctga ccggcaccgc atcagcagat gcacgttttt ttgtgcatct gcgtgatgca    2700
gcactggccg atggtgttgc agccgcaagc ctgcagggtc agggtgttag cgttcgttct    2760
ccgctgcgtc tgagcgttgc aagcgcagaa cgtgatgcac tggcagcact ggttgatgat    2820
gccgttctgg ttcgtcatgg taattatagc agcgttacct ttgatcgttt agcaccgctc    2880
tgacaaaagc acaggaagca ctgggcgacg aagcagcaac cagcattgca ctgcgttttg    2940
cagcagatcg tctgggtgca gcagcagatg cactggatct gaccggtggt ggttatcgta    3000
ccctggaagc agaacagagc gaagcatggt ctggtggtga actgaaaaat gaagccaata    3060
gcagcagcgg taatctgggt ggtgttcgta gcggtagctg ggttcagtat cgcgatatga    3120
cctttgaaac cgcagccggt gatacacctc gcgttttct gaccgttcgt tatgatacca    3180
gctttgcacc gaccgatacc ccgagcaccg ttcgtgttca tgccggtgat gtttctggtc    3240
cggttgttgc aaccgttgat ctgaaaggca ccagcggttg gggtaaatat accgaagtta    3300
ccgcagaact gggtgatgtt caggccctgg ttgatgccca ggttgttacc tttgaactgc    3360
tggcaccgag cggtcgtagc tgggttggta atttgattg gtttcgcttt agcgcagaag    3420
atccggcagc accgggtcag cctggtgaaa gcccgaccgt taccattgaa gccgaagatt    3480
ggaccgcaag cagcggtcgt ggtctgaaaa agaaagcag cacctggacc agcggtccgg    3540
tgaccaatgt tggtggtaca gcagatggtg attggattgc ctatggtgaa gttgatctgg    3600
gtgaactgcc gctgggcgaa ctgagcgttc attatgtgca taatagcaat cgcagcggta    3660
ataatagcgc actgagcgtt tatctggatg catttgatcc ggctaatccg ggtgaaccgt    3720 tgttaccgt tccgctgccg accaccggta gcagttggac cgcagatggc acagccaccg    3780
ttgttctgcc ggaaaccgtg cagggcaccc atgaagtttt tgttcgtctg agcaccgaac    3840
```

-continued

```
cgtatgcaga tcatccgtat gttgcaaatc tggatagcct gaccttgca ccgggtggtc     3900
cgaccagcgt tgtggttgaa agcgaagcct ggaccagcaa ttctggtcgt ggcctgaaaa     3960
atgaatcttc tacctggacc tctggtccgg ttacaaatgt gggtggcacc gctgatggcg     4020
attggctggc atatgcgaaa ttgatctgg gcagcgcagc actggatcag ctgtctgtgc     4080
attatgttca taattctaat cgctctggtc gtaattctgc actgtctgtg tatctggatg     4140
cctttgatcc ggcaaatccg ggtgaaccgt tgtgacagt gccgctggca ataccggta      4200
gctcttggac caccgatggt actgcagttg tggatctgcc gtctaccgtt cgtggtaaac     4260
atcaggtttg ggttcgtctg tctaccgaag catatgccga tcatccgtat gtggccaatc     4320
tggattctat gcgctttttt accgatgcat atgatgttga agttcctccg accgatacag     4380
cagcactggc agccgttgtt gatgcagcag gtacaccgga agcagaaatt gcacgttatg     4440
gtcgtattga tgcccgtgtt tttacccgtg aactggcagc agcacgtagc gttctggccg     4500
atgccggtgc aacacaggca caggcagatg aacgtgctcg tcgtctgggt ctggcaaccg     4560
atcagctggt tccggcagaa cgtcgtcgtc tggaaaatct ggttgccagc gcagaagcac     4620
tgaccgacga aggttattct ccggaaagct ggcaggcatt tcgtaccgca ctggctgctg     4680
caaccggcac cctggatgat gcagcagcat ctgatgaagc actgcatgat gcacgtctgg     4740
cgctgcaggg tgcagttgat gcactggaag aaccggcaga tgttgttctg gttgaagttg     4800
aagtttctcc gcgttgtctg gcaggtaaac cgtatgttgc cgttcgtgca gttaatgttt     4860
ctgatgcagc cgttgatgtt gaactggcaa gctctctggg cacccgtagc tttgttggtg     4920
tggcaccggg tgcgagcgca tatcagagct ttgcagcccg tagcgcaacc ggtgatctgg     4980
atgttaccgt gaccgcaacc ggtgcagatg gtactcagac cgttgaacag gttgtgaccg     5040
ttccgagctg tagctaataa                                                 5060
```

<210> SEQ ID NO 3
<211> LENGTH: 1665
<212> TYPE: PRT
<213> ORGANISM: Cellulosimicrobium cellulans

<400> SEQUENCE: 3

```
Ala Leu Ala Val Val Gly Leu Ala Pro Ala Thr Ala Ala Ser Ala Ala
 1               5                  10                  15

Pro Glu Pro Pro Ser Ala Asp Tyr Ala Ser Leu Val Asp Val Phe Val
                20                  25                  30

Gly Thr Glu Gly Asp Phe Gly Asn Asp Met Pro Ala Ala Gln Ala Pro
            35                  40                  45

Asn Gly Leu Ala Lys Val Asn Pro Arg Thr Thr Pro Gly Arg Asn Asn
        50                  55                  60

Thr Gly Tyr Asp Tyr Ala Gln Ser Lys Ile Ser Gly Phe Thr His Thr
 65                  70                  75                  80

Asn Leu Asp Gly Val Gly Gly Ser Gly Gly Gly Asp Leu Leu Val
                85                  90                  95

Val Pro Thr Ser Gly Ser Tyr Thr Ala Arg Pro Gly Thr Gly Thr Tyr
            100                 105                 110

Ala His Pro Phe Ser His Asp Asp Glu Asp Ala Gly Pro Gly Phe Tyr
        115                 120                 125

Ser Val Gly Leu Gly Asn Val Ala Gly Thr Asp Gly Ala Ile Thr Gly
    130                 135                 140

Ala Pro Gly Thr Ile Glu Ala Glu Val Ala Ala Ala Thr Arg Ser Gly
145                 150                 155                 160
```

```
Val His Arg Tyr Ala Phe Pro Ala Gly Ser Thr Pro Ser Leu Val Val
                165                 170                 175

Asp Leu Glu Thr Asn Asn Thr Ser Arg Arg Ser Ser Ser Val Gln Val
                180                 185                 190

Glu Thr Arg Ala Asp Gly Thr Val Glu Leu Ser Gly Gln Val Thr Gly
            195                 200                 205

Tyr Phe Tyr Asn Ala Ala Tyr Thr Leu Tyr Tyr Thr Ala Arg Thr Leu
        210                 215                 220

Gln Pro Ala Thr Val Gln Thr Trp Gly Asp Asp Arg Leu Val Asp
225                 230                 235                 240

Ala Thr Ala Gln Asp Gly Val Asp Thr Gly Ala Ile Leu Thr Phe Asp
                245                 250                 255

Pro Ala Asp Ala Gly Glu Ile Gly Leu Gln Val Thr Leu Ser Pro Val
                260                 265                 270

Ser Val Glu Gln Ala Arg Ile Asp Gln Gln Val Glu Leu Gly Asp Leu
                275                 280                 285

Ser Phe Asp Ala Ile Arg Asp Arg Thr Arg Ala Glu Trp Asn Ala Thr
        290                 295                 300

Leu Gly Arg Val Ala Ile Asp Ala Ser Thr Ala Thr Asp Pro Thr Gly
305                 310                 315                 320

Glu Leu Gln Arg Leu Phe Tyr Thr His Leu Tyr Arg Met Phe Ala Met
                325                 330                 335

Pro Met Asn Ala Thr Ser Thr Ser Gly Thr Tyr Arg Gly Val Asp Gly
                340                 345                 350

Ala Val His Ala Ala Gln Gly Phe Thr Tyr Tyr Asp Ser Trp Ala Thr
                355                 360                 365

Trp Asp Asp Phe Arg Lys Phe Ser Val Ile Ala Tyr Ile Asp Pro Ala
        370                 375                 380

Leu Tyr Arg Asp Met Val Gln Ser Leu Val Tyr Leu Phe Ala Asp Ala
385                 390                 395                 400

Glu Ala Thr Gly Thr Gly Gly Leu Gly Gly Phe Val His Ser Val
                405                 410                 415

Pro Thr Val Arg Trp Glu Arg Ser Ser Val Val Ala Asp Ala Ile
                420                 425                 430

Ala Lys Gly Phe Asp Gly Phe Asp Arg Leu Asp Glu Ala Tyr Pro Ala
        435                 440                 445

Leu Gln Arg Leu Val Gly Gln Tyr Ser Ala Asp Glu Leu Arg Arg Gly
        450                 455                 460

Tyr Val Ala Gly Asn Pro Gly Ala Ser Val Gln Arg Gly Tyr Asp Gln
465                 470                 475                 480

Tyr Gly Leu Ser Val Ile Ala Asp Glu Leu Gly Leu Thr Glu Glu Ala
                485                 490                 495

Glu Thr Leu Arg Glu Gln Ala Ser Trp Pro Ile Glu Lys Leu Thr Lys
                500                 505                 510

Pro Gly Ala Trp Thr Ala Ala Asp Gly Thr Gln Val Gly Leu Leu Thr
                515                 520                 525

Pro Arg Ala Ala Asp Gly Ser Trp Gln Ser Ala Asp His Ala Lys Phe
                530                 535                 540

Glu Ala Ala Gly Leu Tyr Gln Gly Thr Leu Trp Gln Tyr His Trp Tyr
545                 550                 555                 560

Asp Ala Tyr Asp Met Asp Ala Leu Val Glu Ala Met Gly Gly His Glu
                565                 570                 575
```

-continued

```
Ala Ala Arg Leu Gly Met Arg His Met Phe Gly Glu His Ala Pro Asp
            580                 585                 590

Asp Gly Lys Ala Met Leu His Ser Asn Ala Asn Glu Ile Asp Leu Gln
        595                 600                 605

Ala Pro Tyr Leu Phe Asn Tyr Thr Gly Glu Pro Ser Leu Thr Gln Lys
    610                 615                 620

Trp Ala Arg Ala Ile Tyr Thr Lys Glu Thr Trp Asn Arg Tyr Ile Ala
625                 630                 635                 640

Thr Gly Ser Ser Ser Ala Val Pro Ser Gly Gly Glu Phe Thr Pro
                645                 650                 655

Pro Leu Lys Thr Lys Val Tyr Arg Leu Asp Pro Arg Gly Met Leu Pro
            660                 665                 670

Thr Met Asp Asn Asp Ala Gly Thr Met Ser Thr Met Phe Val Ala Ala
        675                 680                 685

Ala Val Gly Leu Phe Pro Val Thr Ala Gly Ser Ser Gln Phe Gln Val
    690                 695                 700

Gly Ser Pro Phe Phe Asp Ser Thr Ile Thr Tyr Asp Asp Gly Ser
705                 710                 715                 720

Ala Phe Thr Val Thr Ala Asp Gly Val Ser Glu Asp Ala Phe Tyr Val
                725                 730                 735

Gln Ser Ala Thr Leu Asp Gly Ala Thr Phe Gly Asn Thr Trp Val Asp
            740                 745                 750

Tyr Ala Thr Val Val Gly Gly Ala Asp Leu Ala Phe Arg Met Gly Glu
        755                 760                 765

Gln Pro Ser Asp Trp Gly Thr Asp Thr Ala Pro Ala Phe Ser Met Ser
    770                 775                 780

Thr Ala Thr Asp Glu Pro Ala Glu Gly Pro Arg Val Ser Ala Glu Pro
785                 790                 795                 800

Thr Thr Val Gln Thr Gly Asp Gly Gly Ala Leu Asp Ala Thr Val Thr
                805                 810                 815

Leu Thr Leu Asp Gly Ala Arg Leu Ala Ala Pro Ala Gly Thr Asp Leu
            820                 825                 830

Val Thr Ser Gly Ala Ala Ser Val Val Gly Leu Pro Asp Gly Val Thr
        835                 840                 845

Ala Ala Val Thr Val Ala Ser Pro Thr Ala Leu Thr Val Ser Leu Thr
    850                 855                 860

Gly Thr Ala Ser Ala Asp Ala Arg Phe Phe Val His Leu Arg Asp Ala
865                 870                 875                 880

Ala Leu Ala Asp Gly Val Ala Ala Ser Leu Gln Gly Gln Gly Val
                885                 890                 895

Ser Val Arg Ser Pro Leu Arg Leu Ser Val Ala Ser Ala Glu Arg Asp
            900                 905                 910

Ala Leu Ala Ala Leu Val Asp Asp Ala Val Leu Val Arg His Gly Asn
        915                 920                 925

Tyr Ser Ser Val Thr Phe Asp Arg Phe Ser Thr Ala Leu Thr Lys Ala
    930                 935                 940

Gln Glu Ala Leu Gly Asp Glu Ala Ala Thr Ser Ile Ala Leu Arg Phe
945                 950                 955                 960

Ala Ala Asp Arg Leu Gly Ala Ala Asp Ala Leu Asp Leu Thr Gly
                965                 970                 975

Gly Gly Tyr Arg Thr Leu Glu Ala Glu Gln Ser Glu Ala Trp Ser Gly
            980                 985                 990

Gly Glu Leu Lys Asn Glu Ala Asn  Ser Ser Ser Gly Asn  Leu Gly Gly
```

```
              995                 1000                1005
Val Arg Ser Gly Ser Trp Val Gln Tyr Arg Asp Met Thr Phe Glu
    1010                1015                1020

Thr Ala Ala Gly Asp Thr Pro Pro Arg Phe Leu Thr Val Arg Tyr
    1025                1030                1035

Asp Thr Ser Phe Ala Pro Thr Asp Thr Pro Ser Thr Val Arg Val
    1040                1045                1050

His Ala Gly Asp Val Ser Gly Pro Val Val Ala Thr Val Asp Leu
    1055                1060                1065

Lys Gly Thr Ser Gly Trp Gly Lys Tyr Thr Glu Val Thr Ala Glu
    1070                1075                1080

Leu Gly Asp Val Gln Ala Leu Val Asp Ala Gln Val Val Thr Phe
    1085                1090                1095

Glu Leu Leu Ala Pro Ser Gly Arg Ser Trp Val Gly Asn Phe Asp
    1100                1105                1110

Trp Phe Arg Phe Ser Ala Glu Asp Pro Ala Ala Pro Gly Gln Pro
    1115                1120                1125

Gly Glu Ser Pro Thr Val Thr Ile Glu Ala Glu Asp Trp Thr Ala
    1130                1135                1140

Ser Ser Gly Arg Gly Leu Lys Lys Glu Ser Ser Thr Trp Thr Ser
    1145                1150                1155

Gly Pro Val Thr Asn Val Gly Gly Thr Ala Asp Gly Asp Trp Ile
    1160                1165                1170

Ala Tyr Gly Glu Val Asp Leu Gly Glu Leu Pro Leu Gly Glu Leu
    1175                1180                1185

Ser Val His Tyr Val His Asn Ser Asn Arg Ser Gly Asn Asn Ser
    1190                1195                1200

Ala Leu Ser Val Tyr Leu Asp Ala Phe Asp Pro Ala Asn Pro Gly
    1205                1210                1215

Glu Pro Phe Val Thr Val Pro Leu Pro Thr Thr Gly Ser Ser Trp
    1220                1225                1230

Thr Ala Asp Gly Thr Ala Thr Val Val Leu Pro Glu Thr Val Gln
    1235                1240                1245

Gly Thr His Glu Val Phe Val Arg Leu Ser Thr Glu Pro Tyr Ala
    1250                1255                1260

Asp His Pro Tyr Val Ala Asn Leu Asp Ser Leu Thr Phe Ala Pro
    1265                1270                1275

Gly Gly Pro Thr Ser Val Val Val Glu Ser Glu Ala Trp Thr Ser
    1280                1285                1290

Asn Ser Gly Arg Gly Leu Lys Asn Glu Ser Ser Thr Trp Thr Ser
    1295                1300                1305

Gly Pro Val Thr Asn Val Gly Gly Thr Ala Asp Gly Asp Trp Leu
    1310                1315                1320

Ala Tyr Gly Glu Ile Asp Leu Gly Ser Ala Ala Leu Asp Gln Leu
    1325                1330                1335

Ser Val His Tyr Val His Asn Ser Asn Arg Ser Gly Arg Asn Ser
    1340                1345                1350

Ala Leu Ser Val Tyr Leu Asp Ala Phe Asp Pro Ala Asn Pro Gly
    1355                1360                1365

Glu Pro Phe Val Thr Val Pro Leu Ala Asn Thr Gly Ser Ser Trp
    1370                1375                1380

Thr Thr Asp Gly Thr Ala Val Val Asp Leu Pro Ser Thr Val Arg
    1385                1390                1395
```

Gly Lys His Gln Val Trp Val Arg Leu Ser Thr Glu Ala Tyr Ala
1400                1405                1410

Asp His Pro Tyr Val Ala Asn Leu Asp Ser Met Arg Phe Phe Thr
1415                1420                1425

Asp Ala Tyr Asp Val Glu Val Pro Pro Thr Asp Thr Ala Ala Leu
1430                1435                1440

Ala Ala Val Val Asp Ala Gly Thr Pro Glu Ala Glu Ile Ala
1445                1450                1455

Arg Tyr Gly Arg Ile Asp Ala Arg Val Phe Thr Arg Glu Leu Ala
1460                1465                1470

Ala Ala Arg Ser Val Leu Ala Asp Ala Gly Ala Thr Gln Ala Gln
1475                1480                1485

Ala Asp Glu Arg Ala Arg Arg Leu Gly Leu Ala Thr Asp Gln Leu
1490                1495                1500

Val Pro Ala Glu Arg Arg Arg Leu Glu Asn Leu Val Ala Ser Ala
1505                1510                1515

Glu Ala Leu Thr Asp Glu Gly Tyr Ser Pro Glu Ser Trp Gln Ala
1520                1525                1530

Phe Arg Thr Ala Leu Ala Ala Ala Thr Gly Thr Leu Asp Asp Ala
1535                1540                1545

Ala Ala Ser Asp Glu Ala Leu His Asp Ala Arg Leu Ala Leu Gln
1550                1555                1560

Gly Ala Val Asp Ala Leu Glu Glu Pro Ala Asp Val Val Leu Val
1565                1570                1575

Glu Val Glu Val Ser Pro Arg Cys Leu Ala Gly Lys Pro Tyr Val
1580                1585                1590

Ala Val Arg Ala Val Asn Val Ser Asp Ala Ala Val Asp Val Glu
1595                1600                1605

Leu Ala Ser Ser Leu Gly Thr Arg Ser Phe Val Gly Val Ala Pro
1610                1615                1620

Gly Ala Ser Ala Tyr Gln Ser Phe Ala Ala Arg Ser Ala Thr Gly
1625                1630                1635

Asp Leu Asp Val Thr Val Thr Ala Thr Gly Ala Asp Gly Thr Gln
1640                1645                1650

Thr Val Glu Gln Val Val Thr Val Pro Ser Cys Ser
1655                1660                1665

<210> SEQ ID NO 4
<211> LENGTH: 1650
<212> TYPE: PRT
<213> ORGANISM: Cellulosimicrobium cellulans

<400> SEQUENCE: 4

Ala Pro Glu Pro Pro Ser Ala Asp Tyr Ala Ser Leu Val Asp Val Phe
1               5                   10                  15

Val Gly Thr Glu Gly Asp Phe Gly Asn Asp Met Pro Ala Ala Gln Ala
                20                  25                  30

Pro Asn Gly Leu Ala Lys Val Asn Pro Arg Thr Thr Pro Gly Arg Asn
        35                  40                  45

Asn Thr Gly Tyr Asp Tyr Ala Gln Ser Lys Ile Ser Gly Phe Thr His
    50                  55                  60

Thr Asn Leu Asp Gly Val Gly Gly Ser Gly Gly Gly Asp Leu Leu
65                  70                  75                  80

Val Val Pro Thr Ser Gly Ser Tyr Thr Ala Arg Pro Gly Thr Gly Thr

```
                        85                  90                  95
Tyr Ala His Pro Phe Ser His Asp Asp Glu Asp Ala Gly Pro Gly Phe
                       100                 105                 110

Tyr Ser Val Gly Leu Gly Asn Val Ala Gly Thr Asp Gly Ala Ile Thr
            115                 120                 125

Gly Ala Pro Gly Thr Ile Glu Ala Glu Val Ala Ala Ala Thr Arg Ser
        130                 135                 140

Gly Val His Arg Tyr Ala Phe Pro Ala Gly Ser Thr Pro Ser Leu Val
145                 150                 155                 160

Val Asp Leu Glu Thr Asn Asn Thr Ser Arg Arg Ser Ser Ser Val Gln
                165                 170                 175

Val Glu Thr Arg Ala Asp Gly Thr Val Glu Leu Ser Gly Gln Val Thr
            180                 185                 190

Gly Tyr Phe Tyr Asn Ala Ala Tyr Thr Leu Tyr Thr Ala Arg Thr
        195                 200                 205

Leu Gln Pro Ala Thr Val Gln Thr Trp Gly Asp Asp Asp Arg Leu Val
        210                 215                 220

Asp Ala Thr Ala Gln Asp Gly Val Asp Thr Gly Ala Ile Leu Thr Phe
225                 230                 235                 240

Asp Pro Ala Asp Ala Gly Glu Ile Gly Leu Gln Val Thr Leu Ser Pro
                245                 250                 255

Val Ser Val Glu Gln Ala Arg Ile Asp Gln Gln Val Glu Leu Gly Asp
            260                 265                 270

Leu Ser Phe Asp Ala Ile Arg Asp Arg Thr Arg Ala Glu Trp Asn Ala
        275                 280                 285

Thr Leu Gly Arg Val Ala Ile Asp Ala Ser Thr Ala Thr Asp Pro Thr
290                 295                 300

Gly Glu Leu Gln Arg Leu Phe Tyr Thr His Leu Tyr Arg Met Phe Ala
305                 310                 315                 320

Met Pro Met Asn Ala Thr Ser Thr Ser Gly Thr Tyr Arg Gly Val Asp
                325                 330                 335

Gly Ala Val His Ala Ala Gln Gly Phe Thr Tyr Tyr Asp Ser Trp Ala
            340                 345                 350

Thr Trp Asp Asp Phe Arg Lys Phe Ser Val Ile Ala Tyr Ile Asp Pro
        355                 360                 365

Ala Leu Tyr Arg Asp Met Val Gln Ser Leu Val Tyr Leu Phe Ala Asp
        370                 375                 380

Ala Glu Ala Thr Gly Thr Gly Gly Leu Gly Gly Phe Val His Ser
385                 390                 395                 400

Val Pro Thr Val Arg Trp Glu Arg Ser Ser Val Val Ala Asp Ala
                405                 410                 415

Ile Ala Lys Gly Phe Asp Gly Phe Asp Arg Leu Asp Glu Ala Tyr Pro
            420                 425                 430

Ala Leu Gln Arg Leu Val Gly Gln Tyr Ser Ala Asp Glu Leu Arg Arg
        435                 440                 445

Gly Tyr Val Ala Gly Asn Pro Gly Ala Ser Val Gln Arg Gly Tyr Asp
        450                 455                 460

Gln Tyr Gly Leu Ser Val Ile Ala Asp Glu Leu Gly Leu Thr Glu Glu
465                 470                 475                 480

Ala Glu Thr Leu Arg Glu Gln Ala Ser Trp Pro Ile Glu Lys Leu Thr
                485                 490                 495

Lys Pro Gly Ala Trp Thr Ala Ala Asp Gly Thr Gln Val Gly Leu Leu
            500                 505                 510
```

```
Thr Pro Arg Ala Ala Asp Gly Ser Trp Gln Ser Ala Asp His Ala Lys
        515                 520                 525

Phe Glu Ala Ala Gly Leu Tyr Gln Gly Thr Leu Trp Gln Tyr His Trp
        530                 535                 540

Tyr Asp Ala Tyr Asp Met Asp Ala Leu Val Glu Ala Met Gly Gly His
545                 550                 555                 560

Glu Ala Ala Arg Leu Gly Met Arg His Met Phe Gly Glu His Ala Pro
                565                 570                 575

Asp Asp Gly Lys Ala Met Leu His Ser Asn Ala Asn Glu Ile Asp Leu
            580                 585                 590

Gln Ala Pro Tyr Leu Phe Asn Tyr Thr Gly Pro Ser Leu Thr Gln
        595                 600                 605

Lys Trp Ala Arg Ala Ile Tyr Thr Lys Glu Thr Trp Asn Arg Tyr Ile
        610                 615                 620

Ala Thr Gly Ser Ser Ala Val Pro Ser Gly Gly Glu Phe Thr
625                 630                 635                 640

Pro Pro Leu Lys Thr Lys Val Tyr Arg Leu Asp Pro Arg Gly Met Leu
                645                 650                 655

Pro Thr Met Asp Asn Asp Ala Gly Thr Met Ser Thr Met Phe Val Ala
            660                 665                 670

Ala Ala Val Gly Leu Phe Pro Val Thr Ala Gly Ser Ser Gln Phe Gln
        675                 680                 685

Val Gly Ser Pro Phe Phe Asp Ser Thr Thr Ile Thr Tyr Asp Asp Gly
        690                 695                 700

Ser Ala Phe Thr Val Thr Ala Asp Gly Val Ser Glu Ala Phe Tyr
705                 710                 715                 720

Val Gln Ser Ala Thr Leu Asp Gly Ala Thr Phe Gly Asn Thr Trp Val
                725                 730                 735

Asp Tyr Ala Thr Val Val Gly Gly Ala Asp Leu Ala Phe Arg Met Gly
            740                 745                 750

Glu Gln Pro Ser Asp Trp Gly Thr Asp Thr Ala Pro Ala Phe Ser Met
        755                 760                 765

Ser Thr Ala Thr Asp Glu Pro Ala Glu Gly Pro Arg Val Ser Ala Glu
        770                 775                 780

Pro Thr Thr Val Gln Thr Gly Asp Gly Gly Ala Leu Asp Ala Thr Val
785                 790                 795                 800

Thr Leu Thr Leu Asp Gly Ala Arg Leu Ala Ala Pro Ala Gly Thr Asp
                805                 810                 815

Leu Val Thr Ser Gly Ala Ala Ser Val Val Gly Leu Pro Asp Gly Val
            820                 825                 830

Thr Ala Ala Val Thr Val Ala Ser Pro Thr Ala Leu Thr Val Ser Leu
        835                 840                 845

Thr Gly Thr Ala Ser Ala Asp Ala Arg Phe Phe Val His Leu Arg Asp
        850                 855                 860

Ala Ala Leu Ala Asp Gly Val Ala Ala Ala Ser Leu Gln Gly Gln Gly
865                 870                 875                 880

Val Ser Val Arg Ser Pro Leu Arg Leu Ser Val Ala Ser Ala Glu Arg
                885                 890                 895

Asp Ala Leu Ala Ala Leu Val Asp Asp Ala Val Leu Val Arg His Gly
            900                 905                 910

Asn Tyr Ser Ser Val Thr Phe Asp Arg Phe Ser Thr Ala Leu Thr Lys
        915                 920                 925
```

```
Ala Gln Glu Ala Leu Gly Asp Glu Ala Ala Thr Ser Ile Ala Leu Arg
    930                 935                 940

Phe Ala Ala Asp Arg Leu Gly Ala Ala Asp Ala Leu Asp Leu Thr
945                 950                 955                 960

Gly Gly Gly Tyr Arg Thr Leu Glu Ala Glu Gln Ser Glu Ala Trp Ser
                965                 970                 975

Gly Gly Glu Leu Lys Asn Glu Ala Asn Ser Ser Ser Gly Asn Leu Gly
            980                 985                 990

Gly Val Arg Ser Gly Ser Trp Val Gln Tyr Arg Asp Met Thr Phe Glu
        995                 1000                1005

Thr Ala Ala Gly Asp Thr Pro Pro Arg Phe Leu Thr Val Arg Tyr
    1010                1015                1020

Asp Thr Ser Phe Ala Pro Thr Asp Thr Pro Ser Thr Val Arg Val
    1025                1030                1035

His Ala Gly Asp Val Ser Gly Pro Val Val Ala Thr Val Asp Leu
    1040                1045                1050

Lys Gly Thr Ser Gly Trp Gly Lys Tyr Thr Glu Val Thr Ala Glu
    1055                1060                1065

Leu Gly Asp Val Gln Ala Leu Val Asp Ala Gln Val Val Thr Phe
    1070                1075                1080

Glu Leu Leu Ala Pro Ser Gly Arg Ser Trp Val Gly Asn Phe Asp
    1085                1090                1095

Trp Phe Arg Phe Ser Ala Glu Asp Pro Ala Ala Pro Gly Gln Pro
    1100                1105                1110

Gly Glu Ser Pro Thr Val Thr Ile Glu Ala Glu Asp Trp Thr Ala
    1115                1120                1125

Ser Ser Gly Arg Gly Leu Lys Lys Glu Ser Ser Thr Trp Thr Ser
    1130                1135                1140

Gly Pro Val Thr Asn Val Gly Gly Thr Ala Asp Gly Asp Trp Ile
    1145                1150                1155

Ala Tyr Gly Glu Val Asp Leu Gly Glu Leu Pro Leu Gly Glu Leu
    1160                1165                1170

Ser Val His Tyr Val His Asn Ser Asn Arg Ser Gly Asn Asn Ser
    1175                1180                1185

Ala Leu Ser Val Tyr Leu Asp Ala Phe Asp Pro Ala Asn Pro Gly
    1190                1195                1200

Glu Pro Phe Val Thr Val Pro Leu Pro Thr Thr Gly Ser Ser Trp
    1205                1210                1215

Thr Ala Asp Gly Thr Ala Thr Val Val Leu Pro Glu Thr Val Gln
    1220                1225                1230

Gly Thr His Glu Val Phe Val Arg Leu Ser Thr Glu Pro Tyr Ala
    1235                1240                1245

Asp His Pro Tyr Val Ala Asn Leu Asp Ser Leu Thr Phe Ala Pro
    1250                1255                1260

Gly Gly Pro Thr Ser Val Val Glu Ser Glu Ala Trp Thr Ser
    1265                1270                1275

Asn Ser Gly Arg Gly Leu Lys Asn Glu Ser Ser Thr Trp Thr Ser
    1280                1285                1290

Gly Pro Val Thr Asn Val Gly Gly Thr Ala Asp Gly Asp Trp Leu
    1295                1300                1305

Ala Tyr Gly Glu Ile Asp Leu Gly Ser Ala Ala Leu Asp Gln Leu
    1310                1315                1320

Ser Val His Tyr Val His Asn Ser Asn Arg Ser Gly Arg Asn Ser
```

```
        1325                1330                1335

Ala Leu Ser Val Tyr Leu Asp Ala Phe Asp Pro Ala Asn Pro Gly
        1340                1345                1350

Glu Pro Phe Val Thr Val Pro Leu Ala Asn Thr Gly Ser Ser Trp
    1355                1360                1365

Thr Thr Asp Gly Thr Ala Val Val Asp Leu Pro Ser Thr Val Arg
1370                1375                1380

Gly Lys His Gln Val Trp Val Arg Leu Ser Thr Glu Ala Tyr Ala
1385                1390                1395

Asp His Pro Tyr Val Ala Asn Leu Asp Ser Met Arg Phe Phe Thr
1400                1405                1410

Asp Ala Tyr Asp Val Glu Val Pro Pro Thr Asp Thr Ala Ala Leu
1415                1420                1425

Ala Ala Val Val Asp Ala Ala Gly Thr Pro Glu Ala Glu Ile Ala
1430                1435                1440

Arg Tyr Gly Arg Ile Asp Ala Arg Val Phe Thr Arg Glu Leu Ala
1445                1450                1455

Ala Ala Arg Ser Val Leu Ala Asp Ala Gly Ala Thr Gln Ala Gln
1460                1465                1470

Ala Asp Glu Arg Ala Arg Arg Leu Gly Leu Ala Thr Asp Gln Leu
1475                1480                1485

Val Pro Ala Glu Arg Arg Arg Leu Glu Asn Leu Val Ala Ser Ala
1490                1495                1500

Glu Ala Leu Thr Asp Glu Gly Tyr Ser Pro Glu Ser Trp Gln Ala
1505                1510                1515

Phe Arg Thr Ala Leu Ala Ala Thr Gly Thr Leu Asp Asp Ala
1520                1525                1530

Ala Ala Ser Asp Glu Ala Leu His Asp Ala Arg Leu Ala Leu Gln
1535                1540                1545

Gly Ala Val Asp Ala Leu Glu Glu Pro Ala Asp Val Val Leu Val
1550                1555                1560

Glu Val Glu Val Ser Pro Arg Cys Leu Ala Gly Lys Pro Tyr Val
1565                1570                1575

Ala Val Arg Ala Val Asn Val Ser Asp Ala Ala Val Asp Val Glu
1580                1585                1590

Leu Ala Ser Ser Leu Gly Thr Arg Ser Phe Val Gly Val Ala Pro
1595                1600                1605

Gly Ala Ser Ala Tyr Gln Ser Phe Ala Ala Arg Ser Ala Thr Gly
1610                1615                1620

Asp Leu Asp Val Thr Val Thr Ala Thr Gly Ala Asp Gly Thr Gln
1625                1630                1635

Thr Val Glu Gln Val Val Thr Val Pro Ser Cys Ser
1640                1645                1650

<210> SEQ ID NO 5
<211> LENGTH: 1079
<212> TYPE: PRT
<213> ORGANISM: Yarrowia lipolytica

<400> SEQUENCE: 5

Met Tyr Ser His Phe Asn Asn Glu Pro Val Ala Lys Arg Val Asn Asn
1               5                   10                  15

Leu Phe Thr Asp Arg Leu Arg Gln Phe Thr Ser Asp Gly Glu Tyr Arg
            20                  25                  30
```

-continued

```
Ser Leu Asn Leu Pro Ala Phe Tyr Glu Arg Glu Arg Leu Asp Gly Lys
         35                  40                  45

Asn His Val Ala Ile Glu Thr Tyr Ala Val Ser Asp Leu Arg Arg Pro
 50                  55                  60

Leu Phe Lys Asp Ala Leu Lys Glu Ala Asp Gly His Trp Lys Pro Ala
 65                  70                  75                  80

Lys Lys Gly Ser Glu Tyr Gly Pro Ser Trp Ala Thr His Trp Phe Lys
                 85                  90                  95

Ile Gln Val Cys Val Pro Pro Glu Trp Lys Lys Asn Tyr Tyr Lys Lys
                100                 105                 110

Gly Asp Leu Val Val Phe Asn Trp Asn Leu Asn Cys Glu Gly Leu Val
                115                 120                 125

Phe Ser Glu Ser Gly Glu Ala Leu Ile Gly Leu Ser Gly Glu Glu Arg
    130                 135                 140

Arg Glu Trp Pro Ile Pro Asp Asn Trp Phe Asp Gly Lys Cys His Thr
145                 150                 155                 160

Phe Tyr Ile Glu Ala Ser Cys Asn Gly Met Phe Gly Asn Ala Thr Gly
                165                 170                 175

Ser Ser Ile Gln Pro Pro Ser Asp Asn Arg Tyr Phe Arg Leu Asp Ser
                180                 185                 190

Ala Asp Leu Val Val Ile Asn Ser Glu Ala Arg His Leu Phe Val Asp
    195                 200                 205

Phe Trp Ile Ile Gly Asp Ala Ala Arg Glu Phe Pro Gly Asp Ser Trp
210                 215                 220

Gln Arg Gly Lys Ala Leu Asp Val Ala Asn Lys Ile Met Asp Ala Phe
225                 230                 235                 240

Asp Pro Glu Asn Pro Asp Glu Ser Ile Ala Glu Gly Arg Lys Leu Ala
                245                 250                 255

Lys Glu Tyr Leu Gly Asp Thr Thr Lys Ala Tyr Lys Gln Gln Leu Pro
                260                 265                 270

Phe Ala Asp Gly Leu Val Tyr Ala Leu Gly Asn Cys His Ile Asp Thr
    275                 280                 285

Ala Trp Leu Trp Pro Phe Ala Glu Thr Arg Arg Lys Ala Gly Arg Ser
290                 295                 300

Trp Ala Ser Gln Leu Glu Leu Ile Asp Lys Tyr Pro Glu Tyr Val Phe
305                 310                 315                 320

Val Ala Ser Gln Ala Gln Gln Phe Lys Trp Leu Lys Glu Asp Tyr Pro
                325                 330                 335

Asp Leu Phe Ala Lys Ile Gln Lys Gln Ala Lys Lys Gly Arg Phe Leu
                340                 345                 350

Pro Val Gly Gly Ala Trp Thr Glu Cys Asp Thr Asn Leu Pro Ser Gly
    355                 360                 365

Glu Ser Leu Leu Arg Gln Phe Leu Leu Gly Gln Arg Phe Phe Leu Glu
370                 375                 380

His Phe Gly Ser Leu Ser Asp Thr Phe Trp Leu Pro Asp Thr Phe Gly
385                 390                 395                 400

Tyr Ser Ala Gln Val Pro Gln Leu Cys Arg Leu Ala Gly Met Asp Arg
                405                 410                 415

Phe Leu Thr Gln Lys Leu Ser Trp Asn Asn Ile Asn Ser Phe Pro Asn
                420                 425                 430

Ser Thr Phe Asn Trp Val Ala Leu Asp Gly Ser Gln Val Leu Cys His
    435                 440                 445

Met Pro Pro Asn Asn Thr Tyr Thr Ser Met Ala Asn Phe Gly Asp Val
```

-continued

```
            450                 455                 460
Ser Arg Thr Gln Lys Gln Asn Lys Asn Leu Asp Thr Thr Arg Asn Ser
465                 470                 475                 480

Leu Met Leu Tyr Gly His Gly Asp Gly Gly Gly Pro Thr Ala Glu
                485                 490                 495

Met Leu Glu Lys Leu Arg Arg Cys Arg Gly Val Ser Asn Thr Val Gly
                500                 505                 510

Glu Leu Pro Pro Val Ile Gln Gly Gln Ser Val Thr Asp Phe Tyr Asn
                515                 520                 525

Glu Leu Leu Asp Gln Thr Asn Asn Gly Lys Asp Leu Val Thr Trp Val
                530                 535                 540

Gly Glu Leu Tyr Phe Glu Phe His Arg Gly Thr Tyr Thr Ser Gln Ala
545                 550                 555                 560

Gln Thr Lys Lys Gly Asn Arg Val Ser Glu Asn Leu Leu His Asp Val
                565                 570                 575

Glu Leu Leu Ala Thr Leu Ala Ser Ile Arg Asp Ser Ser Tyr Lys Tyr
                580                 585                 590

Pro Phe Ala Gln Leu Glu Ser Leu Trp Glu Asp Val Cys Leu Cys Gln
                595                 600                 605

Phe His Asp Val Leu Pro Gly Ser Cys Ile Glu Met Val Tyr Lys Asp
610                 615                 620

Val Lys Lys Ile His Gly Arg Val Ile Asp Thr Ala Ser His Leu Ile
625                 630                 635                 640

Asp Lys Ala Ala Ser Ala Leu Gly Leu Ser Gly His Pro Ser Lys Asp
                645                 650                 655

Ser Phe Asp Cys Thr Pro Val Ala Leu Asn Thr Met Pro Trp Ser Arg
                660                 665                 670

Thr Glu Val Val Ala Val Pro Gln Pro His Trp Asp Ala Thr Val Glu
                675                 680                 685

Leu Ala Glu Gly Val Glu Ile Gln Glu Asp Ser Gly Asn Ala Leu Val
                690                 695                 700

Met Met Ser Glu Ser Gly Pro Val Val Thr Thr Gln Ser Val Asp Leu
705                 710                 715                 720

Phe Lys Ser Glu Asp Ala Tyr Ile Leu Glu Asn Ser Gln Val Lys Val
                725                 730                 735

Thr Ile Cys Lys Asp Asp Gly Thr Leu Thr Ser Ile Tyr Asp Lys Glu
                740                 745                 750

Asn Asp Arg Arg Val Leu Ser Gly Thr Gly Asn Arg Leu Val Leu Phe
                755                 760                 765

Asp Asp Gln Pro Leu Ser Trp Gln Ala Trp Asp Thr Glu Val Phe Ser
770                 775                 780

Leu Gly Lys Lys Gln Tyr Ile Gly Ala Glu Asn Val Thr Arg His Ser
785                 790                 795                 800

Ile Val Ser Ser Gly Pro Leu Arg Ser Thr Val Ala Phe Thr Tyr Glu
                805                 810                 815

Phe Asn Lys Ser Val Val Thr Thr Glu Ile Ser Leu Asp Ala Asn Ser
                820                 825                 830

Pro Leu Val Thr Phe Asn Thr Arg Ala Asp Trp His Glu Thr Cys Lys
                835                 840                 845

Phe Leu Lys Val Glu Phe Pro Val Asp Val His Ser Glu Ser Ala Ser
850                 855                 860

Tyr Glu Ser Gln Phe Gly Val Val Lys Arg Pro Thr His Tyr Asn Thr
865                 870                 875                 880
```

-continued

Ser Trp Asp Val Ala Lys Phe Glu Val Cys Cys His Lys Phe Ala Asp
                885                 890                 895

Leu Ser Glu Leu Asp Tyr Gly Val Ser Ile Leu Asn Asp Cys Lys Tyr
            900                 905                 910

Gly Phe Ala Thr His Gly Asn Leu Met Arg Leu Ser Leu Leu Arg Ala
        915                 920                 925

Pro Lys Ala Pro Asp Ala His Ala Asp Met Gly His His Glu Phe Lys
    930                 935                 940

Tyr Gly Val Leu Ala His Lys Gly Pro Leu Gly Ala Thr Thr Val Arg
945                 950                 955                 960

Ala Ala Tyr Asn Phe Asn Asn Pro Leu Arg Val Lys Tyr Val Gly Leu
                965                 970                 975

Ser Glu Val Ser Thr Lys Gln Ala Phe Ser Leu Lys Gly Pro Ala Asn
            980                 985                 990

Leu Val Leu Ser Gln Val Lys Arg Ala Glu Val Asp Arg Ser Lys Lys
        995                 1000                1005

Ser Thr Asn Val Ile Leu Arg Val Tyr Glu Ala Leu Gly Gly Arg
    1010                1015                1020

Thr Arg Gly Lys Leu Val Ile Asp Leu Pro Asn Val Ser Val
    1025                1030                1035

Thr Lys Thr Cys Ala Leu Glu Tyr Ser Lys Glu Lys Gln Val Val
    1040                1045                1050

Ala Lys Ser Glu Gly Val Thr Ser Val Asp Ile Ser Leu Arg Ala
    1055                1060                1065

Phe Glu Val Ala Thr Tyr Lys Val Glu Leu Ala
    1070                1075

<210> SEQ ID NO 6
<211> LENGTH: 513
<212> TYPE: PRT
<213> ORGANISM: Aspergillus satoi

<400> SEQUENCE: 6

Met His Leu Pro Ser Leu Ser Leu Ser Leu Thr Ala Leu Ala Ile Ala
1               5                   10                  15

Ser Pro Ser Ala Ala Tyr Pro His Phe Gly Ser Ser Gln Pro Val Leu
            20                  25                  30

His Ser Ser Asp Thr Thr Gln Ser Arg Ala Asp Ala Ile Lys Ala
        35                  40                  45

Ala Phe Ser His Ala Trp Asp Gly Tyr Leu Gln Tyr Ala Phe Pro His
    50                  55                  60

Asp Glu Leu His Pro Val Ser Asn Gly Tyr Gly Asp Ser Arg Asn Gly
65                  70                  75                  80

Trp Gly Ala Ser Ala Val Asp Ala Leu Ser Thr Ala Val Ile Met Arg
                85                  90                  95

Asn Ala Thr Ile Val Asn Gln Ile Leu Asp His Val Gly Lys Ile Asp
            100                 105                 110

Tyr Ser Lys Thr Asn Thr Thr Val Ser Leu Phe Glu Thr Thr Ile Arg
        115                 120                 125

Tyr Leu Gly Gly Met Leu Ser Gly Tyr Asp Leu Leu Lys Gly Pro Val
    130                 135                 140

Ser Asp Leu Val Gln Asn Ser Ser Lys Ile Asp Val Leu Leu Thr Gln
145                 150                 155                 160

Ser Lys Asn Leu Ala Asp Val Leu Lys Phe Ala Phe Asp Thr Pro Ser

```
            165                 170                 175
Gly Val Pro Tyr Asn Asn Leu Asn Ile Thr Ser Gly Gly Asn Asp Gly
            180                 185                 190

Ala Lys Thr Asn Gly Leu Ala Val Thr Gly Thr Leu Ala Leu Glu Trp
            195                 200                 205

Thr Arg Leu Ser Asp Leu Thr Gly Asp Thr Thr Tyr Ala Asp Leu Ser
            210                 215                 220

Gln Lys Ala Glu Ser Tyr Leu Leu Asn Pro Gln Pro Lys Ser Ala Glu
225                 230                 235                 240

Pro Phe Pro Gly Leu Val Gly Ser Asn Ile Asn Ile Ser Asn Gly Gln
            245                 250                 255

Phe Thr Asp Ala Gln Val Ser Trp Asn Gly Gly Asp Asp Ser Tyr Tyr
            260                 265                 270

Glu Tyr Leu Ile Lys Met Tyr Val Tyr Asp Pro Lys Arg Phe Gly Leu
            275                 280                 285

Tyr Lys Asp Arg Trp Val Ala Ala Gln Ser Thr Met Gln His Leu
            290                 295                 300

Ala Ser His Pro Ser Ser Arg Pro Asp Leu Thr Phe Leu Ala Ser Tyr
305                 310                 315                 320

Asn Asn Gly Thr Leu Gly Leu Ser Ser Gln His Leu Thr Cys Phe Asp
            325                 330                 335

Gly Gly Ser Phe Leu Leu Gly Gly Thr Val Leu Asn Arg Thr Asp Phe
            340                 345                 350

Ile Asn Phe Gly Leu Asp Leu Val Ser Gly Cys His Asp Thr Tyr Asn
            355                 360                 365

Ser Thr Leu Thr Gly Ile Gly Pro Glu Ser Phe Ser Trp Asp Thr Ser
            370                 375                 380

Asp Ile Pro Ser Ser Gln Gln Ser Leu Tyr Glu Lys Ala Gly Phe Tyr
385                 390                 395                 400

Ile Thr Ser Gly Ala Tyr Ile Leu Arg Pro Glu Val Ile Glu Ser Phe
            405                 410                 415

Tyr Tyr Ala Trp Arg Val Thr Gly Gln Glu Thr Tyr Arg Asp Trp Ile
            420                 425                 430

Trp Ser Ala Phe Ser Ala Val Asn Asp Tyr Cys Arg Thr Ser Ser Gly
            435                 440                 445

Phe Ser Gly Leu Thr Asp Val Asn Ala Ala Asn Gly Gly Ser Arg Tyr
            450                 455                 460

Asp Asn Gln Glu Ser Phe Leu Phe Ala Glu Val Met Lys Tyr Ser Tyr
465                 470                 475                 480

Met Ala Phe Ala Glu Asp Ala Ala Trp Gln Val Gln Pro Gly Ser Gly
            485                 490                 495

Asn Gln Phe Val Phe Asn Thr Glu Ala His Pro Val Arg Val Ser Ser
            500                 505                 510

Thr
```

<210> SEQ ID NO 7
<211> LENGTH: 1810
<212> TYPE: PRT
<213> ORGANISM: Cellulosimicrobium cellulans

<400> SEQUENCE: 7

```
Met Thr Arg Pro Leu Pro Pro Gly Arg Ala Val Ala Arg Ser Gly Ser
1               5                   10                  15

Gly Arg Ala Arg Pro Leu Gly Leu Val Leu Ala Ala Ala Leu Ala Val
```

-continued

```
                20                  25                  30
Pro Leu Gly Val Pro Leu Ala Ala Pro Ala Gly Ala Leu Ala Ala Ala
            35                  40                  45
Pro Ala Ala Ala Glu Pro Gly Asp Phe Ser Ser Phe Glu Ser
 50                  55                  60
Gly Asp Pro Ala Ala Leu Pro Thr Thr Val Ala Glu Arg Asp Gly Ala
 65                  70                  75                  80
Pro Trp Gln Ala Asn Val Gly Ser Phe Thr Ala Gly Leu Pro Gly Ser
                85                  90                  95
Val Leu Gly Gln Leu Lys Gly Val Thr Ala Ser Ala Gln Asn Leu Pro
            100                 105                 110
Asn Glu Gly Ala Ala Asn Leu Ala Asp Gly Ser Ser Gly Thr Lys Trp
            115                 120                 125
Leu Ala Phe Ala Ser Thr Gly Trp Val Arg Tyr Glu Phe Ala Glu Pro
            130                 135                 140
Val Ser Phe Val Ala Tyr Thr Met Thr Ser Gly Asp Asp Ala Ala Gly
145                 150                 155                 160
Arg Asp Pro Lys Thr Trp Thr Val Glu Gly Ser Asn Asp Gly Ser Thr
                165                 170                 175
Trp Ala Ala Leu Asp Arg Arg Thr Asp Glu Asp Phe Pro Asn Arg Gln
            180                 185                 190
Gln Thr Arg Thr Phe Glu Leu Glu Ala Pro Thr Ala Ala Tyr Thr Tyr
            195                 200                 205
Leu Arg Leu Asn Val Thr Ala Asn Ser Gly Asp Ser Ile Val Gln Leu
            210                 215                 220
Ala Gly Trp Asp Leu Ser Ala Asp Leu Ser Ala Gly Pro Ser Ala Ala
225                 230                 235                 240
Pro Met Thr Thr Lys Val Gly Thr Gly Pro Arg Val Ser Phe Thr Asn
                245                 250                 255
Lys Ala Gly Val Gly Phe Ser Gly Leu His Ser Leu Arg Tyr Asp Gly
            260                 265                 270
Ser His Leu Ala Asp Gly Glu Thr Tyr Ala Thr Asn Val Leu Tyr Asp
            275                 280                 285
Asp Val Asp Val Val Gly Glu Asp Thr Arg Leu Ser Tyr Thr Ile
            290                 295                 300
Phe Pro Glu Leu Leu Asp Asp Leu Gln Tyr Pro Ser Thr Tyr Ala Ala
305                 310                 315                 320
Val Asp Val Leu Phe Thr Asp Gly Thr Tyr Leu Ser Asp Leu Gly Ala
                325                 330                 335
Arg Asp Ala His Glu Thr Val Ala Thr Ala Gln Ala Gln Gly Glu Gly
            340                 345                 350
Lys Ile Leu Tyr Ala Asp Gln Trp Asn Ser Val Arg Val Asp Leu Gly
            355                 360                 365
Asp Val Ala Glu Gly Lys Thr Val Asp Gln Val Leu Leu Gly Tyr Asp
            370                 375                 380
Asn Pro Gly Gly His Ala Gly Thr Lys Phe Ala Gly Trp Leu Asp Asp
385                 390                 395                 400
Val Glu Ile Thr Ala Glu Pro Ala Thr Ile Asp Gly Ser Ser Leu Ala
                405                 410                 415
Asn Tyr Val Asp Thr Arg Arg Gly Thr Leu Ala Ser Gly Ser Phe Ser
            420                 425                 430
Arg Gly Asn Asn Ile Pro Ala Thr Ala Thr Pro Asn Gly Phe Asn Phe
            435                 440                 445
```

Trp Thr Pro Tyr Thr Asn Ala Ser Ser Gln Ser Trp Leu Tyr Glu Tyr
    450                 455                 460

His Lys Ala Asn Asn Ala Asn Asn Lys Pro Val Leu Gln Gly Phe Gly
465                 470                 475                 480

Ile Ser His Glu Pro Ser Pro Trp Met Gly Asp Arg Asn Gln Leu Thr
                485                 490                 495

Phe Leu Pro Ser Thr Ala Ser Gly Thr Pro Asp Ala Thr Leu Ser Thr
            500                 505                 510

Arg Gly Leu Glu Phe Asp His Ala Asp Glu Thr Ala Arg Pro Asp Tyr
        515                 520                 525

Tyr Gly Val Thr Phe Thr Asn Gly Ser Ala Ile Glu Ala Thr Pro Thr
    530                 535                 540

Asp His Gly Ala Val Leu Arg Phe Ser Tyr Pro Gly Ala Lys Gly His
545                 550                 555                 560

Val Leu Val Asp Lys Val Asp Gly Ser Ser Lys Leu Thr Tyr Asp Gln
                565                 570                 575

Ala Thr Gly Thr Ile Ser Gly Trp Val Glu Asn Gly Ser Gly Leu Ser
            580                 585                 590

Val Gly Arg Thr Arg Met Phe Val Ala Gly Thr Phe Asp Arg Ser Pro
        595                 600                 605

Thr Ala Val Gly Thr Ala Ala Gly Asn Arg Ala Asp Ala Arg Phe Ala
    610                 615                 620

Thr Phe Glu Thr Ser Ser Asp Lys Thr Val Glu Leu Arg Val Ala Thr
625                 630                 635                 640

Ser Phe Ile Ser Leu Asp Gln Ala Arg Lys Asn Leu Asp Leu Glu Val
                645                 650                 655

Thr Gly Lys Thr Phe Thr Glu Val Lys Ala Ala Ala Gln Ala Trp
            660                 665                 670

Asn Asp Arg Leu Gly Val Ile Glu Val Glu Gly Ala Ser Glu Asp Gln
        675                 680                 685

Leu Val Thr Leu Tyr Ser Asn Leu Tyr Arg Leu Asn Leu Tyr Pro Asn
    690                 695                 700

Ser Gln Phe Glu Asn Thr Gly Thr Ala Gln Glu Pro Val Tyr Arg Tyr
705                 710                 715                 720

Ala Ser Pro Val Ser Ala Thr Thr Gly Ser Ala Thr Asp Thr Gln Thr
                725                 730                 735

Asn Ala Lys Ile Val Asp Gly Lys Ile Tyr Val Asn Asn Gly Phe Trp
            740                 745                 750

Asp Thr Tyr Arg Thr Ala Trp Pro Ala Tyr Ser Leu Leu Tyr Pro Glu
        755                 760                 765

Leu Ala Ala Glu Leu Val Asp Gly Phe Val Gln Gln Tyr Arg Asp Gly
    770                 775                 780

Gly Trp Ile Ala Arg Trp Ser Ser Pro Gly Tyr Ala Asp Leu Met Thr
785                 790                 795                 800

Gly Thr Ser Ser Asp Val Ala Phe Ala Asp Ala Tyr Leu Lys Gly Ser
                805                 810                 815

Leu Pro Thr Gly Thr Ala Leu Glu Ala Tyr Asp Ala Ala Leu Arg Asn
            820                 825                 830

Ala Thr Val Ala Pro Pro Ser Asn Ala Val Gly Arg Lys Gly Leu Gln
        835                 840                 845

Thr Ser Pro Phe Leu Gly Phe Thr Pro Glu Ser Thr His Glu Ser Val
    850                 855                 860

```
Ser Trp Gly Leu Glu Gly Leu Val Asn Asp Phe Gly Ile Gly Asn Met
865                 870                 875                 880

Ala Ala Ala Leu Ala Glu Asp Pro Ala Thr Pro Glu Glu Arg Arg Glu
                885                 890                 895

Thr Leu Arg Glu Glu Ser Ala Tyr Phe Leu Glu Arg Ala Thr His Tyr
            900                 905                 910

Val Glu Leu Phe Asp Pro Glu Val Asp Phe Val Pro Arg His Glu
        915                 920                 925

Asp Gly Thr Trp Ala Val Asp Pro Glu Thr Tyr Asp Pro Glu Ala Trp
930                 935                 940

Gly Gly Gly Tyr Thr Glu Thr Asn Gly Trp Asn Phe Ala Phe His Ala
945                 950                 955                 960

Pro Gln Asp Gly Gln Gly Leu Ala Asn Leu Tyr Gly Gly Lys Gln Gly
                965                 970                 975

Leu Glu Asp Lys Leu Asp Glu Phe Phe Ser Thr Pro Glu Lys Gly Ala
            980                 985                 990

Gly Asn Gly Gly Ile His Glu Gln Arg Glu Ala Arg Asp Val Arg Met
        995                 1000                1005

Gly Gln Trp Gly Met Ser Asn Gln Val Ser His His Ile Pro Trp
    1010                1015                1020

Leu Tyr Asp Ala Ala Gly Ala Pro Ser Lys Ala Gln Glu Lys Val
    1025                1030                1035

Arg Glu Val Thr Arg Arg Leu Phe Val Gly Ser Glu Ile Gly Gln
    1040                1045                1050

Gly Tyr Pro Gly Asp Glu Asp Asn Gly Glu Met Ser Ser Trp Trp
    1055                1060                1065

Ile Phe Ala Ser Leu Gly Phe Tyr Pro Leu Gln Val Gly Ser Asp
    1070                1075                1080

Gln Tyr Ala Val Gly Ser Pro Leu Phe Asp Lys Ala Thr Val His
    1085                1090                1095

Leu Pro Asp Gly Asp Leu Val Val Asn Ala Glu Asn Asn Ser Val
    1100                1105                1110

Asp Asn Val Tyr Val Gln Ser Leu Ala Val Asp Gly Glu Ala Arg
    1115                1120                1125

Thr Ser Thr Ser Leu Ser Gln Ala Asp Leu Ser Gly Gly Thr Thr
    1130                1135                1140

Leu Asp Phe Val Met Gly Pro Glu Pro Ser Asp Trp Gly Thr Gly
    1145                1150                1155

Glu Asp Asp Ala Pro Pro Ser Leu Thr Glu Gly Asp Glu Pro Pro
    1160                1165                1170

Thr Pro Val Gln Asp Ala Thr Ala Gly Leu Gly Thr Thr Thr
    1175                1180                1185

Val Ala Asp Gly Asp Ala Thr Thr Ser Ala Ala Ala Leu Thr Asp
    1190                1195                1200

Asn Thr Ser Gly Thr Arg Thr Thr Phe Ala Thr Thr Thr Pro Ser
    1205                1210                1215

Ile Thr Trp Ala Gly Asn Gly Ile Arg Pro Thr Val Gly Ser Tyr
    1220                1225                1230

Thr Leu Thr Ser Gly Ala Ser Gly Thr Ala Ser Pro Ser Ala Trp
    1235                1240                1245

Thr Leu Glu Gly Ser Asp Asp Gly Glu Thr Trp Thr Thr Leu Asp
    1250                1255                1260

Glu Arg Ser Gly Glu Gln Phe Arg Trp Ala Leu Gln Thr Arg Pro
```

```
            1265                1270                1275
Phe Thr Val Ala Glu Pro Thr Ala Phe Ala Arg Tyr Arg Val Thr
            1280                1285                1290
Val Thr Ala Thr Ser Gly Ser Gly Ala Leu Ser Leu Ala Glu Val
            1295                1300                1305
Glu Leu Leu Ala Asp Pro Lys Glu Ser Gly Ala Glu Glu Leu Thr
            1310                1315                1320
Leu Ser Ala Ala Pro Asp Arg Asp Gly Val Thr Gly Arg Glu Val
            1325                1330                1335
Ser Gly Ser Phe Ala Thr Leu Thr Gly Val Glu Gly Asp Val Ala
            1340                1345                1350
Ala Leu Asp Val Gln Val Ala Phe Gly Asp Gly Ser Glu Pro Val
            1355                1360                1365
Ala Gly Thr Leu Arg Ala Gly Ala Phe Gly Gly Tyr Ala Val Asp
            1370                1375                1380
Ala Ala His Thr Trp Thr Ala Pro Gly Val Tyr Pro Val Thr Val
            1385                1390                1395
Thr Val Ser Gly Glu Gly Ile Glu Thr Val Ser Ala Ser Ser Tyr
            1400                1405                1410
Val Ser Val Ser Leu Leu Arg Glu Gly Ser Leu Leu Ala Ala Tyr
            1415                1420                1425
Asp Asn Val Cys Ile Gly Asp Ala Gly Thr Thr Val Gly Ser Cys
            1430                1435                1440
Asp Gly Gln Gly Val Phe Phe Asp Arg Ala Gln Leu Ala Ala Lys
            1445                1450                1455
Gly Phe Val Gln Gly Glu Arg Ala Thr Val Pro Gly Thr Asp Leu
            1460                1465                1470
Ala Phe Asp Val Pro Ala Val Pro Ala Gly Gln Pro Asp Asn Ala
            1475                1480                1485
Thr Gly Asp Gly Gln Thr Ile Glu Leu Asp Val Pro Ala Asp Ala
            1490                1495                1500
Glu Gln Leu Ser Val Ile Gly Thr Gly Thr Glu Lys Asn Gln Gln
            1505                1510                1515
Ala Thr Gly Thr Leu Thr Phe Asp Asp Gly Ser Thr Gln Pro Ile
            1520                1525                1530
Asp Leu Ser Phe Gly Asp Trp Ser Gly Ala Ala Arg Asn Pro Val
            1535                1540                1545
Phe Gly Asn Ile Pro Val Ala Val Thr Asp Ser Arg Leu Arg Gly
            1550                1555                1560
Gly Ser Pro Gln Thr Gly Thr Pro Ala Ala Phe Phe Ala Thr Ala
            1565                1570                1575
Pro Ile Thr Leu Pro Glu Gly Lys Arg Pro Val Ser Leu Thr Leu
            1580                1585                1590
Pro Asp Gln Pro Gly Glu Leu Ser Arg Asp Gly Arg Ile His Val
            1595                1600                1605
Val Ala Val Ala His Asp Gly Thr Phe Ala Glu His Pro Ala Leu
            1610                1615                1620
Glu Val Thr Ala Ala Glu Gly Val Thr Leu Ala Val Gly Gln Thr
            1625                1630                1635
Ser Asp Val Ala Leu Ala Gln Val Ala Gly Gly Arg Glu Gly Ala
            1640                1645                1650
Asp Leu Arg Ala Ala Val Thr Trp Gly Asp Gly Ser Asp Val Ala
            1655                1660                1665
```

```
Ala Gly Ala Val Thr Asp Gly Ser Val Ser Gly Ser His Ala Tyr
    1670            1675            1680

Thr Ala Ala Gly Thr Tyr Thr Ala Tyr Val Val Val Asp Asp Gly
    1685            1690            1695

Trp Thr Ser Gln Val Val Glu Val Pro Val Thr Val Thr Glu Ala
    1700            1705            1710

Glu Pro Ala Leu Ala Val Asp Val Thr Val Ser Thr Arg Cys Leu
    1715            1720            1725

Ala Gly Lys Ala Tyr Val Ala Val Arg Ala Glu Asn Gly Glu Asp
    1730            1735            1740

Val Pro Leu Ala Ile Arg Leu Val Thr Pro Phe Gly Thr Lys Glu
    1745            1750            1755

Val Ala Ala Val Ala Pro Gly Ala Asn Ala Tyr Ser Phe Ala Thr
    1760            1765            1770

Arg Val Thr Ala Val Glu Ala Gly Thr Val Thr Val Glu Ala Thr
    1775            1780            1785

Arg Gly Thr Gly Asp Glu Glu Val Thr Ala Ser Ile Gln Ala Asp
    1790            1795            1800

Tyr Ala Ala Val Thr Cys Gly
    1805            1810

<210> SEQ ID NO 8
<211> LENGTH: 282
<212> TYPE: PRT
<213> ORGANISM: Aspergillus oryzae

<400> SEQUENCE: 8

Gly Leu Thr Thr Gln Lys Ser Ala Pro Trp Gly Leu Gly Ser Ile Ser
1               5                   10                  15

His Lys Gly Gln Gln Ser Thr Asp Tyr Ile Tyr Asp Thr Ser Ala Gly
            20                  25                  30

Glu Gly Thr Tyr Ala Tyr Val Val Asp Ser Gly Val Asn Val Asp His
        35                  40                  45

Glu Glu Phe Glu Gly Arg Ala Ser Lys Ala Tyr Asn Ala Ala Gly Gly
50                  55                  60

Gln His Val Asp Ser Ile Gly His Gly Thr His Val Ser Gly Thr Ile
65                  70                  75                  80

Ala Gly Lys Thr Tyr Gly Ile Ala Lys Lys Ala Ser Ile Leu Ser Val
                85                  90                  95

Lys Val Phe Gln Gly Glu Ser Ser Thr Ser Val Ile Leu Asp Gly
            100                 105                 110

Phe Asn Trp Ala Ala Asn Asp Ile Val Ser Lys Lys Arg Thr Ser Lys
        115                 120                 125

Ala Ala Ile Asn Met Ser Leu Gly Gly Gly Tyr Ser Lys Ala Phe Asn
    130                 135                 140

Asp Ala Val Glu Asn Ala Phe Glu Gln Gly Val Leu Ser Val Val Ala
145                 150                 155                 160

Ala Gly Asn Glu Asn Ser Asp Ala Gly Gln Thr Ser Pro Ala Ser Ala
                165                 170                 175

Pro Asp Ala Ile Thr Val Ala Ala Ile Gln Lys Ser Asn Asn Arg Ala
            180                 185                 190

Ser Phe Ser Asn Phe Gly Lys Val Val Asp Val Phe Ala Pro Gly Gln
        195                 200                 205

Asp Ile Leu Ser Ala Trp Ile Gly Ser Ser Ser Ala Thr Asn Thr Ile
```

```
            210                 215                 220
Ser Gly Thr Ser Met Ala Thr Pro His Ile Val Gly Leu Ser Leu Tyr
225                 230                 235                 240

Leu Ala Ala Leu Glu Asn Leu Asp Gly Pro Ala Ala Val Thr Lys Arg
                245                 250                 255

Ile Lys Glu Leu Ala Thr Lys Asp Val Val Lys Asp Val Lys Gly Ser
                260                 265                 270

Pro Asn Leu Leu Ala Tyr Asn Gly Asn Ala
                275                 280

<210> SEQ ID NO 9
<211> LENGTH: 403
<212> TYPE: PRT
<213> ORGANISM: Aspergillus oryzae

<400> SEQUENCE: 9

Met Gln Ser Ile Lys Arg Thr Leu Leu Leu Gly Ala Ile Leu Pro
1               5                   10                  15

Ala Val Leu Gly Ala Pro Val Gln Glu Thr Arg Arg Ala Ala Glu Lys
                20                  25                  30

Leu Pro Gly Lys Tyr Ile Val Thr Phe Lys Pro Gly Ile Asp Glu Ala
                35                  40                  45

Lys Ile Gln Glu His Thr Thr Trp Ala Thr Asn Ile His Gln Arg Ser
50                  55                  60

Leu Glu Arg Arg Gly Ala Thr Gly Gly Asp Leu Pro Val Gly Ile Glu
65                  70                  75                  80

Arg Asn Tyr Lys Ile Asn Lys Phe Ala Ala Tyr Ala Gly Ser Phe Asp
                85                  90                  95

Asp Ala Thr Ile Glu Glu Ile Arg Lys Asn Glu Asp Val Ala Tyr Val
                100                 105                 110

Glu Glu Asp Gln Ile Tyr Tyr Leu Asp Gly Leu Thr Thr Gln Lys Ser
                115                 120                 125

Ala Pro Trp Gly Leu Gly Ser Ile Ser His Lys Gly Gln Gln Ser Thr
130                 135                 140

Asp Tyr Ile Tyr Asp Thr Ser Ala Gly Glu Gly Thr Tyr Ala Tyr Val
145                 150                 155                 160

Val Asp Ser Gly Val Asn Val Asp His Glu Glu Phe Glu Gly Arg Ala
                165                 170                 175

Ser Lys Ala Tyr Asn Ala Ala Gly Gly Gln His Val Asp Ser Ile Gly
                180                 185                 190

His Gly Thr His Val Ser Gly Thr Ile Ala Gly Lys Thr Tyr Gly Ile
                195                 200                 205

Ala Lys Lys Ala Ser Ile Leu Ser Val Lys Val Phe Gln Gly Glu Ser
210                 215                 220

Ser Ser Thr Ser Val Ile Leu Asp Gly Phe Asn Trp Ala Ala Asn Asp
225                 230                 235                 240

Ile Val Ser Lys Lys Arg Thr Ser Lys Ala Ala Ile Asn Met Ser Leu
                245                 250                 255

Gly Gly Gly Tyr Ser Lys Ala Phe Asn Asp Ala Val Glu Asn Ala Phe
                260                 265                 270

Glu Gln Gly Val Leu Ser Val Ala Ala Gly Asn Glu Asn Ser Asp
                275                 280                 285

Ala Gly Gln Thr Ser Pro Ala Ser Ala Pro Asp Ala Ile Thr Val Ala
                290                 295                 300
```

Ala Ile Gln Lys Ser Asn Asn Arg Ala Ser Phe Ser Asn Phe Gly Lys
305                 310                 315                 320

Val Val Asp Val Phe Ala Pro Gly Gln Asp Ile Leu Ser Ala Trp Ile
            325                 330                 335

Gly Ser Ser Ser Ala Thr Asn Thr Ile Ser Gly Thr Ser Met Ala Thr
        340                 345                 350

Pro His Ile Val Gly Leu Ser Leu Tyr Leu Ala Ala Leu Glu Asn Leu
    355                 360                 365

Asp Gly Pro Ala Ala Val Thr Lys Arg Ile Lys Glu Leu Ala Thr Lys
    370                 375                 380

Asp Val Val Lys Asp Val Lys Gly Ser Pro Asn Leu Leu Ala Tyr Asn
385                 390                 395                 400

Gly Asn Ala

<210> SEQ ID NO 10
<211> LENGTH: 1272
<212> TYPE: DNA
<213> ORGANISM: Artificial Sequence
<220> FEATURE:
<223> OTHER INFORMATION: codon optimized sequence encoding alkaline
      protease

<400> SEQUENCE: 10
ggatccatgc agtccattaa gcgaactctg ctgctgctgg gagccattct gcccgccgtg      60
ctgggagccc ccgttcagga gacccgacga gccgccgaga agctccccgg caagtacatt     120
gtcaccttca gcctggtat cgacgaggct aagattcagg agcacaccac ttgggccacc      180
aacatccatc agcgatccct cgagcgacga ggagccaccg gcggtgacct gcctgtggga     240
atcgagcgaa actacaagat taacaagttc gccgcttacg ctggatcttt tgacgatgcc     300
accatcgagg agattcgaaa gaacgaggac gtcgcttacg tggaggaaga ccagatctac     360
tacctcgatg gtctgaccac tcagaagtcc gctccttggg gcctgggctc catctctcac     420
aagggacagc agtcgactga ctacatctac gataccctccg ctggcgaggg tacttacgcc    480
tacgtcgtgg actccggtgt taacgtcgat cacgaggagt ttgagggacg agcctctaag     540
gcttacaacg ccgctggagg ccagcatgtg gactctatcg acacggcac ccatgtttcg      600 ggtactattg ccggaaagac ctacggcatc gccaagaagg cttctattct ctcggtgaag     660
gttttccagg gagagtcctc ttcgacctct gtcatcctgg acggctttaa ctgggccgct     720
aacgatattg tgtctaagaa gcgaacctcg aaggccgcta tcaacatgtc cctcggtgga     780
ggctactcta aggccttcaa cgacgctgtt gagaacgcct tgagcagggg tgtcctgtct     840
gttgtggctg ctggtaacga gaactctgac gctggacaga cctcccctgc ttctgctcct     900
gatgccatca ctgtggccgc tattcagaag tccaacaacc gagcttcgtt ctccaacttt     960
ggcaaggtgg ttgacgttttt cgcccccgga caggatatcc tctctgcttg gattggctcc    1020
tcttcggcca ccaacactat ctcgggcacc tccatggcca ctccccacat tgtcggtctg    1080
tccctctacc tggctgctct ggagaacctg gacggacctg ccgctgttac caagcgaatc    1140
aaggagctgg ctactaagga cgtcgtgaag gatgtcaagg ttctcctaa cctgctcgcc     1200 tacaacggca acgcttctgg cggcggagga catcaccacc atcaccatca ccaccatcat    1260
tgataaccta gg                                                        1272

<210> SEQ ID NO 11
<211> LENGTH: 20
<212> TYPE: PRT

```
<213> ORGANISM: Artificial Sequence
<220> FEATURE:
<223> OTHER INFORMATION: peptide from Jack bean mannosidase

<400> SEQUENCE: 11

Asn Lys Ile Pro Arg Ala Gly Trp Gln Ile Asp Pro Phe Gly His Ser
1               5                   10                  15

Ala Val Gln Gly
            20

<210> SEQ ID NO 12
<211> LENGTH: 7
<212> TYPE: PRT
<213> ORGANISM: Artificial Sequence
<220> FEATURE:
<223> OTHER INFORMATION: alkaline protease substrate

<400> SEQUENCE: 12

Ile Gln Asn Cys Pro Leu Gly
1               5
```

METHODS AND MATERIALS FOR TREATMENT OF POMPE'S DISEASE

CROSS-REFERENCE TO RELATED APPLICATIONS

This application is a divisional, and claims priority of co-pending U.S. application Ser. No. 13/831,368, filed Mar. 14, 2013, which claims the benefit of U.S. Provisional Application No. 61/611,485, filed Mar. 15, 2012. The disclosure of the prior applications is considered part of (and is incorporated by reference in) the disclosure of this application.

TECHNICAL FIELD

This invention relates to isolated molecular complexes having acid alpha glucosidase activity, and more particularly to molecular complexes comprising at least two polypeptides derived by proteolysis from a precursor molecule, wherein the molecular complex includes at least one modification that results in enhanced ability of the molecular complex to be transported to the interior of a mammalian cell.

BACKGROUND

Pompe's disease (also referred to as glycogen-storage disease type II or acid-maltase deficiency) is a rare autosomal recessive disorder that results in an accumulation of glycogen in the lysosome due to a deficiency of acid alpha glucosidase (GAA). The build-up of glycogen causes progressive muscle weakness (myopathy) throughout the body and affects various body tissues, including the heart, skeletal muscles, live, and nervous system.

Pompe's disease is broadly classified into infantile and late onset forms. In the infantile-onset form, infants typically present during early infancy (4-8 months of age) with weakness and floppiness, and are unable to hold up their heads and cannot do other motor tasks common for their age, such as rolling over. Without treatment, infants with Pompe's disease usually die before 12 months of age due to heart failure and respiratory weakness. See, United Pompe Foundation. Late onset forms (including juvenile and adult forms), have a later onset and progress more slowly than the infantile form. Recombinant human GAA (Myozyme® or Lumizyme®) is used to treat Pompe's disease. However, Myozyme® or Lumizyme® are both very expensive, with costs well over $300,000 per year. As such, there is a need for improved treatments for Pompe's disease.

SUMMARY

In one aspect, this document features an isolated molecular complex having acid alpha glucosidase (GAA) activity and that includes at least two polypeptides (e.g., at least three or at least four polypeptides), each polypeptide having at least 85% (e.g., at least 90%, 95%, 99%, or 100%) sequence identity to a segment of the amino acid sequence set forth in SEQ ID NO: 1, each segment being derived by proteolysis of the amino acid sequence set forth in SEQ ID NO: 1 at one or more sites between amino acid 50 and amino acid 74 (e.g., between amino acid 56 and amino acid 68 or between amino acid 60 and amino acid 65). The molecular complex includes at least one modification that results in enhanced ability of the molecular complex to be transported to the interior of a mammalian cell. Proteolysis of the amino acid sequence set forth in SEQ ID NO:1 further can include cleavage at one or more sites between amino acid 719 and amino acid 746 or cleavage at one or more sites between amino acid 137 and amino acid 151 of the amino acid sequence set forth in SEQ ID NO:1. Proteolysis further can include cleavage at one or more sites between amino acid 719 and amino acid 746 of the amino acid sequence set forth in SEQ ID NO:1 and cleavage at one or more sites between amino acid 137 and amino acid 151 of the amino acid sequence set forth in SEQ ID NO:1.

In any of the molecular complexes described herein, at least one of the polypeptides can include one or more phosphorylated N-glycans and the modification can include uncapping and demannosylation of at least one phosphorylated N-glycan. At least 40% (e.g., at least 60%, 80%, 90%, 95%, or 99%) of the N-glycans on at least one of the polypeptides can be uncapped and demannosylated.

In any of the molecular complexes described herein, for one of the at least two polypeptides, the segment includes amino acids 22 to 57 of SEQ ID NO:1, and wherein for one of the at least two polypeptides, the segment includes amino acids 66 to 896 of SEQ ID NO:1.

In any of the molecular complexes described herein containing at least three polypeptides, for one of the at least three polypeptides, the segment includes amino acids 22 to 57 of SEQ ID NO:1, wherein for one of the at least three polypeptides, the segment includes amino acids 66 to 726 of SEQ ID NO:1, and wherein for one of the at least three polypeptides, the segment includes amino acids 736 to 896 of SEQ ID NO:1.

In any of the molecular complexes described herein containing at least four polypeptides, for one of the at least four polypeptides, the segment includes amino acids 22 to 57 of SEQ ID NO:1, wherein for one of the at least four polypeptides, the segment includes amino acids 66 to 143 of SEQ ID NO:1, wherein for one of the at least four polypeptides, the segment includes amino acids 158 to 726 of SEQ ID NO:1, and wherein for one of the at least four polypeptides, the segment includes amino acids 736 to 896 of SEQ ID NO:1.

In any of the molecular complexes described herein, the at least one modification can include any one of the following fused to at least one polypeptide in the molecular complex: a ligand for an extracellular receptor, a targeting domain that binds an extracellular domain of a receptor on the surface of a target cell, a urokinase-type plasminogen receptor, or the recognition domain of human insulin-like growth factor II.

This document also features compositions that include any of the molecular complexes described herein, wherein the molecular complex is lyophilized. The composition can be packaged as a single use vial.

This document also features a pharmaceutical composition that includes any of the molecular complexes described herein and a pharmaceutically acceptable carrier. The composition can be formulated for intravenous or subcutaneous administration. The composition can be formulated for intravenous infusion.

In another aspect, this document features a method of treating Pompe's disease. The method includes administering any of the compositions described herein to a patient diagnosed with Pompe's disease. The patient can be diagnosed with infantile onset Pompe's disease or late onset Pompe's disease.

This document also features a method for making a molecular complex. The method includes contacting a polypeptide having at least 85% sequence identity to the amino acid sequence set forth in SEQ ID NO:1 with a protease having at least 85% (e.g., at least 90%, at least 95%, at least 99%, or 100%) sequence identity to the amino acid sequence set forth in SEQ ID NO:8, wherein the protease cleaves the polypeptide at one or more sites between amino acid 50 and amino acid 74 (e.g., between amino acid 56 and amino acid 68 or between amino acid 60 and amino acid 65). The contacting step can be performed in vitro.

This document also features a method for making a molecular complex that includes uncapped and demannosylated phosphorylated N-glycans. The method includes contacting a molecular complex with a mannosidase capable of (i) hydrolyzing a mannose-1-phospho-6-mannose moiety to mannose-6-phosphate and (ii) hydrolyzing terminal alpha-1,2 mannose, alpha-1,3 mannose and/or alpha-1,6 mannose linkages, the molecular complex having GAA activity and including at least two polypeptides, each polypeptide having at least 85% sequence identity to a segment of the amino acid sequence set forth in SEQ ID NO: 1, each segment being derived by proteolysis of the amino acid sequence set forth in SEQ ID NO: 1 at one or more sites between amino acid 50 and amino acid 74 (e.g., between amino acid 56 and amino acid 68 or between amino acid 60 and amino acid 65), wherein before the contacting, at least one of the polypeptides includes phosphorylated N-glycans containing one or more mannose-1-phospho-6-mannose moieties. The mannosidase can be a family 38 glycosyl hydrolase (e.g., a *Canavalia ensiformis* mannosidase or a *Yarrowia lipolytica* mannosidase). The contacting can occur in a recombinant fungal cell expressing the mannosidase.

This document also features a method of making a molecular complex that includes uncapped and demannosylated phosphorylated N-glycans. The method includes contacting a molecular complex with a mannosidase capable of hydrolyzing terminal alpha-1,2 mannose, alpha-1,3 mannose and/or alpha-1,6 mannose linkages, the molecular complex having GAA activity and comprising at least two polypeptides, each polypeptide having at least 85% sequence identity to a segment of the amino acid sequence set forth in SEQ ID NO: 1, each segment being derived by proteolysis of the amino acid sequence set forth in SEQ ID NO: 1 at one or more sites between amino acid 50 and amino acid 74 (e.g., between amino acid 56 and amino acid 68 or between amino acid 60 and amino acid 65), wherein at least one of the polypeptides includes prior to contacting, phosphorylated N-glycans comprising uncapped mannose-6-phosphate moieties. The mannosidase can be a family 47 glycosyl hydrolase (e.g., an *Aspergillus satoi* mannosidase), a family 92 glycosyl hydrolase (e.g., a *Cellulosimicrobium cellulans* mannosidase), or a family 38 glycosyl hydrolase (e.g., a *Canavalia ensiformis* mannosidase). The contacting can occur in a recombinant fungal cell expressing the mannosidase.

This document also features a method of making a molecular complex that includes uncapped and demannosylated phosphorylated N-glycans. The method includes contacting a molecular complex with a mannosidase capable of hydrolyzing a mannose-1-phospho-6-mannose moiety to mannose-6-phosphate, the molecular complex having GAA activity and including at least two polypeptides, each polypeptide having at least 85% sequence identity to a segment of the amino acid sequence set forth in SEQ ID NO: 1, each segment being derived by proteolysis of the amino acid sequence set forth in SEQ ID NO: 1 at one or more sites between amino acid 50 and amino acid 74 (e.g., between amino acid 56 and amino acid 68 or between amino acid 60 and amino acid 65), wherein at least one of the polypeptides includes, before the contacting, one or more mannose-1-phospho-6-mannose moieties. The mannosidase can be a family 38 glycosyl hydrolase (e.g., a *Canavalia ensiformis* mannosidase or a *Yarrowia lipolytica* mannosidase).

In another aspect, this document features a method of making a molecular complex that includes uncapped and demannosylated phosphorylated N-glycans. The method includes a) contacting a molecular complex with a mannosidase capable of hydrolyzing a mannose-1-phospho-6-mannose moiety to mannose-6-phosphate to uncap mannose-6-phosphate moieties on at least one polypeptide in the molecular complex, the molecular complex having GAA activity and comprising at least two polypeptides, each polypeptide having at least 85% sequence identity to a segment of the amino acid sequence set forth in SEQ ID NO: 1, each segment being derived by proteolysis of the amino acid sequence set forth in SEQ ID NO: 1 at one or more sites between amino acid 50 and amino acid 74 (e.g., between amino acid 56 and amino acid 68 or between amino acid 60 and amino acid 65); and b) contacting the molecular complex with a mannosidase capable of hydrolyzing terminal alpha-1,2 mannose, alpha-1,3 mannose and/or alpha-1,6 mannose linkages. Step (a) and step (b) can be catalyzed by two different enzymes or catalyzed by a single enzyme. The contacting steps can be performed together or separately, and in either order. The contacting can occur in a recombinant fungal host cell, the fungal host cell expressing a mannosidase capable of catalyzing step (a) and a mannosidase capable of catalyzing step (b). The contacting can occur in a recombinant fungal host cell, the fungal host expressing a mannosidase capable of catalyzing steps (a) and (b).

Any of the molecular complexes described herein that include at least one uncapped and demannosylated N-glycan can be used to contact a mammalian cell, wherein, after the contacting, the molecular complex is transported to the interior of the mammalian cell with enhanced efficiency. The mammalian cell can be a human cell.

This document also features a method of transporting a molecular complex having GAA activity to the interior of a cell. The method includes contacting a mammalian cell with the molecular complex, the molecular complex including at least two polypeptides, each polypeptide having at least 85% sequence identity to a segment of the amino acid sequence set forth in SEQ ID NO: 1, each segment being derived by proteolysis of the amino acid sequence set forth in SEQ ID NO: 1 at one or more sites between amino acid 50 and amino acid 74 (e.g., between amino acid 56 and amino acid 68 or between amino acid 60 and amino acid 65); wherein phosphorylated N-glycans on at least one of the polypeptides have been uncapped and demannosylated as set forth in the methods described herein. The mammalian cell can be in vitro or in a mammalian subject. The mammalian cell can be a human cell.

In another aspect, this document features a method of transporting a molecular complex having GAA activity to the interior of a cell. The method includes contacting a mammalian cell with the molecular complex that includes at least two polypeptides, each polypeptide having at least 85% sequence identity to a segment of the amino acid sequence set forth in SEQ ID NO: 1, each segment being derived by proteolysis of the amino acid sequence set forth in SEQ ID NO: 1 at one or more sites between amino acid 50 and amino acid 74 (e.g., between amino acid 56 and amino acid 68 or between amino acid 60 and amino acid 65), the molecular complex comprising at least one modification that results in enhanced ability of the molecular complex to be transported to the interior of a mammalian cell. The mammalian cell can be in vitro or in a mammalian subject. The mammalian cell can be a human cell. The modification can include any one of the following fused to at least one polypeptide in the molecular complex: a ligand for an extracellular receptor, a targeting domain that binds an extracellular domain of a receptor on the surface of a target cell, a urokinase-type plasminogen receptor, or the recognition domain of human insulin-like growth factor II.

In another aspect, this document features an isolated fungal cell that includes an exogenous nucleic acid encoding an alkaline protease having at least 85% sequence identity to the amino acid sequence set forth in SEQ ID NO:8.

This document also features an isolated fungal cell comprising a nucleic acid encoding the GAA amino acid sequence set forth in SEQ ID NO:1 and a nucleic acid encoding an alkaline protease having at least 85% sequence identity to the amino acid sequence set forth in SEQ ID NO:8. The fungal cell produces a molecular complex having GAA activity and comprising at least two polypeptides, each polypeptide having at least 85% sequence identity to a segment of the amino acid sequence set forth in SEQ ID NO: 1, each segment being derived by proteolysis of the amino acid sequence set forth in SEQ ID NO: 1 at one or more sites between amino acid 50 and amino acid 74 (e.g., between amino acid 56 and amino acid 68 or between amino acid 60 and amino acid 65) by the alkaline protease. In some embodiments, the fungal cell further comprises a nucleic acid encoding a mannosidase, the mannosidase being capable of hydrolyzing a mannose-1-phospho-6-mannose moiety to mannose-6-phosphate. In some embodiments, the fungal cell further includes a nucleic acid encoding a mannosidase, the mannosidase being capable of hydrolyzing a terminal alpha-1,2 mannose, alpha-1,3 mannose and/or alpha-1,6 mannose linkage. In some embodiments, the fungal cell further can include a nucleic acid encoding a mannosidase, the mannosidase being capable of (i) hydrolyzing a mannose-1-phospho-6-mannose moiety to mannose-6-phosphate and (ii) hydrolyzing a terminal alpha-1,2 mannose, alpha-1,3 mannose and/or alpha-1,6 mannose linkage. Any of such fungal cells further can include a nucleic acid encoding a polypeptide capable of promoting mannosyl phosphorylation and/or be genetically engineered to be deficient in OCH1 activity.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, the exemplary methods and materials are described below. All publications, patent applications, patents, Genbank® Accession Nos, and other references mentioned herein are incorporated by reference in their entirety. In case of conflict, the present application, including definitions, will control. The materials, methods, and examples are illustrative only and not intended to be limiting.

Other features and advantages of the invention will be apparent from the following detailed description, and from the claims.

DESCRIPTION OF DRAWINGS

FIG. 1 is a depiction of the amino acid sequence (SEQ ID NO:1) of human acid alpha glucosidase (GAA) after cleavage of the signal sequence.

FIG. 2A is a depiction of the nucleotide sequence of the open reading frame (ORF) of DsbA-*Cellulosimicrobium cellulans* mannosidase 5 (CcMan5) (SEQ ID NO:2).

FIG. 2B is a depiction of the amino acid sequence of the CcMan5 polypeptide with the signal sequence in bold (SEQ ID NO: 3).

FIG. 2C is a depiction of the amino acid sequence of the CcMan5 polypeptide without signal sequence (SEQ ID NO:4). The predicted molecular weight of the CcMan5 polypeptide without the signal sequence is 173 kDa.

In FIG. 3A, panels B and C contain the N-glycan analysis from huGAA (76 kD variant) before and after treatment, respectively, with CcMan5 and JbMan. In FIG. 3B, panels B, C, and D contain the N-glycan analysis from huGAA 76 kD form, 95 kD form, and 110 kD form, respectively.

FIG. 6 contains a depiction of the amino acid sequence of the *Yarrowia lipolytica* AMS1 mannosidase (SEQ ID NO: 5).

FIG. 7 contains a depiction of the amino acid sequence of the *Aspergillus satoi* mannosidase (SEQ ID NO:6).

FIG. 8 contains a depiction of the amino acid sequence of the *Cellulosimicrobium cellulans* mannosidase 4 (CcMan4, SEQ ID NO:7), with signal sequence in bold. The predicted molecular weight of the CcMan4 polypeptide without the signal sequence is 184 kDa.

FIG. 9 contains a depiction of the amino acid sequence of the *Aspergillus oryzae* alkaline protease including the signal peptide (21 amino acids), pro-peptide (100 amino acids) and mature protein (282 amino acids) (SEQ ID NO:9).

FIG. 10 contains a depiction of the nucleotide sequence of the fusion construct containing the *Y. lipolytica* codon optimized sequence encoding the *A. oryzae* alkaline protease (SEQ ID NO:10). Restriction sites used for cloning are underlined. The nucleotide sequence encoding the linker is in bold and the nucleotide sequence encoding the His tag (10 His residues) is italicized.

DETAILED DESCRIPTION

Figure 3A:
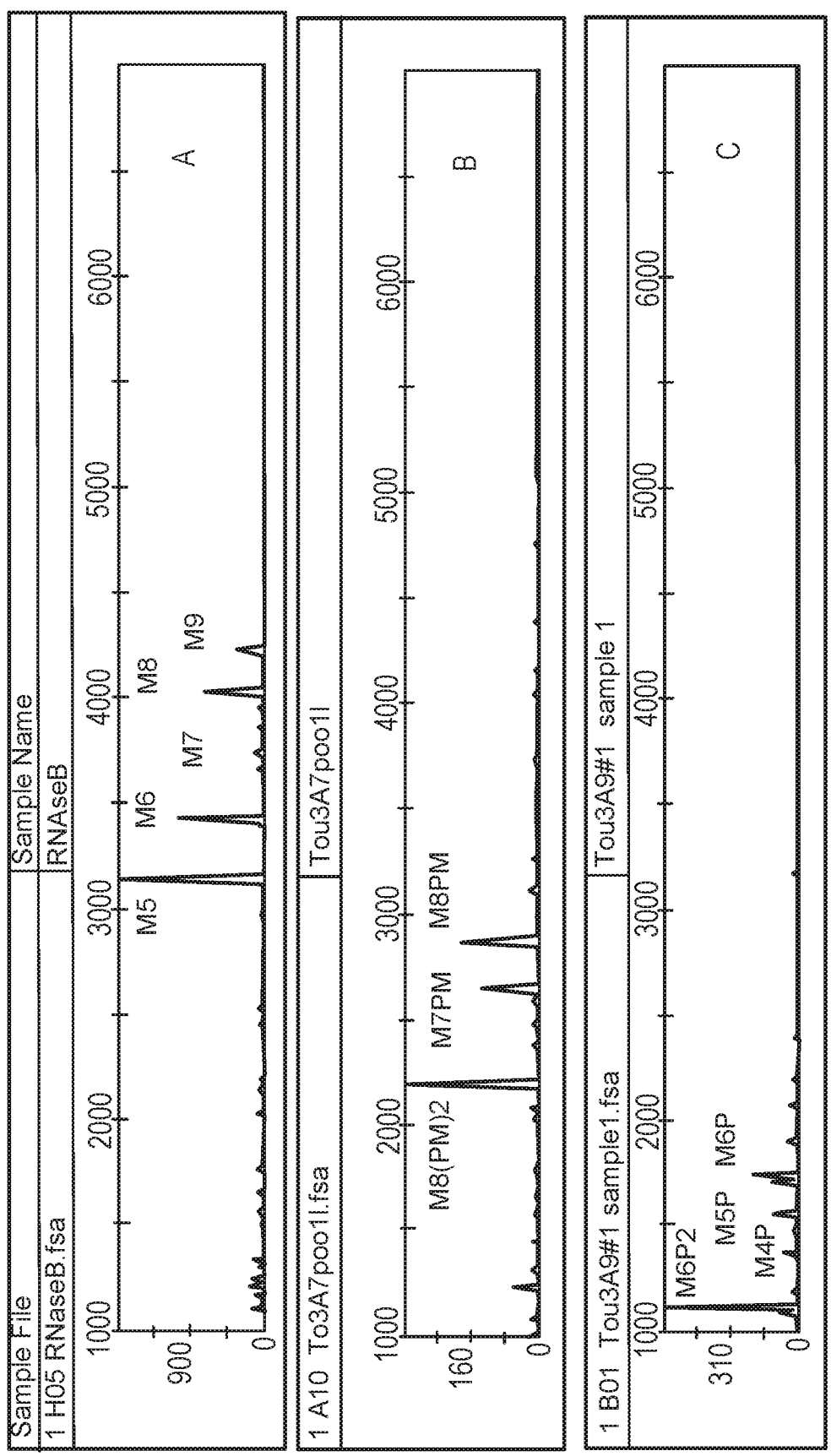
FIGS. 3A and 3B are a series of electropherograms depicting the N-glycan analysis of rhGAA treated with CcMan5 and JbMan. Analysis was performed using DNA sequencer-assisted, fluorophore-assisted carbohydrate electrophoresis (DSA-FACE). The Y-axis represents the relative fluorescence units as an indication of the amount of each N-glycan structure. The X-axis represents the relative mobility of each N-glycan structure through a capillary. In both FIG. 3A and FIG. 3B, panel A is a reference sample containing the N-glycans released from RNaseB with PNGaseF.

In general, this document provides isolated molecular complexes having acid alpha-glucosidase (GAA) activity and at least one modification that results in an enhanced ability to be transported to the interior of a mammalian cell. GAA is synthesized as a 110 kDa precursor containing N-linked glycans. The precursor is proteolytically processed to remove the signal sequence and then further proteolytically processed to major species of 95 kDa, 76 kDa, and 70 kDa. However, at least some of the peptides that are released from the precursor remain associated with the major species. See, for example, Moreland et al., *J. Biol. Chem.*, 280:6780-6791 (2005). Thus, the molecular complexes having GAA activity described herein include at least two polypeptides (at least two, three, or four polypeptides) that are derived from proteolytic cleavage of the precursor molecule at one or more sites. At least two polypeptides in the molecular complex result from proteolytic cleavage at one or more sites in the precursor. For example, proteolysis of the amino acid sequence set forth in SEQ ID NO:1 can be between amino acid 50 and amino acid 74, e.g., between amino acid 56 and amino acid 68 or between amino acid 60 and amino acid 65, to produce at least two polypeptides. A molecular complex containing two polypeptides is referred to as the 95 kDa form herein.

In some embodiments, at least three polypeptides in the molecular complex result from proteolytic cleavage at two or more sites in the precursor. For example, proteolysis of the amino acid sequence set forth in SEQ ID NO:1 can include, in addition to cleavage between amino acid 50 and amino acid 74 (e.g., between amino acid 56 and amino acid 68 or between amino acid 60 and amino acid 65), cleavage at one or more sites between amino acid 719 and amino acid 746 or cleavage at one or more sites between amino acid 137 and amino acid 151 of the amino acid sequence set forth in SEQ ID NO:1. A molecular complex containing three polypeptides is referred to as the 76 kDa form herein.

In some embodiments, at least four polypeptides in the molecular complex result from proteolytic cleavage at three or more sites in the precursor. For example, proteolysis of the amino acid sequence set forth in SEQ ID NO:1 can include, in addition to the cleavage between amino acid 50 and amino acid 74 (e.g., between amino acid 56 and amino acid 68 or between amino acid 60 and amino acid 65), cleavage at one or more sites between amino acid 719 and amino acid 746 of the amino acid sequence set forth in SEQ ID NO:1 and cleavage at one or more sites between amino acid 137 and amino acid 151 of the amino acid sequence set forth in SEQ ID NO:1. A molecular complex containing four polypeptides is referred to as the 70 kDa form herein.

It will be appreciated that cleavage can occur at one or more sites in one molecule, and that the site of cleavage can be different in different molecules.

A commercially available protease mix containing proteases from *Aspergillus oryzae* (e.g., from Sigma or Novozymes Corp) can be used to cleave the amino acid sequence set forth in SEQ ID NO:1 between amino acids 50 and 74, e.g., between amino acids 56 and 68 or between amino acids 60 and 65. Alternatively, an alkaline protease having at least 85% (e.g., at least 90%, 95%, 97%, 98%, 99%, or 100%) sequence identity to the alkaline protease from *Aspergillus oryzae* (SEQ ID NO:8) can be used. For example, as described herein, a GAA polypeptide having the amino acid sequence set forth in SEQ ID NO:1 can be contacted with a protease having at least 85% sequence identity to the amino acid sequence set forth in SEQ ID NO:8 or SEQ ID NO: 9. SEQ ID NO: 8 is the amino acid sequence of the mature *Aspergillus oryzae* alkaline protease. SEQ ID NO: 9 is the amino acid sequence of the *Aspergillus oryzae* protease including the signal peptide, pro-peptide, and mature protein. The contacting can occur in vitro using protease that has been isolated from *Aspergillus oryzae* or that has been recombinantly produced. Alternatively, a fungal host can be engineered such that the GAA polypeptide and alkaline protease are both secreted into the culture medium, where the alkaline protease can cleave the amino acid sequence set forth in SEQ ID NO:1 between amino acid 50 and amino acid 74 (e.g., between amino acids 56 and 68 or between amino acids 60 and 65).

The isolated molecular complexes described herein have at least one modification that results in an enhanced ability to be transported to the interior of a mammalian cell. Non-limiting examples of modifications that enhance the ability of the complex of being transported to the interior of a mammalian cell include uncapping and demannosylation of phosphorylated N-glycans or peptide tags that facilitate transport. Methods and materials are described herein for preparing molecular complexes containing tags or uncapped and demannosylated N-glycans.

The isolated molecular complexes described herein are particularly useful for treating patients with Pompe disease, including a patient diagnosed with Pompe's disease, both infantile onset Pompe's disease and late onset Pompe's disease. Pompe's disease results in an accumulation of glycogen in the lysosome due to a deficiency of GAA. The build-up of glycogen causes progressive muscle weakness (myopathy) throughout the body and affects various body tissues, including the heart, skeletal muscles, live, and nervous system.

Each of the polypeptide in the molecular complex have at least 85% sequence identity (e.g., at least 90%, 95%, 97%, 98%, 99%, or 100%) to a segment of the amino acid sequence set forth in SEQ ID NO: 1, each segment being derived by proteolysis of the amino acid sequence set forth in SEQ ID NO: 1 at one or more sites between amino acid 50 and amino acid 74 (e.g., between amino acid 56 and amino acid 68 or between amino acid 60 and amino acid 65). The percent identity between a particular amino acid sequence and the amino acid sequence set forth in SEQ ID NO: 1 can be determined as follows. First, the amino acid sequences are aligned using the BLAST 2 Sequences (Bl2seq) program from the stand-alone version of BLASTZ containing BLASTP version 2.0.14. This stand-alone version of BLASTZ can be obtained from Fish & Richardson's web site (e.g., www.fr.com/blast/) or the U.S. government's National Center for Biotechnology Information web site (www.ncbi.nlm.nih.gov). Instructions explaining how to use the Bl2seq program can be found in the readme file accompanying BLASTZ. Bl2seq performs a comparison between two amino acid sequences using the BLASTP algorithm. To compare two amino acid sequences, the options of Bl2seq are set as follows: -i is set to a file containing the first amino acid sequence to be compared (e.g., C:\seq1.txt); -j is set to a file containing the second amino acid sequence to be compared (e.g., C:\seq2.txt); -p is set to blastp; -o is set to any desired file name (e.g., C:\output.txt); and all other options are left at their default setting. For example, the following command can be used to generate an output file containing a comparison between two amino acid sequences: C:\Bl2seq -i c:\seq1.txt -j c:\seq2.txt -p blastp -o c:\output.txt. If the two compared sequences share homology, then the designated output file will present those regions of homology as aligned sequences. If the two compared sequences do not share homology, then the designated output file will not present aligned sequences. Similar procedures can be following for nucleic acid sequences except that blastn is used.

Once aligned, the number of matches is determined by counting the number of positions where an identical amino acid residue is presented in both sequences. The percent identity is determined by dividing the number of matches by the length of the full-length polypeptide amino acid sequence followed by multiplying the resulting value by 100.

It is noted that the percent identity value is rounded to the nearest tenth. For example, 78.11, 78.12, 78.13, and 78.14 is rounded down to 78.1, while 78.15, 78.16, 78.17, 78.18, and 78.19 is rounded up to 78.2. It also is noted that the length value will always be an integer.

It will be appreciated that a number of nucleic acids can encode a polypeptide having a particular amino acid sequence. The degeneracy of the genetic code is well known to the art; i.e., for many amino acids, there is more than one nucleotide triplet that serves as the codon for the amino acid. For example, codons in the coding sequence for a given GAA polypeptide can be modified such that optimal expression in a particular species (e.g., bacteria or fungus) is obtained, using appropriate codon bias tables for that species.

In one embodiment, a molecular complex can include at least two polypeptides, where one of the polypeptides includes amino acids 22 to 57 of SEQ ID NO:1, and another polypeptide includes amino acids 66 to 896 of SEQ ID NO:1.

In one embodiment, a molecular complex can include at least three polypeptides, wherein one of the polypeptides includes amino acids 22 to 57 of SEQ ID NO:1, one polypeptide includes amino acids 66 to 726 of SEQ ID NO:1, and one polypeptide includes amino acids 736 to 896 of SEQ ID NO:1.

In one embodiment, a molecular complex can include at least four polypeptides, wherein one of the polypeptides includes amino acids 22 to 57 of SEQ ID NO:1, one polypeptide includes amino acids 66 to 143 of SEQ ID NO:1, one polypeptide includes amino acids 158 to 726 of SEQ ID NO:1, and one polypeptide includes amino acids 736 to 896 of SEQ ID NO:1.

Biologically active variants of GAA can contain additions, deletions, or substitutions relative to the sequences set forth in SEQ ID NO: 1. GAA proteins with substitutions will generally have not more than 10 (e.g., not more than one, two, three, four, five, six, seven, eight, nine, or ten) conservative amino acid substitutions. A conservative substitution is the substitution of one amino acid for another with similar characteristics. Conservative substitutions include substitutions within the following groups: valine, alanine and glycine; leucine, valine, and isoleucine; aspartic acid and glutamic acid; asparagine and glutamine; serine, cysteine, and threonine; lysine and arginine; and phenylalanine and tyrosine. The non-polar hydrophobic amino acids include alanine, leucine, isoleucine, valine, proline, phenylalanine, tryptophan and methionine. The polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid. Any substitution of one member of the above-mentioned polar, basic or acidic groups by another member of the same group can be deemed a conservative substitution. By contrast, a non-conservative substitution is a substitution of one amino acid for another with dissimilar characteristics.

In some embodiments, a GAA polypeptide can be a fusion protein with a heterologous amino acid sequence such as a sequence used for purification of the recombinant protein (e.g., FLAG, polyhistidine (e.g., hexahistidine), hemaglutanin (HA), glutathione-S-transferase (GST), or maltose-binding protein (MBP)).

In some embodiments, the heterologous amino acid sequence is used to enhance the efficiency of transport of the molecular complex into a mammalian cell. For example, at least one of the polypeptides in a complex can be fused to a ligand for an extracellular receptor, a targeting domain that binds an extracellular domain of a receptor on the surface of a target cell, a urokinase-type plasminogen receptor, or domains of human insulin-like growth factor II that bind to the mannose-6-phosphate receptor (e.g., amino acids 1-67 or 1-87; at least amino acids 48-55; at least amino acids 8-28 and 41-61; or at least amino acids 8-87 of human insulin-like growth factor; a sequence variant thereof of human insulin-like growth factor II (e.g., R68A) or truncated form of human insulin-like growth factor (e.g., C-terminally truncated from position 62)). The heterologous amino acid sequence can be fused at the N-terminus or C-terminus of the polypeptide. In one embodiment, a peptide tag is fused to the N- or C-terminus of the polypeptide by a spacer (e.g., 5-30 amino acids or 10-25 amino acids). See, for example, U.S. Pat. No. 7,785,856.

Heterologous amino sequences also can be proteins useful as diagnostic or detectable markers, for example, luciferase, green fluorescent protein (GFP), or chloramphenicol acetyl transferase (CAT).

In certain host cells (e.g., yeast host cells), expression and/or secretion of the target protein can be increased through use of a heterologous signal sequence. In some embodiments, the fusion protein can contain a carrier (e.g., KLH) useful, e.g., in eliciting an immune response for antibody generation) or endoplasmic reticulum or Golgi apparatus retention signals. Heterologous sequences can be of varying length and in some cases can be a longer sequences than the full-length target proteins to which the heterologous sequences are attached.

Methods of Demannosylating, or Uncapping and Demannosylating Glycoproteins

Glycoproteins containing a phosphorylated N-glycan can be demannosylated, and glycoproteins containing a phosphorylated N-glycan containing a mannose-1-phospho-6-mannose linkage or moiety can be uncapped and demannosylated by contacting the glycoprotein with a mannosidase capable of (i) hydrolyzing a mannose-1-phospho-6-mannose linkage or moiety to mannose-6-phosphate and (ii) hydrolyzing a terminal alpha-1,2 mannose, alpha-1,3 mannose and/or alpha-1,6 mannose linkage or moiety. Non-limiting examples of such mannosidases include a *Canavalia ensiformis* (Jack bean) mannosidase and a *Yarrowia lipolytica* mannosidase (e.g., AMS1). Both the Jack bean and AMS1 mannosidase are family 38 glycoside hydrolases.

The Jack bean mannosidase is commercially available, for example, from Sigma-Aldrich (St. Louis, Mo.) as an ammonium sulfate suspension (Catalog No. M7257) and a proteomics grade preparation (Catalog No. M5573). Such commercial preparations can be further purified, for example, by gel filtration chromatography to remove contaminants such as phosphatases. The Jack bean mannosidase contains a segment with the following amino acid sequence NKIPRAGWQIDPFGHSAVQG (SEQ ID NO: 11). See Howard et al., *J. Biol. Chem.*, 273(4):2067-2072, 1998.

The *Yarrowia lipolytica* AMS1 mannosidase can be recombinantly produced. The amino acid sequence of the AMS1 polypeptide is set forth in SEQ ID NO:5 (see also FIG. 6).

In some embodiments, the uncapping and demannosylating steps are catalyzed by two different enzymes. For example, uncapping of a mannose-1-phospho-6 mannose linkage or moiety can be performed using a mannosidase from *Cellulosimicrobium cellulans* (e.g., CcMan5). The nucleotide sequence encoding the CcMan5 polypeptide is set forth in SEQ ID NO:2 (see FIG. 2A). The amino acid sequence of the CcMan5 polypeptide containing signal sequence is set forth in SEQ ID NO: 3 (see FIG. 2B). The amino acid sequence of the CcMan5 polypeptide without signal sequence is set forth in SEQ ID NO:4 (see FIG. 2C). In some embodiments, a biologically active fragment of the CcMan5 polypeptide is used. For example, a biologically active fragment can includes residues 1-774 of the amino acid sequence set forth in SEQ ID NO:4. See also WO 2011/039634. The CcMan5 mannosidase is a family 92 glycoside hydrolase.

Demannosylation of an uncapped glycoprotein or molecular complexes of glycoproteins can be catalyzed using a mannosidase from *Aspergillus satoi* (As) (also known as *Aspergillus phoenicis*) or a mannosidase from *Cellulosimicrobium cellulans* (e.g., CcMan4). The *Aspergillus satoi* mannosidase is a family 47 glycoside hydrolase and the CcMan4 mannosidase is a family 92 glycoside hydrolase. The amino acid sequence of the *Aspergillus satoi* mannosidase is set forth in FIG. 7 (SEQ ID NO:6) and in GenBank Accession No. BAA08634. The amino acid sequence of the CcMan4 polypeptide is set forth in FIG. 8 (SEQ ID NO:7).

Demannosylation of an uncapped glycoprotein or molecular complexes of glycoproteins also can be catalyzed using a mannosidase from the family 38 glycoside hydrolases such as a *Canavalia ensiformis* (Jack bean) mannosidase or a *Yarrowia lipolytica* mannosidase (e.g., AMS1). For example, CcMan5 can be used to uncap a mannose-1-phospho-6 mannose moiety on a glycoprotein (or molecular complex of glycoproteins) and the Jack bean mannosidase can be used to demannosylate the uncapped glycoprotein (or molecular complex of glycoproteins).

To produce demannosylated glycoproteins (or molecular complexes of glycoproteins), or uncapped and demannosylated glycoproteins (or molecular complexes of glycoproteins), a target molecule (or molecular complex) containing a mannose-1-phospho-6 mannose linkage or moiety is contacted under suitable conditions with a suitable mannosidase(s) and/or a cell lysate containing a suitable recombinantly produced mannosidase(s). Suitable mannosidases are described above. The cell lysate can be from any genetically engineered cell, including a fungal cell, a plant cell, or animal cell. Non-limiting examples of animal cells include nematode, insect, plant, bird, reptile, and mammals such as a mouse, rat, rabbit, hamster, gerbil, dog, cat, goat, pig, cow, horse, whale, monkey, or human.

Upon contacting the target molecule (e.g., molecular complex) with the purified mannosidases and/or cell lysate, the mannose-1-phospho-6-mannose linkage or moiety can be hydrolyzed to phospho-6-mannose and the terminal alpha-1,2 mannose, alpha-1,3 mannose and/or alpha-1,6 mannose linkage or moiety of such a phosphate containing glycan can be hydrolyzed to produces an uncapped and demannosylated target molecule. In some embodiments, one mannosidase is used that catalyzes both the uncapping and demannosylating steps. In some embodiments, one mannosidase is used to catalyze the uncapping step and a different mannosidase is used to catalyze the demannosylating step. Following processing by the mannosidase, the target molecule or molecular complex can be isolated.

Suitable methods for obtaining cell lysates that preserve the activity or integrity of the mannosidase activity in the lysate can include the use of appropriate buffers and/or inhibitors, including nuclease, protease and phosphatase inhibitors that preserve or minimize changes in N-glycosylation activities in the cell lysate. Such inhibitors include, for example, chelators such as ethylenediamine tetraacetic acid (EDTA), ethylene glycol bis(P-aminoethyl ether) N,N,N1,N1-tetraacetic acid (EGTA), protease inhibitors such as phenylmethylsulfonyl fluoride (PMSF), aprotinin, leupeptin, antipain and the like, and phosphatase inhibitors such as phosphate, sodium fluoride, vanadate and the like. Appropriate buffers and conditions for obtaining lysates containing enzymatic activities are described in, e.g., Ausubel et al. Current Protocols in Molecular Biology (Supplement 47), John Wiley & Sons, New York (1999); Harlow and Lane, Antibodies: A Laboratory Manual Cold Spring Harbor Laboratory Press (1988); Harlow and Lane, Using Antibodies: A Laboratory Manual, Cold Spring Harbor Press (1999); Tietz Textbook of Clinical Chemistry, 3rd ed. Burtis and Ashwood, eds. W.B. Saunders, Philadelphia, (1999).

A cell lysate can be further processed to eliminate or minimize the presence of interfering substances, as appropriate. If desired, a cell lysate can be fractionated by a variety of methods well known to those skilled in the art, including subcellular fractionation, and chromatographic techniques such as ion exchange, hydrophobic and reverse phase, size exclusion, affinity, hydrophobic charge-induction chromatography, and the like.

In some embodiments, a cell lysate can be prepared in which whole cellular organelles remain intact and/or functional. For example, a lysate can contain one or more of intact rough endoplasmic reticulum, intact smooth endoplasmic reticulum, or intact Golgi apparatus. Suitable methods for preparing lysates containing intact cellular organelles and testing for the functionality of the organelles are described in, e.g., Moreau et al. (1991) *J. Biol. Chem.* 266(7):4329-4333; Moreau et al. (1991) *J. Biol. Chem.* 266(7):4322-4328; Rexach et al. (1991) *J. Cell Biol.* 114 (2):219-229; and Paulik et al. (1999) *Arch. Biochem. Biophys.* 367(2):265-273.

Upon contact of a mammalian cell with a molecular complex containing uncapped and demannosylated phosphorylated N-glycans, the molecular complex can be transported to the interior of the mammalian cell (e.g., a human cell). A molecular complex having an uncapped, but not demannosylated, phosphorylated N-glycan does not substantially bind mannose-6-phosphate receptors on mammalian cells, and as such, is not efficiently transported to the interior of the cell. As used herein, "does not substantially bind" means that less than 15% (e.g., less than 14%, 12%, 10%, 8%, 6%, 4%, 2%, 1%, 0.5%, or less, or 0%) of the glycoprotein molecules bind to mannose-6-phosphate receptors on mammalian cells. However, if such a molecular complex is contacted with a mannosidase capable of hydrolyzing a terminal alpha-1,2 mannose linkage or moiety when the underlying mannose is phosphorylated, a demannosylated glycoprotein is produced that substantially binds to the mannose-6-phosphate receptor on the mammalian cells and is efficiently transported to the interior of the cell. As used herein "substantially binds" means that 15% or more (e.g., greater than 16%, 18%, 20%, 25%, 30%, 35%, 40%, 45%, 50%, 55%, 60%, 65%, 70%, 75%, 80%, 85%, 90% or 95%) of the molecular complex binds to mannose-6-phosphate receptors on mammalian cells. It is understood that a preparation (e.g., a recombinant host cell or a cell-free preparation) containing an enzyme that uncaps but does not demannosylate phosphorylated N-glycans could be contaminated with an enzyme that demannosylates phosphorylated N-glycans. A target protein sample after contact with such a preparation can contain protein molecules with some phosphorylated N-glycans that are uncapped only and others that are uncapped and demannosylated. Naturally those protein molecules containing uncapped and demannosylated phosphorylated N-glycans can substantially bind to mannose-6-phosphate receptors. The above definition of "does not substantially bind" does not apply to such a target protein sample since the phosphorylated N-glycans on the protein molecules cannot be characterized as uncapped but not demannosylated.

Thus, this document provides methods of converting a molecular complex from a first form that does not bind to a mannose-6-phosphate receptor on a mammalian cell to a second form that does bind to a mannose-6-phosphate receptor on a mammalian cell. In the first form, the molecular complex in which at least one of the polypeptides in the complex comprises one or more N-glycans containing one or more mannose residues that are linked at the 1 position to a mannose residue that contains a phosphate residue at the 6 position. In such methods, the first form of the molecular complex is contacted with a mannosidase that demannosylates the terminal mannose residues to result in the mannose containing the phosphate at the 6 position to become the terminal mannose. In some embodiments, the mannosidase has both uncapping and demannosylating activity (e.g., *Canavalia ensiformis* (Jack bean) or *Yarrowia lipolytica* AMS1 mannosidase). In some embodiments, the mannosidase does not have uncapping activity (e.g., a mannosidase from *Aspergillus satoi* or a mannosidase from *Cellulosimicrobium cellulans* (e.g., CcMan4)).

Transport of a glycoprotein or molecular complex to the interior of the cell can be assessed using a cell uptake assay. For example, mammalian cells and a molecular complex containing uncapped and demannosylated phosphorylated N-glycans can be incubated, then the cells washed and lysed. Cell lysates can be assessed for the presence of the GAA complex (e.g., by Western blotting) or by activity of GAA in the cell lysate. For example, uptake can be assessed in fibroblasts deficient in acid alpha glucosidase activity. Intracellular activity of alpha glucosidase can be assessed using the 4-methylumbelliferyl-alpha-D-glucopyranoside (4-MUG) assay. Cleavage of the substrate 4-MUG by a glucosidase leads to the generation of the fluorigenic product 4-MU, which can be visualized or detected by irradiation with UV light.

Recombinant Production of Polypeptides

Isolated nucleic acid molecules encoding polypeptides (e.g., a mannosidase, an alkaline protease, or GAA or a fragment thereof) can be produced by standard techniques. The terms "nucleic acid" and "polynucleotide" are used interchangeably herein, and refer to both RNA and DNA, including cDNA, genomic DNA, synthetic DNA, and DNA (or RNA) containing nucleic acid analogs. Polynucleotides can have any three-dimensional structure. A nucleic acid can be double-stranded or single-stranded (i.e., a sense strand or an antisense strand). Non-limiting examples of polynucleotides include genes, gene fragments, exons, introns, messenger RNA (mRNA), transfer RNA, ribosomal RNA, siRNA, micro-RNA, ribozymes, cDNA, recombinant polynucleotides, branched polynucleotides, plasmids, vectors, isolated DNA of any sequence, isolated RNA of any sequence, nucleic acid probes, and primers, as well as nucleic acid analogs.

An "isolated nucleic acid" refers to a nucleic acid that is separated from other nucleic acid molecules that are present in a naturally-occurring genome, including nucleic acids that normally flank one or both sides of the nucleic acid in a naturally-occurring genome (e.g., a yeast genome). The term "isolated" as used herein with respect to nucleic acids also includes any non-naturally-occurring nucleic acid sequence, since such non-naturally-occurring sequences are not found in nature and do not have immediately contiguous sequences in a naturally-occurring genome.

An isolated nucleic acid can be, for example, a DNA molecule, provided one of the nucleic acid sequences normally found immediately flanking that DNA molecule in a naturally-occurring genome is removed or absent. Thus, an isolated nucleic acid includes, without limitation, a DNA molecule that exists as a separate molecule (e.g., a chemically synthesized nucleic acid, or a cDNA or genomic DNA fragment produced by PCR or restriction endonuclease treatment) independent of other sequences as well as DNA that is incorporated into a vector, an autonomously replicating plasmid, a virus (e.g., any paramyxovirus, retrovirus, lentivirus, adenovirus, or herpes virus), or into the genomic DNA of a prokaryote or eukaryote. In addition, an isolated nucleic acid can include an engineered nucleic acid such as a DNA molecule that is part of a hybrid or fusion nucleic acid. A nucleic acid existing among hundreds to millions of other nucleic acids within, for example, cDNA libraries or genomic libraries, or gel slices containing a genomic DNA restriction digest, is not considered an isolated nucleic acid.

The term "exogenous" as used herein with reference to nucleic acid and a particular host cell refers to any nucleic acid that does not occur in (and cannot be obtained from) that particular cell as found in nature. Thus, a non-naturally-occurring nucleic acid is considered to be exogenous to a host cell once introduced into the host cell. It is important to note that non-naturally-occurring nucleic acids can contain nucleic acid subsequences or fragments of nucleic acid sequences that are found in nature provided that the nucleic acid as a whole does not exist in nature. For example, a nucleic acid molecule containing a genomic DNA sequence within an expression vector is non-naturally-occurring nucleic acid, and thus is exogenous to a host cell once introduced into the host cell, since that nucleic acid molecule as a whole (genomic DNA plus vector DNA) does not exist in nature. Thus, any vector, autonomously replicating plasmid, or virus (e.g., retrovirus, adenovirus, or herpes virus) that as a whole does not exist in nature is considered to be non-naturally-occurring nucleic acid. It follows that genomic DNA fragments produced by PCR or restriction endonuclease treatment as well as cDNAs are considered to be non-naturally-occurring nucleic acid since they exist as separate molecules not found in nature. It also follows that any nucleic acid containing a promoter sequence and polypeptide-encoding sequence (e.g., cDNA or genomic DNA) in an arrangement not found in nature is non-naturally-occurring nucleic acid. A nucleic acid that is naturally-occurring can be exogenous to a particular cell. For example, an entire chromosome isolated from a cell of yeast x is an exogenous nucleic acid with respect to a cell of yeast y once that chromosome is introduced into a cell of yeast y.

Polymerase chain reaction (PCR) techniques can be used to obtain an isolated nucleic acid containing a nucleotide sequence described herein. PCR can be used to amplify specific sequences from DNA as well as RNA, including sequences from total genomic DNA or total cellular RNA. Generally, sequence information from the ends of the region of interest or beyond is employed to design oligonucleotide primers that are identical or similar in sequence to opposite strands of the template to be amplified. Various PCR strategies also are available by which site-specific nucleotide sequence modifications can be introduced into a template nucleic acid. Isolated nucleic acids also can be chemically synthesized, either as a single nucleic acid molecule (e.g., using automated DNA synthesis in the 3' to 5' direction using phosphoramidite technology) or as a series of oligonucleotides. For example, one or more pairs of long oligonucleotides (e.g., >100 nucleotides) can be synthesized that contain the desired sequence, with each pair containing a short segment of complementarity (e.g., about 15 nucleotides) such that a duplex is formed when the oligonucleotide pair is annealed. DNA polymerase is used to extend the oligonucleotides, resulting in a single, double-stranded nucleic acid molecule per oligonucleotide pair, which then can be ligated into a vector. Isolated nucleic acids also can be obtained by mutagenesis of, e.g., a naturally occurring DNA.

To recombinantly produce a polypeptide (e.g., a mannosidase, an alkaline protease, or GAA or fragment thereof), a vector is used that contains a promoter operably linked to nucleic acid encoding the polypeptide. As used herein, a "promoter" refers to a DNA sequence that enables a gene to be transcribed. The promoter is recognized by RNA polymerase, which then initiates transcription. Thus, a promoter contains a DNA sequence that is either bound directly by, or is involved in the recruitment, of RNA polymerase. A promoter sequence can also include "enhancer regions," which are one or more regions of DNA that can be bound with proteins (namely, the trans-acting factors, much like a set of transcription factors) to enhance transcription levels of genes (hence the name) in a gene-cluster. The enhancer, while typically at the 5' end of a coding region, can also be separate from a promoter sequence and can be, e.g., within an intronic region of a gene or 3' to the coding region of the gene.

As used herein, "operably linked" means incorporated into a genetic construct (e.g., vector) so that expression control sequences effectively control expression of a coding sequence of interest.

Expression vectors can be introduced into host cells (e.g., by transformation or transfection) for expression of the encoded polypeptide, which then can be purified. Expression systems that can be used for small or large scale production of polypeptides (e.g., a mannosidase, alkaline protease, or GAA or fragment thereof) include, without limitation, microorganisms such as bacteria (e.g., *E. coli*) transformed with recombinant bacteriophage DNA, plasmid DNA, or cosmid DNA expression vectors containing the nucleic acid molecules, and fungal (e.g., *Yarrowia lipolytica, Arxula adeninivorans, Pichia pastoris, Hansenula polymorpha, Ogataea minuta, Pichia methanolica, Aspergillus niger, Trichoderma reesei,* and *Saccharomyces cerevisiae*) transformed with recombinant fungal expression vectors containing the nucleic acid molecules. Useful expression systems also include insect cell systems infected with recombinant virus expression vectors (e.g., baculovirus) containing the nucleic acid molecules, and plant cell systems infected with recombinant virus expression vectors (e.g., tobacco mosaic virus) or transformed with recombinant plasmid expression vectors (e.g., Ti plasmid) containing the nucleic acid molecules. Mannosidase or alkaline protease polypeptides also can be produced using mammalian expression systems, which include cells (e.g., immortalized cell lines such as COS cells, Chinese hamster ovary cells, HeLa cells, human embryonic kidney 293 cells, and 3T3 L1 cells) harboring recombinant expression constructs containing promoters derived from the genome of mammalian cells (e.g., the metallothionein promoter) or from mammalian viruses (e.g., the adenovirus late promoter and the cytomegalovirus promoter).

Recombinant polypeptides such as a mannosidase can be tagged with a heterologous amino acid sequence such FLAG, polyhistidine (e.g., hexahistidine), hemagluttanin (HA), glutathione-S-transferase (GST), or maltose-binding protein (MBP) to aid in purifying the protein. Other methods for purifying proteins include chromatographic techniques such as ion exchange, hydrophobic and reverse phase, size exclusion, affinity, hydrophobic charge-induction chromatography, and the like (see, e.g., Scopes, Protein Purification: Principles and Practice, third edition, Springer-Verlag, New York (1993); Burton and Harding, *J. Chromatogr.* A 814: 71-81 (1998)).

In Vivo Methods of Uncapping and Demannosylating Glycoproteins

Genetically engineered cells described herein can be used to produce molecular complexes having GAA activity. For example, genetically engineered cells can be used to produce molecule complexes having GAA activity and comprising at least two polypeptides, each polypeptide having at least 85% sequence identity to a segment of the amino acid sequence set forth in SEQ ID NO: 1, each segment being derived by proteolysis of the amino acid sequence set forth in SEQ ID NO: 1 at one or more sites between amino acid 50 and amino acid 74 (e.g., between amino acid 56 and amino acid 68 or between amino acid 60 and amino acid 65). For example, a fungal cell can be engineered to include a nucleic acid encoding the amino acid sequence set forth in SEQ ID NO:1 and a nucleic acid encoding an alkaline protease having at least 85% sequence identity to the amino acid sequence set forth in SEQ ID NO:8 such that each of the encoded polypeptides are secreted into the culture medium, where the alkaline protease can cleave the amino acid sequence set forth in SEQ ID NO:1. As described in Example 12, when the recombinant GAA was secreted into the culture medium with the alkaline protease, processing of the 110 kDa precursor to the 95 kDa form was complete, i.e., the 110 kDa precursor was not detected.

Genetically engineered cells described herein also can be used to produce uncapped and demannosylated molecular complexes. Such genetically engineered cells can include a nucleic acid encoding a polypeptide having the amino acid sequence set forth in SEQ ID NO:1, a nucleic acid encoding a mannosidase as described herein, and optionally a nucleic acid encoding an alkaline protease having at least 85% sequence identity to the amino acid sequence set forth in SEQ ID NO:8.

A cell based method of producing uncapped and demannosylated molecule complexes can include introducing into a fungal cell genetically engineered to include a nucleic acid encoding a mannosidase that is capable of hydrolyzing a mannose-1-phospho-6-mannose linkage or moiety to phospho-6-mannose, a nucleic acid encoding a polypeptide having the amino acid sequence set forth in SEQ ID NO: 1 and optionally a nucleic acid encoding an alkaline protease having at least 85% sequence identity to the amino acid sequence set forth in SEQ ID NO:8, wherein the cell produces the molecular complex described herein containing uncapped phosphorylated N-glycans. Such phosphorylated N-glycans can be demannosylated as described above. In some embodiments, the nucleic acids encoding the mannosidase and GAA contain a secretion sequence such that the mannosidase and GAA are co-secreted. In genetically engineered cells that include a nucleic acid encoding an alkaline protease, the molecular complexes can be processed to the 95 kDa form.

Another cell based method can include the steps of introducing into a fungal cell genetically engineered to include a nucleic acid encoding a mannosidase that is capable of (i) hydrolyzing a mannose-1-phospho-6-mannose linkage or moiety to phospho-6-mannose and (ii) hydrolyzing a terminal alpha-1,2 mannose, alpha-1,3 mannose and/or alpha-1,6 mannose linkage or moiety of a phosphate containing glycan, a nucleic acid encoding a polypeptide having the amino acid sequence set forth in SEQ ID NO: 1, and optionally a nucleic acid encoding an alkaline protease having at least 85% sequence identity to the amino acid sequence set forth in SEQ ID NO:8, wherein the cell produces uncapped and demannosylated molecular complexes. In some embodiments, the nucleic acids encoding the mannosidase and GAA contain a secretion sequence such that the mannosidase and target molecule are co-secreted. In genetically engineered cells that include a nucleic acid encoding an alkaline protease, the molecular complexes can be processed to the 95 kDa form.

Cells suitable for in vivo production of target molecules or molecular complexes can be of fungal origin, including *Yarrowia lipolytica, Arxula adeninivorans*, methylotrophic yeast (such as a methylotrophic yeast of the genus *Candida, Hansenula, Oogataea, Pichia* or *Torulopsis*) or filamentous fungi of the genus *Aspergillus, Trichoderma, Neurospora, Fusarium,* or *Chrysosporium*. Exemplary fungal species include, without limitation, *Pichia anomala, Pichia bovis, Pichia canadensis, Pichia carsonii, Pichia farinose, Pichia fermentans, Pichia fluxuum, Pichia membranaefaciens, Pichia membranaefaciens, Candida valida, Candida albicans, Candida ascalaphidarum, Candida amphixiae, Candida Antarctica, Candida atlantica, Candida atmosphaerica, Candida blattae, Candida carpophila, Candida cerambycidarum, Candida chauliodes, Candida corydalis, Candida dosseyi, Candida dubliniensis, Candida ergatensis, Candida fructus, Candida glabrata, Candida fermentati, Candida guilliermondii, Candida haemulonii, Candida insectamens, Candida insectorum, Candida intermedia, Candida jeffresii, Candida kefyr, Candida krusei, Candida lusitaniae, Candida lyxosophila, Candida maltosa, Candida membranifaciens, Candida milleri, Candida oleophila, Candida oregonensis, Candida parapsilosis, Candida quercitrusa, Candida shehatea, Candida temnochilae, Candida tenuis, Candida tropicalis, Candida tsuchiyae, Candida sinolaborantium, Candida sojae, Candida viswanathii, Candida utilis, Oogataea minuta, Pichia membranaefaciens, Pichia silvestris, Pichia membranaefaciens, Pichia chodati, Pichia membranaefaciens, Pichia menbranaefaciens, Pichia minuscule, Pichia pastoris, Pichia pseudopolymorpha, Pichia quercuum, Pichia robertsii, Pichia saitoi, Pichia silvestrisi, Pichia strasburgensis, Pichia terricola, Pichia vanriji, Pseudozyma Antarctica, Rhodosporidium toruloides, Rhodotorula glutinis, Saccharomyces bayanus, Saccharomyces bayanus, Saccharomyces momdshuricus, Saccharomyces uvarum, Saccharomyces bayanus, Saccharomyces cerevisiae, Saccharomyces bisporus, Saccharomyces chevalieri, Saccharomyces delbrueckii, Saccharomyces exiguous, Saccharomyces fermentati, Saccharomyces fragilis, Saccharomyces marxianus, Saccharomyces mellis, Saccharomyces rosei, Saccharomyces rouxii, Saccharomyces uvarum, Saccharomyces willianus, Saccharomycodes ludwigii, Saccharomycopsis capsularis, Saccharomycopsis fibuligera, Saccharomycopsis fibuligera, Endomyces hordei, Endomycopsis fobuligera. Saturnispora saitoi, Schizosaccharomyces octosporus, Schizosaccharomyces pombe, Schwanniomyces occidentalis, Torulaspora delbrueckii, Torulaspora delbrueckii, Saccharomyces dairensis, Torulaspora delbrueckii, Torulaspora fermentati, Saccharomyces fermentati, Torulaspora delbrueckii, Torulaspora rosei, Saccharomyces rosei, Torulaspora delbrueckii, Saccharomyces rosei, Torulaspora delbrueckii, Saccharomyces delbrueckii, Torulaspora delbrueckii, Saccharomyces delbrueckii, Zygosaccharomyces mongolicus, Dorulaspora globosa, Debaryomyces globosus, Torulopsis globosa, Trichosporon cutaneum, Trigonopsis variabilis, Williopsis californica, Williopsis saturnus, Zygosaccharomyces bisporus, Zygosaccharomyces bisporus, Debaryomyces disporua. Saccharomyces bisporas, Zygosaccharomyces bisporus, Saccharomyces bisporus, Zygosaccharomyces mellis, Zygosaccharomyces priorianus, Zygosaccharomyces rouxiim, Zygosaccharomyces rouxii, Zygosaccharomyces barkeri, Saccharomyces rouxii, Zygosaccharomyces rouxii, Zygosaccharomyces major, Saccharomyces rouxii, Pichia anomala, Pichia bovis, Pichia Canadensis, Pichia carsonii, Pichia farinose, Pichia fermentans, Pichia fluxuum, Pichia membranaefaciens, Pichia pseudopolymorpha, Pichia quercuum, Pichia robertsii, Pseudozyma Antarctica, Rhodosporidium toruloides, Rhodosporidium toruloides, Rhodotorula glutinis, Saccharomyces bayanus, Saccharomyces bayanus, Saccharomyces bisporus, Saccharomyces cerevisiae, Saccharomyces chevalieri, Saccharomyces delbrueckii, Saccharomyces fermentati, Saccharomyces fragilis, Saccharomycodes ludwigii, Schizosaccharomyces pombe, Schwanniomyces occidentalis, Torulaspora delbrueckii, Torulaspora globosa, Trigonopsis variabilis, Williopsis californica, Williopsis saturnus, Zygosaccharomyces bisporus, Zygosaccharomyces mellis*, or *Zygosaccharomyces rouxii*. Exemplary filamentous fungi include various species of *Aspergillus* including, but not limited to, *Aspergillus caesiellus, Aspergillus candidus, Aspergillus carneus, Aspergillus clavatus, Aspergillus deflectus, Aspergillus flavus, Aspergillus fumigatus, Aspergillus glaucus, Aspergillus nidulans, Aspergillus niger, Aspergillus ochraceus, Aspergillus oryzae, Aspergillus parasiticus, Aspergillus penicilloides, Aspergillus restrictus, Aspergillus sojae, Aspergillus sydowi, Aspergillus tamari, Aspergillus terreus, Aspergillus ustus*, or *Aspergillus versicolor*. Such cells, prior to the genetic engineering as specified herein, can be obtained from a variety of commercial sources and research resource facilities, such as, for example, the American Type Culture Collection (Rockville, Md.).

Genetic engineering of a cell can include, in addition to an exogenous nucleic acid encoding a mannosidase, GAA, and/or alkaline protease, one or more genetic modifications such as: (i) deletion of an endogenous gene encoding an Outer CHain elongation (OCH1) protein; (ii) introduction of a recombinant nucleic acid encoding a polypeptide capable of promoting mannosyl phosphorylation (e.g., a MNN4 polypeptide from *Yarrowia lipolytica, S. cerevisiae, Ogataea minuta, Pichia pastoris*, or *C. albicans*, or PNO1 polypeptide from *P. pastoris*) to increasing phosphorylation of mannose residues; (iii) introduction or expression of an RNA molecule that interferes with the functional expression of an OCH1 protein; (iv) introduction of a recombinant nucleic acid encoding a wild-type (e.g., endogenous or exogenous) protein having a N-glycosylation activity (i.e., expressing a protein having an N-glycosylation activity); or (v) altering the promoter or enhancer elements of one or more endogenous genes encoding proteins having N-glycosylation activity to thus alter the expression of their encoded proteins. RNA molecules include, e.g., small-interfering RNA (siRNA), short hairpin RNA (shRNA), anti-sense RNA, or micro RNA (miRNA). Genetic engineering also includes altering an endogenous gene encoding a protein having an N-glycosylation activity to produce a protein having additions (e.g., a heterologous sequence), deletions, or substitutions (e.g., mutations such as point mutations; conservative or non-conservative mutations). Mutations can be introduced specifically (e.g., by site-directed mutagenesis or homologous recombination) or can be introduced randomly (for example, cells can be chemically mutagenized as described in, e.g., Newman and Ferro-Novick (1987) *J. Cell Biol.* 105(4):1587.

Genetic modifications described herein can result in one or more of (i) an increase in one or more activities in the genetically modified cell, (ii) a decrease in one or more activities in the genetically modified cell, or (iii) a change in the localization or intracellular distribution of one or more activities in the genetically modified cell. It is understood that an increase in the amount of a particular activity (e.g., promoting mannosyl phosphorylation) can be due to over-expressing one or more proteins capable of promoting mannosyl phosphorylation, an increase in copy number of an endogenous gene (e.g., gene duplication), or an alteration in the promoter or enhancer of an endogenous gene that stimulates an increase in expression of the protein encoded by the gene. A decrease in one or more particular activities can be due to overexpression of a mutant form (e.g., a dominant negative form), introduction or expression of one or more interfering RNA molecules that reduce the expression of one or more proteins having a particular activity, or deletion of one or more endogenous genes that encode a protein having the particular activity.

To disrupt a gene by homologous recombination, a "gene replacement" vector can be constructed in such a way to include a selectable marker gene. The selectable marker gene can be operably linked, at both 5' and 3' end, to portions of the gene of sufficient length to mediate homologous recombination. The selectable marker can be one of any number of genes which either complement host cell auxotrophy or provide antibiotic resistance, including URA3, LEU2 and HIS3 genes. Other suitable selectable markers include the CAT gene, which confers chloramphenicol resistance to yeast cells, or the lacZ gene, which results in blue colonies due to the expression of β-galactosidase. Linearized DNA fragments of the gene replacement vector are then introduced into the cells using methods well known in the art (see below). Integration of the linear fragments into the genome and the disruption of the gene can be determined based on the selection marker and can be verified by, for example, Southern blot analysis. A selectable marker can be removed from the genome of the host cell by, e.g., Cre-loxP systems (see below).

Alternatively, a gene replacement vector can be constructed in such a way as to include a portion of the gene to be disrupted, which portion is devoid of any endogenous gene promoter sequence and encodes none or an inactive fragment of the coding sequence of the gene. An "inactive fragment" is a fragment of the gene that encodes a protein having, e.g., less than about 10% (e.g., less than about 9%, less than about 8%, less than about 7%, less than about 6%, less than about 5%, less than about 4%, less than about 3%, less than about 2%, less than about 1%, or 0%) of the activity of the protein produced from the full-length coding sequence of the gene. Such a portion of the gene is inserted in a vector in such a way that no known promoter sequence is operably linked to the gene sequence, but that a stop codon and a transcription termination sequence are operably linked to the portion of the gene sequence. This vector can be subsequently linearized in the portion of the gene sequence and transformed into a cell. By way of single homologous recombination, this linearized vector is then integrated in the endogenous counterpart of the gene.

Expression vectors can be autonomous or integrative. A recombinant nucleic acid (e.g., one encoding a mannosidase, GAA, or alkaline protease) can be in introduced into the cell in the form of an expression vector such as a plasmid, phage, transposon, cosmid or virus particle. The recombinant nucleic acid can be maintained extrachromosomally or it can be integrated into the yeast cell chromosomal DNA. Expression vectors can contain selection marker genes encoding proteins required for cell viability under selected conditions (e.g., URA3, which encodes an enzyme necessary for uracil biosynthesis or TRP1, which encodes an enzyme required for tryptophan biosynthesis) to permit detection and/or selection of those cells transformed with the desired nucleic acids (see, e.g., U.S. Pat. No. 4,704,362). Expression vectors can also include an autonomous replication sequence (ARS). For example, U.S. Pat. No. 4,837,148 describes autonomous replication sequences which provide a suitable means for maintaining plasmids in *Pichia pastoris*.

Integrative vectors are disclosed, e.g., in U.S. Pat. No. 4,882,279. Integrative vectors generally include a serially arranged sequence of at least a first insertable DNA fragment, a selectable marker gene, and a second insertable DNA fragment. The first and second insertable DNA fragments are each about 200 (e.g., about 250, about 300, about 350, about 400, about 450, about 500, or about 1000 or more) nucleotides in length and have nucleotide sequences which are homologous to portions of the genomic DNA of the species to be transformed. A nucleotide sequence containing a gene of interest (e.g., a gene encoding GAA) for expression is inserted in this vector between the first and second insertable DNA fragments whether before or after the marker gene. Integrative vectors can be linearized prior to yeast transformation to facilitate the integration of the nucleotide sequence of interest into the host cell genome.

An expression vector can feature a recombinant nucleic acid under the control of a yeast (e.g., *Yarrowia lipolytica, Arxula adeninivorans, P pastoris*, or other suitable fungal species) promoter, which enables them to be expressed in fungal cells. Suitable yeast promoters include, e.g., ADC1, TPI1, ADH2, hp4d, PDX, and Gal10 (see, e.g., Guarente et al. (1982) *Proc. Natl. Acad. Sci. USA* 79(23):7410) promoters. Additional suitable promoters are described in, e.g., Zhu and Zhang (1999) *Bioinformatics* 15(7-8):608-611 and U.S. Pat. No. 6,265,185.

A promoter can be constitutive or inducible (conditional). A constitutive promoter is understood to be a promoter whose expression is constant under the standard culturing conditions. Inducible promoters are promoters that are responsive to one or more induction cues. For example, an inducible promoter can be chemically regulated (e.g., a promoter whose transcriptional activity is regulated by the presence or absence of a chemical inducing agent such as an alcohol, tetracycline, a steroid, a metal, or other small molecule) or physically regulated (e.g., a promoter whose transcriptional activity is regulated by the presence or absence of a physical inducer such as light or high or low temperatures). An inducible promoter can also be indirectly regulated by one or more transcription factors that are themselves directly regulated by chemical or physical cues.

It is understood that other genetically engineered modifications can also be conditional. For example, a gene can be conditionally deleted using, e.g., a site-specific DNA recombinase such as the Cre-loxP system (see, e.g., Gossen et al. (2002) *Ann. Rev. Genetics* 36:153-173 and U.S. Application Publication No. 20060014264).

A recombinant nucleic acid can be introduced into a cell described herein using a variety of methods such as the spheroplast technique or the whole-cell lithium chloride yeast transformation method. Other methods useful for transformation of plasmids or linear nucleic acid vectors into cells are described in, for example, U.S. Pat. No. 4,929,555; Hinnen et al. (1978) *Proc. Nat. Acad. Sci. USA* 75:1929; Ito et al. (1983) *J. Bacteriol.* 153:163; U.S. Pat. No. 4,879,231; and Sreekrishna et al. (1987) *Gene* 59:115, the disclosures of each of which are incorporated herein by reference in their entirety. Electroporation and PEG1000 whole cell transformation procedures may also be used, as described by Cregg and Russel, Methods in Molecular Biology: *Pichia* Protocols, Chapter 3, Humana Press, Totowa, N.J., pp. 27-39 (1998).

Transformed fungal cells can be selected for by using appropriate techniques including, but not limited to, culturing auxotrophic cells after transformation in the absence of the biochemical product required (due to the cell's auxotrophy), selection for and detection of a new phenotype, or culturing in the presence of an antibiotic which is toxic to the yeast in the absence of a resistance gene contained in the transformants. Transformants can also be selected and/or verified by integration of the expression cassette into the genome, which can be assessed by, e.g., Southern blot or PCR analysis.

Prior to introducing the vectors into a target cell of interest, the vectors can be grown (e.g., amplified) in bacterial cells such as *Escherichia coli* (*E. coli*) as described above. The vector DNA can be isolated from bacterial cells by any of the methods known in the art which result in the purification of vector DNA from the bacterial milieu. The purified vector DNA can be extracted extensively with phenol, chloroform, and ether, to ensure that no *E. coli* proteins are present in the plasmid DNA preparation, since these proteins can be toxic to mammalian cells.

In some embodiments, the genetically engineered fungal cell lacks the OCH1 gene or gene products (e.g., mRNA or protein) thereof, and is deficient in OCH1 activity. In some embodiments, the genetically engineered cell expresses a polypeptide capable of promoting mannosyl phosphorylation (e.g., a MNN4 polypeptide from *Yarrowia lipolytica*, *S. cerevisiae*, *Ogataea minuta*, *Pichia pastoris*, or *C. albicans*, or a PNO1 polypeptide from *P. pastoris*). For example, the fungal cell can express a MNN4 polypeptide from *Y. lipolytica* (Genbank® Accession Nos: XM_503217, Genolevures Ref: YALI0D24101g). In some embodiments, the genetically engineered cell is deficient in OCH1 activity and expresses a polypeptide capable of promoting mannosyl phosphorylation.

Following uncapping and demannosylation, the molecular complex can be isolated. In some embodiments, the molecular complex is maintained within the yeast cell and released upon cell lysis. In some embodiments, the molecular complex is secreted into the culture medium via a mechanism provided by a coding sequence (either native to the exogenous nucleic acid or engineered into the expression vector), which directs secretion of the molecule from the cell. The presence of the uncapped and demannosylated molecular complex in the cell lysate or culture medium can be verified by a variety of standard protocols for detecting the presence of the molecule, e.g., immunoblotting or radioimmunoprecipitation with an antibody specific for GAA, or testing for a specific enzyme activity (e.g., glycogen degradation).

In some embodiments, following isolation, the uncapped and demannosylated target molecule or molecular complex can be attached to a heterologous moiety, e.g., using enzymatic or chemical means. A "heterologous moiety" refers to any constituent that is joined (e.g., covalently or non-covalently) to the altered target molecule, which constituent is different from a constituent originally present on the altered target molecule. Heterologous moieties include, e.g., polymers, carriers, adjuvants, immunotoxins, or detectable (e.g., fluorescent, luminescent, or radioactive) moieties. In some embodiments, an additional N-glycan can be added to the altered target molecule.

Methods for detecting glycosylation of molecules include DNA sequencer-assisted (DSA), fluorophore-assisted carbohydrate electrophoresis (FACE) or surface-enhanced laser desorption/ionization time-of-flight mass spectrometry (SELDI-TOF MS). For example, an analysis can utilize DSA-FACE in which, for example, glycoproteins are denatured followed by immobilization on, e.g., a membrane. The glycoproteins can then be reduced with a suitable reducing agent such as dithiothreitol (DTT) or β-mercaptoethanol. The sulfhydryl groups of the proteins can be carboxylated using an acid such as iodoacetic acid. Next, the N-glycans can be released from the protein using an enzyme such as N-glycosidase F. N-glycans, optionally, can be reconstituted and derivatized by reductive amination. For example, the released N-glycans can be labeled with a fluorophore such APTS (8-aminopyrene-1,3,6-trisulfonic acid), at the reducing terminus by reductive amination. The stoichiometry of labeling is such that only one APTS molecule is attached to each molecule of oligosaccharide. The derivatized N-glycans can then be concentrated. Instrumentation suitable for N-glycan analysis includes, e.g., the ABI PRISM® 377 DNA sequencer (Applied Biosystems). Data analysis can be performed using, e.g., GENESCAN® 3.1 software (Applied Biosystems). Isolated mannoproteins can be further treated with one or more enzymes such as calf intestine phosphatase to confirm their N-glycan status. Additional methods of N-glycan analysis include, e.g., mass spectrometry (e.g., MALDI-TOF-MS), high-pressure liquid chromatography (HPLC) on normal phase, reversed phase and ion exchange chromatography (e.g., with pulsed amperometric detection when glycans are not labeled and with UV absorbance or fluorescence if glycans are appropriately labeled). See also Callewaert et al. (2001) *Glycobiology* 11(4):275-281 and Freire et al. (2006) *Bioconjug. Chem.* 17(2):559-564.

Cultures of Engineered Cells

This document also provides a substantially pure culture of any of the genetically engineered cells described herein. As used herein, a "substantially pure culture" of a genetically engineered cell is a culture of that cell in which less than about 40% (i.e., less than about: 35%; 30%; 25%; 20%; 15%; 10%; 5%; 2%; 1%; 0.5%; 0.25%; 0.1%; 0.01%; 0.001%; 0.0001%; or even less) of the total number of viable cells in the culture are viable cells other than the genetically engineered cell, e.g., bacterial, fungal (including yeast), mycoplasmal, or protozoan cells. The term "about" in this context means that the relevant percentage can be 15% percent of the specified percentage above or below the specified percentage. Thus, for example, about 20% can be 17% to 23%. Such a culture of genetically engineered cells includes the cells and a growth, storage, or transport medium. Media can be liquid, semi-solid (e.g., gelatinous media), or frozen. The culture includes the cells growing in the liquid or in/on the semi-solid medium or being stored or transported in a storage or transport medium, including a frozen storage or transport medium. The cultures are in a culture vessel or storage vessel or substrate (e.g., a culture dish, flask, or tube or a storage vial or tube).

The genetically engineered cells described herein can be stored, for example, as frozen cell suspensions, e.g., in buffer containing a cryoprotectant such as glycerol or sucrose, as lyophilized cells. Alternatively, they can be stored, for example, as dried cell preparations obtained, e.g., by fluidized bed drying or spray drying, or any other suitable drying method.

Pharmaceutical Compositions and Methods of Treatment

GAA molecules and molecular complexes described herein, e.g., molecular complexes containing at least one modification that enhances transport to the interior of a mammalian cell, can be incorporated into a pharmaceutical composition containing a therapeutically effective amount of the molecule and one or more adjuvants, excipients, carriers, and/or diluents. Acceptable diluents, carriers and excipients typically do not adversely affect a recipient's homeostasis (e.g., electrolyte balance). Acceptable carriers include biocompatible, inert or bioabsorbable salts, buffering agents, oligo- or polysaccharides, polymers, viscosity-improving agents, preservatives and the like. One exemplary carrier is physiologic saline (0.15 M NaCl, pH 7.0 to 7.4). Another exemplary carrier is 50 mM sodium phosphate, 100 mM sodium chloride. Further details on techniques for formulation and administration of pharmaceutical compositions can be found in, e.g., Remington's Pharmaceutical Sciences (Maack Publishing Co., Easton, Pa.). Supplementary active compounds can also be incorporated into the compositions.

Administration of a pharmaceutical composition containing molecular complexes with one or modifications described herein can be systemic or local. Pharmaceutical compositions can be formulated such that they are suitable for parenteral and/or non-parenteral administration. Specific administration modalities include subcutaneous, intravenous, intramuscular, intraperitoneal, transdermal, intrathecal, oral, rectal, buccal, topical, nasal, ophthalmic, intra-articular, intra-arterial, sub-arachnoid, bronchial, lymphatic, vaginal, and intra-uterine administration.

Administration can be by periodic injections of a bolus of the pharmaceutical composition or can be uninterrupted or continuous by intravenous or intraperitoneal administration from a reservoir which is external (e.g., an IV bag) or internal (e.g., a bioerodable implant, a bioartificial organ, or a colony of implanted altered N-glycosylation molecule production cells). See, e.g., U.S. Pat. Nos. 4,407,957, 5,798,113, and 5,800,828. Administration of a pharmaceutical composition can be achieved using suitable delivery means such as: a pump (see, e.g., Annals of Pharmacotherapy, 27:912 (1993); Cancer, 41:1270 (1993); Cancer Research, 44:1698 (1984); microencapsulation (see, e.g., U.S. Pat. Nos. 4,352,883; 4,353,888; and 5,084,350); continuous release polymer implants (see, e.g., Sabel, U.S. Pat. No. 4,883,666); macroencapsulation (see, e.g., U.S. Pat. Nos. 5,284,761, 5,158,881, 4,976,859 and 4,968,733 and published PCT patent applications WO92/19195, WO 95/05452); injection, either subcutaneously, intravenously, intra-arterially, intramuscularly, or to other suitable site; or oral administration, in capsule, liquid, tablet, pill, or prolonged release formulation.

Examples of parenteral delivery systems include ethylene-vinyl acetate copolymer particles, osmotic pumps, implantable infusion systems, pump delivery, encapsulated cell delivery, liposomal delivery, needle-delivered injection, needle-less injection, nebulizer, aerosolizer, electroporation, and transdermal patch.

Formulations suitable for parenteral administration conveniently contain a sterile aqueous preparation of the altered N-glycosylation molecule, which preferably is isotonic with the blood of the recipient (e.g., physiological saline solution). Formulations can be presented in unit-dose or multi-dose form.

Formulations suitable for oral administration can be presented as discrete units such as capsules, cachets, tablets, or lozenges, each containing a predetermined amount of the altered N-glycosylation molecule; or a suspension in an aqueous liquor or a non-aqueous liquid, such as a syrup, an elixir, an emulsion, or a draught.

A molecular complex containing at least one modification that enhances transport of the complex to the interior of a mammalian cell that is suitable for topical administration can be administered to a mammal (e.g., a human patient) as, e.g., a cream, a spray, a foam, a gel, an ointment, a salve, or a dry rub. A dry rub can be rehydrated at the site of administration. Such molecules can also be infused directly into (e.g., soaked into and dried) a bandage, gauze, or patch, which can then be applied topically. Such molecules can also be maintained in a semi-liquid, gelled, or fully-liquid state in a bandage, gauze, or patch for topical administration (see, e.g., U.S. Pat. No. 4,307,717).

Therapeutically effective amounts of a pharmaceutical composition can be administered to a subject in need thereof in a dosage regimen ascertainable by one of skill in the art. For example, a composition can be administered to the subject, e.g., systemically at a dosage from 0.01 µg/kg to 10,000 µg/kg body weight of the subject, per dose. In another example, the dosage is from 1 µg/kg to 100 µg/kg body weight of the subject, per dose. In another example, the dosage is from 1 µg/kg to 30 µg/kg body weight of the subject, per dose, e.g., from 3 µg/kg to 10 µg/kg body weight of the subject, per dose.

In order to optimize therapeutic efficacy, a molecular complex described herein can be first administered at different dosing regimens. The unit dose and regimen depend on factors that include, e.g., the species of mammal, its immune status, the body weight of the mammal. Typically, levels of such a molecular complex in a tissue can be monitored using appropriate screening assays as part of a clinical testing procedure, e.g., to determine the efficacy of a given treatment regimen.

The frequency of dosing for a molecular complex described herein is within the skills and clinical judgement of medical practitioners (e.g., doctors or nurses). Typically, the administration regime is established by clinical trials which may establish optimal administration parameters. However, the practitioner may vary such administration regimes according to the subject's age, health, weight, sex and medical status. The frequency of dosing can be varied depending on whether the treatment is prophylactic or therapeutic.

Toxicity and therapeutic efficacy of such molecular complexes or pharmaceutical compositions thereof can be determined by known pharmaceutical procedures in, for example, cell cultures or experimental animals. These procedures can be used, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Pharmaceutical compositions that exhibit high therapeutic indices are preferred. While pharmaceutical compositions that exhibit toxic side effects can be used, care should be taken to design a delivery system that targets such compounds to the site of affected tissue in order to minimize potential damage to normal cells (e.g., non-target cells) and, thereby, reduce side effects.

The data obtained from the cell culture assays and animal studies can be used in formulating a range of dosage for use in appropriate subjects (e.g., human patients). The dosage of such pharmaceutical compositions lies generally within a range of circulating concentrations that include the $ED_{50}$ with little or no toxicity. The dosage may vary within this range depending upon the dosage form employed and the route of administration utilized. For a pharmaceutical composition used as described herein (e.g., for treating a metabolic disorder in a subject), the therapeutically effective dose can be estimated initially from cell culture assays. A dose can be formulated in animal models to achieve a circulating plasma concentration range that includes the $IC_{50}$ (i.e., the concentration of the pharmaceutical composition which achieves a half-maximal inhibition of symptoms) as determined in cell culture. Such information can be used to more accurately determine useful doses in humans. Levels in plasma can be measured, for example, by high performance liquid chromatography.

As defined herein, a "therapeutically effective amount" of a molecular complex is an amount of the complex that is capable of producing a medically desirable result (e.g., amelioration of one or more symptoms of Pompe's disease) in a treated subject. A therapeutically effective amount (i.e., an effective dosage) can includes milligram or microgram amounts of the complex per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram).

The subject can be any mammal, e.g., a human (e.g., a human patient) or a non-human primate (e.g., chimpanzee, baboon, or monkey), a mouse, a rat, a rabbit, a guinea pig, a gerbil, a hamster, a horse, a type of livestock (e.g., cow, pig, sheep, or goat), a dog, a cat, or a whale.

A molecular complex or pharmaceutical composition thereof described herein can be administered to a subject as a combination therapy with another treatment used for Pompe's disease. For example, the combination therapy can include administering to the subject (e.g., a human patient) one or more additional agents that provide a therapeutic benefit to the subject who has, or is at risk of developing (e.g., due to a mutation in the gene encoding GAA) Pompe's disease. Thus, the compound or pharmaceutical composition and the one or more additional agents can be administered at the same time. Alternatively, the molecular complex can be administered first and the one or more additional agents administered second, or vice versa.

Any of the molecular complexes described herein can be lyophilized.

Any of the pharmaceutical compositions described herein can be included in a container, pack, or dispenser together with instructions for administration. In some embodiments, the composition is packaged as a single use vial.

The following are examples of the practice of the invention. They are not to be construed as limiting the scope of the invention in any way.

EXAMPLES

Example 1

Uncapping and De-Mannosylation of Recombinant huGAA with CcMan5 and

Jack Bean α-Mannosidase

Recombinant human GAA (rhGAA) was produced as described in WO2011/039634 using *Y. lipolytica* production strain OXYY1589, which contains three copies of the human alpha glucosidase gene (also known as acid alpha glucosidase or acid maltase EC3.2.1.3) and two copies of the *Y. lipolytica* MNN4 gene. The amino acid sequence of human GAA is set forth in FIG. 1. The genotype of strain OXY1589 is as follows:

MatA, leu2-958, ura3-302, xpr2-322,
gut2-744, ade2-844
PDX2-Lip2pre-huGAA: URA3Ex::zeta
PDX2-Lip2pre-huGAA:LEU2Ex::zeta
PDX2-Lip2pre-hGM-CSF:GUTEx::zeta
YlMNN4-POX2-hp4d-YLMNN4:ADE2::PT targeted RhGAA was uncapped and demannosylated with *Cellulosimicrobium cellulans* mannosidase (CcMan5) and Jack bean α mannosidase (JbMan) (Sigma Product M7257, 3.0 M ammonium sulphate suspension). CcMan5 was produced recombinantly by first cloning the nucleic acid encoding the CcMan5 polypeptide (FIG. 2A) into vector pLSAH36, which contains a DsbA signal sequence and results in the expression of a protein with an N-terminal HIS tag. FIGS. 2B and 2C contain the amino acid sequence of the CcMan5 polypeptide with and without signal sequence, respectively. Plasmid pLSAH36 was cloned into *E. coli* B21 cells and proteins residing in the periplasm were isolated and purified using a Talon column. Before using the ammonium sulphate suspension of JbMan, it was further purified by gel filtration through a Superdex 200 column to remove contaminating phosphatase activities.

RhGAA (concentration of about 5 mg/mL in 20 mM sodium acetate (NaOAc) buffer, pH 5.0) was uncapped and demannosylated by incubating with CcMan5 (about 0.15-0.30 mg/mL in phosphate buffered saline (PBS)) and JbMan (about 0.5-1 mg/mL in PBS) in a w:w ratio of 100:5:10 for huGAA:CcMan5:JbMan. The total reaction volume was diluted with 500 mM NaOAc buffer, pH 5.0 and 100 mM $CaCl_2$ to obtain final concentrations of 100 mM NaOAc and 2 mM $CaCl_2$. The reaction mixture was incubated at 30° C. for 16 hours.

To evaluate the uncapping process and to analyze the N-glycan profile of the purified huGAA, the N-glycans of 5 μg glycoprotein were released with N-Glycosidase F (PNGaseF), labeled with APTS (8-amino-1,3,6-pyrenetrisulfonic acid; trisodium salt) and subsequently analyzed on DSA-FACE (DNA Sequencer-Aided Fluorophore-Assisted Carbohydrate Electrophoresis). The method essentially follows the protocol described in Laroy et al, *Nature Protocols*, 1:397-405 (2006).

The DSA-FACE electropherograms of the N-glycans from huGAA (76 kD form) before (panel B) and after (panel C) treatment with CcMan5 and JbMan are presented in FIG. 3A. Panel A is a reference sample containing the N-glycans released from RNaseB with PNGaseF. The N-glycan mixture released from capped huGAA is mainly composed of ManP-$Man_8GlcNAc_2$ and $(ManP)_2$-$Man_8GlcNAc_2$ (FIG. 3A, panel B). A peak running slightly faster than ManP-$Man_8GlcNAc_2$ can be assigned to ManP-$Man_7GlcNAc_2$. The main peaks observed after uncapping and demannosylation can be assigned to the double phosphorylated $P_2$-$Man_6GlcNAc_2$ and the monophosphorylated P-$Man_4GlcNAc_2$, P-$Man_5GlcNAc_2$ and P-$Man_6GlcNAc_2$ (PanelC).

Figure 3B:
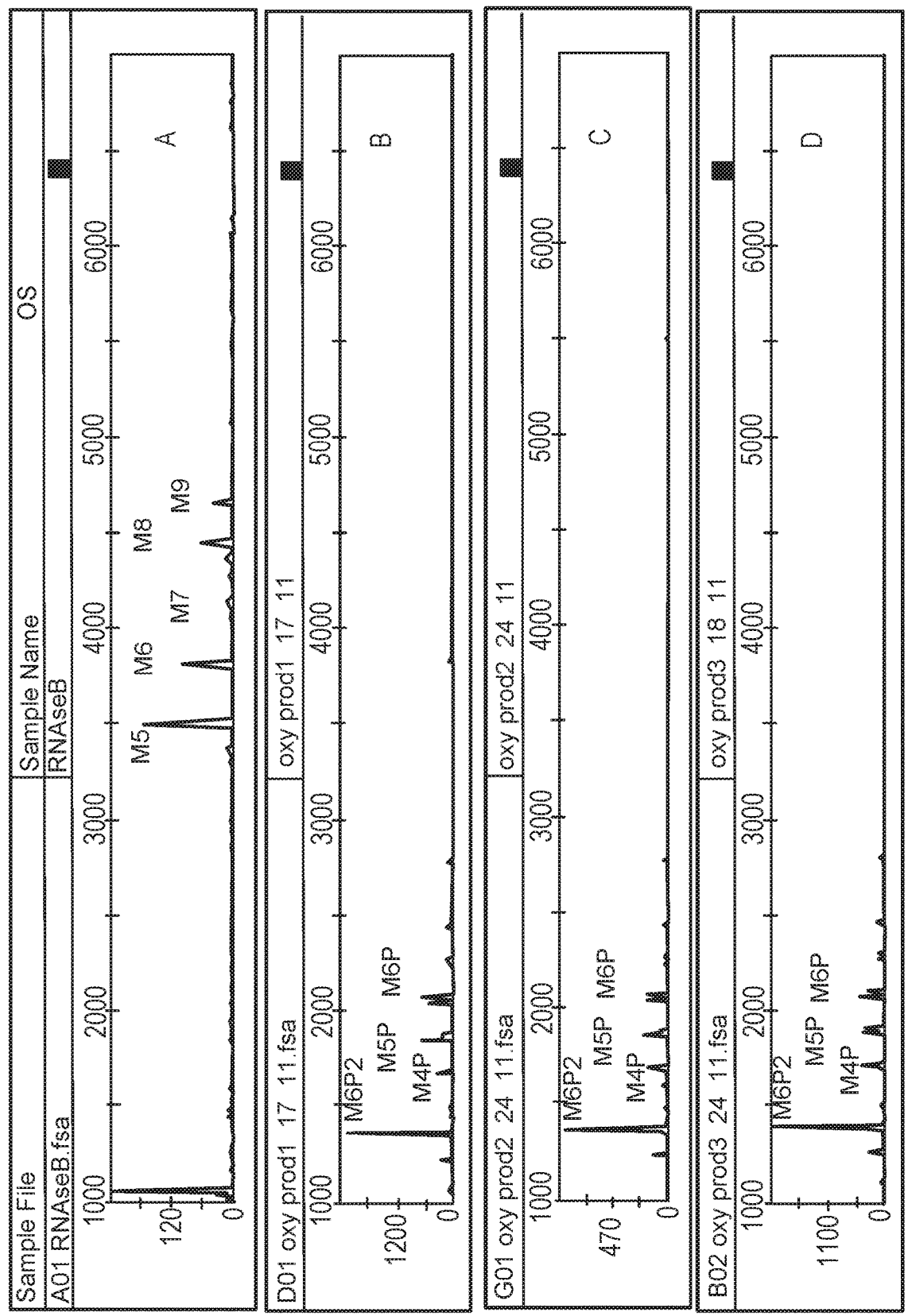

The uncapping of different processed forms of huGAA results in the same N-glycan profiles (FIG. 3B) for the 76 kD form (Panel B), 95 kD form (Panel C) and 110 kD form (Panel D).

Example 2

Purification of 110 kDa rhGAA

The 110 kDa form of rhGAA was isolated from strain OXYY1589 as follows. After harvest, the broth was centrifuged and filtered using a Durapore membrane (Merck Millipore). Ammonium sulphate (AMS) was added to a concentration of 1 M and the solute was filtered before loading on a hydrophobic interaction chromatography (HIC) column, equilibrated in 20 mM sodium phosphate pH 6, 1 M ammonium sulphate. The product was eluted with 20 mM sodium phosphate pH 6.

Before loading on a second chromatography column, the product was first concentrated via tangential flow filtration (TFF) on a regenerated cellulose membrane, then exchanged from buffer to 20 mM sodium acetate pH 4.5. This material was loaded on a cation exchange chromatography (CEX) column, equilibrated with 20 mM sodium acetate pH 4.5. After loading the column, it was washed with equilibration buffer until the UV absorbance signal reached baseline, and then washed with 20 mM sodium acetate pH 4.5, 50 mM NaCl. The product was eluted in 20 mM sodium acetate pH 4.5, 150 mM NaCl, and concentrated and exchanged from buffer to 20 mM sodium acetate pH 5. (See below)

The sample was uncapped and demannosylated as described in Example 1 then D-mannitol was added to a concentration of 100 mM. Three quarters of that material was reduced in volume via TFF using a regenerated cellulose membrane having a 10 kDa molecular weight cut off (MWCO) and purified further via size exclusion chromatography (SEC) on a Superdex 200 column equilibrated at 4° C. with 25 mM sodium phosphate pH 6, 150 mM NaCl, 100 mM D-mannitol. Fractions were screened afterwards for purity on cibacron-blue stained polyacrylamide gels under denaturating conditions. Pooled fractions were concentrated via TFF and ultracentrifuged using Amicon centrifugal filters of 10 kD MWCO (regenerated cellulose membrane, Merck Millipore).

Example 3

Purification of 110 kDa rhGAA

The 110 kDa form of rhGAA was isolated from strain OXYY1589 as follows. After harvest, the material was centrifuged and filtered before the concentration of AMS was increased to 1 M. The solute was again filtered and the product was captured on a HIC column, equilibrated with 20 mM sodium phosphate pH 6, 1 M AMS, and released in a step gradient from 1 to 0 M AMS in a 20 mM sodium phosphate pH 6 buffer.

The eluate was concentrated and buffer exchanged to 10 mM BIS-TRIS, pH 6 via TFF on a Vivaflow 200 module (PES membrane, 10 kD MWCO, Sartorius). The desalted material was brought onto an anion exchange chromatography (AEC) column. After washing of the column until the UV signal almost reached baseline, a two-phase continuous salt gradient was applied; the first gradient going from 0 to 0.3 M NaCl, the second from 0.3 to 1 M NaCl. Fractions were collected during the gradient and screened for GAA via a qualitative 4-methylumbellifferyl-a-D-glucopyranoside (4-MUG). In the 4-MUG assay, reactions were started by adding a reaction buffer consisting of 0.35 mM 4-MUG, 0.1% BSA and 100 mM sodium acetate pH 4 in a 10:1 volume proportion to 10 µl of elution fraction. After incubating for 30 minutes to 1 hour at 37° C., an equal volume of 100 mM glycine pH 11 was added to stop the reaction. The release of the fluorogenic reaction product 4-methylumbelliferone was observed under UV-light.

Fractions containing GAA were pooled and concentrated via TFF on a Vivaflow 200 module (PES membrane, 10 kD MWCO, Sartorius) and ultracentrifugation using Amicon centrifugal filters of 10 kD MWCO (regenerated cellulose membrane, Merck Millipore).

The concentrated material was split in two and purified further on a Superdex 200 column equilibrated at 4° C. with 50 mM sodium phosphate pH 6, 250 mM NaCl, 0.05% Tween-20. Fractions were screened afterwards for purity on cibacron-blue stained polyacrylamide gels under denaturing conditions, and phosphatase content was determined using a colormetric test using para-nitrophenylphosphate, which measures the enzymatic release of the yellow colored p-nitrophenolate reaction product at a wavelength of 405 nm.

Pilot pools were made from fractions containing GAA. The total protein of the pilot pools was determined via the Bradford assay. Selected fractions were pooled for concentration onto a Vivaflow 200 TFF module (PES membrane, 10 kD MWCO, Sartorius). The volume was further reduced using 15 ml Amicon centrifugal filters of 10 kD MWCO (regenerated cellulose membrane, Merck Millipore).

The concentrated material was subjected to a second round of size exclusion chromatography (SEC) using the same conditions as for the first SEC step. Fractions were again screened for purity on cibacron-blue stained polyacrylamide gels under denaturing conditions. Fractions were pooled according to the chosen pilot pool and concentrated on 15 ml Amicon centrifugal filters (10 kD MWCO, regenerated cellulose membrane, Merck Millipore).

Example 4

Purification of 95 kDa rhGAA

The 95 kDa form of rhGAA was isolated from strain OXYY1589 as follows. After harvest, the broth was centrifuged and filtered using a Durapore membrane (Merck Millipore). The product was afterwards concentrated via TFF on a modified polyethersulfone (PES) membrane with a molecular-weight-cut-off (MWCO) of 10 kD. AMS was added to a concentration of 1 M and the solute was filtered before loading on a HIC column, equilibrated in 20 mM sodium phosphate pH 6, 1 M AMS. The product was eluted with water, the pH of the eluate was adjusted by adding a stock buffer of 100 mM BIS-TRIS pH 6 to a concentration of 10 mM, and it was stored at 4° C. for 13 days.

Before loading on an AEX column, the product was concentrated via TFF on a regenerated cellulose membrane with an MWCO of 10 kD and buffer-exchanged to 10 mM BIS-TRIS pH 6. The desalted material was processed further via AEX chromatography, performed as described in Example 3. Fractions were collected during the gradient and screened for GAA via the qualitative 4-MUG assay. Fractions containing GAA were pooled for further purification.

For the third chromatography step, the concentration of AMS was increased to 1 M, and, after filtration, the material was further purified via HIC. A continuous salt gradient from 1 to 0 M AMS was applied while collecting fractions during the gradient. All fractions were screened for GAA via the qualitative assay and those containing GAA were pooled for further processing.

The pool was concentrated via ultra-centrifugation using 15 ml Amicon centrifugal filters of 10 kD MWCO regenerated cellulose membrane and further purified via SEC using the same procedures as described in Example 3. Fractions were screened afterwards for purity on cibacron-blue stained polyacrylamide gels under denaturing conditions. The 90% pure GAA fractions were pooled and first concentrated on a TFF Vivaflow 200 module (PES membrane, 10 kD MWCO, Sartorius), and then subjected to ultra-centrifugation using 15 ml Amicon centrifugal filters (10 kD MWCO, regenerated cellulose membrane, Merck Millipore). The concentrated material was subjected to a second round of SEC using the same conditions as for the first SEC step. Fractions were screened for GAA using the qualitative 4-MUG GAA assay. Fractions having GAA activity were pooled and concentrated.

After uncapping and demannosylation as set forth in Example 1, D-mannitol was added to a concentration of 100 mM and the volume was again reduced before loading onto a final Superdex 200 gel filtration column, equilibrated at 4° C. with 25 mM sodium phosphate pH 6, 150 mM NaCl, 100 mM D-mannitol. Fractions were screened for GAA using the 4-MUG qualitative assay, and those containing the product were pooled and concentrated.

Example 5

Purification of 95-110 kDa rhGAA Mix

Both the 110 kDa precursor and 95 kDa form of rhGAA was isolated from strain OXYY1589 as follows. After harvest, the material was processed to the second chromatography step as described in Example 2. After the HIC step, the product was concentrated and the buffer exchanged to 10 mM BIS-TRIS pH 6 via TFF, and loaded on an AEX column. The product was eluted in a single step from 0 to 300 mM NaCl at pH 6 (10 mM BIS-TRIS) and then concentrated using a Pellicon XL50 TFF module (regenerated cellulose membrane with a 10 kD MWCO). Half of the material was further purified via size exclusion chromatography. The chromatography step was performed as described in Example 3, but the selection of the fractions for further processing was only done on the basis of purity on cibacron-blue stained polyacrylamide gels under denaturing conditions.

Half of the pool was concentrated and combined with the remainder of the AEX-material. After uncapping and demannosylation, the concentration of D-mannitol was increased to 100 mM and the subsequent concentration and SEC steps were done following the same procedures as described in Example 2. Fractions were pooled on the basis of the 4-MUG qualitative assay and pooled with uncapped product from Example 6.

Example 6

Purification of 95 kDa rhGAA

The 95 kDa form of rhGAA was isolated from strain OXYY1589 as follows. After harvest, the material was processed up to and including the AEX step as described in Example 3. In the AEX step, a significant amount of the product resided in the flow through fraction due to an increase of conductivity during the loading. The flow through material was therefore again diafiltered to the appropriate buffer and subjected to a second round of AEX chromatography. Both amounts (batch A and batch B) were from here on processed separately.

Batch A was combined with the remainder of the SEC pool from Example 5 and the remainder of the CEX pool from Example 2 and the pool subsequently concentrated and diafiltered to a buffer containing 10 mM BIS-TRIS pH 6, 300 mM NaCl. The material was incubated at 30° C. for 65 h. The pH then was lowered to pH 5 by adding a 1 M stock buffer of sodium acetate pH 5 to a concentration of 125 mM, and the sample was again incubated at 30° C. After 24 h, the product was treated with Flavourzyme (Novozymes Corp), a protease mix from *Aspergillus oryzae*, using a 40:1 weight: weight ratio total protein content of the product versus protease mix, and was for the last time incubated at 30° C. After an overnight incubation, the material was purified via a first SEC step, performed under the same conditions as described in Example 3. Fractions were pooled that were estimated to contain pure product on the basis of cibacron-blue stained polyacrylamide gels under denaturing conditions. After concentration and buffer exchange to 20 mM sodium acetate pH 5, the material was uncapped and demannosylated as set forth in Example 1. D-mannitol was added to a concentration of 100 mM and the material was pooled with uncapped and demannosylated material from Example 5. The final SEC step and subsequent sample manipulations were performed as described in Example 2.

Batch B was pooled with end material from Example 3 and the pool was concentrated and diafiltered to a buffer containing 10 mM BIS-TRIS pH 6, 300 mM NaCl. The product was then treated with the *A. oryzae* protease mix for an overnight incubation period at 30° C. using the same weight ratios as described in Example 5, and, afterwards, purified via a first SEC step, performed under the same conditions as described in Example 3. Further processing of the product was done as described in Example 5.

In the final batch, product from batch A and batch B were mixed in 14:1 ratio in GAA content.

Example 7

Purification of 76 kDa rhGAA

The 76 kDa form of rhGAA was isolated from strain OXYY1589 as follows. After harvest, the culture was subjected to two rounds of continuous centrifugation. The supernatant was pooled and AMS was introduced to a concentration of approximately 1 M. After dissolution, 1 volume of HIC resin, pre-equilibrated in 20 mM sodium phosphate pH 6, 1 M AMS, was added to 50 volumes of supernatant while stirring to bind the product in a batch uptake mode. The resulting slurry was stored overnight at 4° C. without stirring. During this period, a brown colored layer settled at the top of the solute that was removed in the morning via gentle aspiration. The resin was washed three times with three volumes of lead buffer (20 mM sodium phosphate pH 6, 1 M AMS) in each round before it was packed into a column. The packed resin was washed until UV signal almost reached baseline and the product was afterwards eluted with water. The pH of the eluate was adjusted by adding a stock buffer of 100 mM BIS-TRIS pH 6 to a concentration of 10 mM. The material was then sterile filtered in a bag and stored for a period of eleven days at 4° C.

The second and third chromatography steps and accompanying manipulations of the material were performed as described in Example 4. The pool after the third chromatography step was first concentrated approximately seven times on two TFF Vivaflow 200 modules coupled in parallel (PES membrane, 10 kD MWCO, Sartorius), and then ultra-centrifuged using 15 ml Amicon centrifugal filters of 10 kD MWCO (regenerated cellulose membrane, Merck Millipore). The concentrated material was split in two and purified further via SEC using the same conditions as described for Example 4. Fractions were screened afterwards for purity on cibacron-blue stained polyacrylamide gels under denaturing conditions. Selected fractions were pooled for concentration onto two Vivaflow 200 TFF modules coupled in parallel (PES membrane, 10 kD MWCO, Sartorius). The volume was further reduced using 15 ml Amicon centrifugal filters of 10 kD MWCO (regenerated cellulose membrane, Merck Millipore).

After uncapping and demannosylation, D-mannitol was added to a concentration of 100 mM and the sample was again concentrated on a Vivaflow 50 TFF module (PES membrane, 10 kD MWCO, Sartorius) before loading onto a final SEC column, performed in the same way as described in Example 4. Product containing fractions were pooled and concentrated.

Example 8

Enzymatic Characterization of the Different Variants of huGAA (76, 95 and 110 kD Variants) Using the Artificial Chromogenic Substrate p-Nitrophenyl-α-D-Glucopyranoside The artificial chromogenic substrate p-nitrophenyl-α-D-glucopyranoside (PNPG) was used to determine the kinetic parameters of the unprocessed huGAA (110 kDa) obtained in Example 2 and the processed huGAA variants obtained in Example 7 (76 kDa), Example 6 (95 kDa) and Example 4 (95 kDa) A comparison also was made with the commercial human α-glucosidase, Myozyme® (alglucosidase alpha, Genzyme).

The enzymes were diluted to 20 µg/ml in 100 mM sodium acetate buffer pH 4.0, containing 0.1% BSA and 100 mM AMS (reaction buffer). Ten µl of the enzyme solutions were added to a 96-well plate in triplicate. The PNPG substrate (Sigma) was diluted to various substrate concentrations (10, 6, 4, 2, 1.6, 1.2, 0.8, and 0.4 mM) in reaction buffer and 90 µl of the diluted substrate was added to each well. The enzymatic reaction was incubated for 60 min at 37° C. followed by the addition of 100 µl 10% sodium carbonate, pH 12 to quench the reaction. The absorbance was measured at 405 nm. A standard curve with p-nitrophenol (PNP) was measured to calculate the amount of product formed per minute. The velocity expressed as µM/min was plotted in function of the different substrate concentrations generating a Michaelis-Menten curve. GraphPad Prism was used to calculate the Vmax and Km according to a direct fit to the Michaelis-Menten equation. The catalytic constant kcat and the catalytic efficiency kcat/Km were calculated. The specific activity of the various enzymes was reported as U/mg where 1 unit is defined as the amount of enzyme that catalyzes the hydrolysis of 1 nmol substrate per minute at 2 mM substrate concentration in 100 mM sodium acetate buffer, pH 4.0+0.1% BSA and 100 mM AMS. The results are shown in Table 1.

TABLE 1

|  | Myozyme | 95 kDa (Ex. 4) | 76 kDa (Ex. 7) | 110 kDa (Ex. 2) | 95 kDa (Ex. 6) |
| --- | --- | --- | --- | --- | --- |
| Vmax (µM/min) | 12 | 12 | 14 | 13 | 13 |
| Km (mM) | 4.4 | 4.4 | 4.3 | 4.4 | 4.7 |
| kcat (min$^{-1}$) | 660 | 677 | 770 | 688 | 730 |
| kcat/Km (min$^{-1}$mM$^{-1}$) | 150 | 154 | 179 | 156 | 155 |
| Sp. Activity (U/mg) | 2000 | 1910 | 2415 | 1935 | 1980 |

The unprocessed and processed forms of huGAA and Myozyme have comparable kinetic parameters towards the substrate PNPG. This is in accordance with data reported in literature for human acid α-glucosidase from Mouse milk and Chinese hamster ovary (CHO) medium (Bijvoet et at (1998), *Human Molecular Genetics,* 7, 1815-1824). The unprocessed (110 kD) and the processed (76 kD) form were reported to have the same Km and kcat value for the artificial substrate 4-methylumbelliferyl-α-D-glucopyranoside.

Example 9

Enzymatic Characterization of the Different Variants of huGAA (76, 95 and 110 kD Variants) Using Rabbit Liver Glycogen as the Substrate The enzymatic parameters of the unprocessed huGAA (110 kD variant; Example 2) and the processed huGAA variants (76 kDa, Example 7; and 95 kD, Example 6) were tested using rabbit liver glycogen (lot No 099K37931 V, Sigma). A comparison was made with the commercial human α-glucosidase, Myozyme® (alglucosidase alpha, Genzyme). The enzymes were diluted to 500 ng/ml in 100 mM sodium acetate buffer pH 4.0. 50 µl of the enzyme solutions were added to a 96-well plate in duplicate. The glycogen substrate was diluted to various substrate concentrations (250, 200, 150, 100, 75, 50, 25 mg/ml) in acetate buffer and 100 µl of the diluted substrate was added to each well. The enzymatic reaction was incubated for 60 min at 37° C. The amount of glucose was measured using the glucose-oxidase method with the amplex red substrate.

A glucose standard curve was measured to calculate the amount of product formed per minute. The enzyme velocity expressed as µM/min was plotted in function of the different substrate concentrations generating a Michaelis-Menten curve. GraphPad Prism was used to calculate the Vmax, and Km according to a direct fit to the Michaelis-Menten equation. The catalytic constant kcat and the catalytic efficiency kcat/Km were calculated. The specific activity of the various enzymes was reported as U/mg where 1 unit is defined as the amount of enzyme that catalyses the formation of 1 µmol glucose per minute at 50 mg/ml final substrate concentration in 100 mM sodium acetate buffer, pH 4.0. The results are shown in Table 2.

TABLE 2

|  | Myozyme | 76 kDa (Ex. 7) | 95 kDa (Ex. 6) | 110 kDa (Ex. 2) |
| --- | --- | --- | --- | --- |
| Vmax (µM/min) | 32 ± 6 | 15 ± 2 | 13 ± 1 | 11 ± 1 |
| Km (mM) | 600 ± 140 | 100 ± 10 | 93 ± 8 | 162 ± 17 |
| kcat (min$^{-1}$) | 21100 | 10000 | 8600 | 7260 |
| kcat/Km (min$^{-1}$mM$^{-1}$) | 35 | 100 | 92 | 45 |
| Sp. Activity (U/mg) | 14 | 32 | 27 | 16 |

Figure 4:
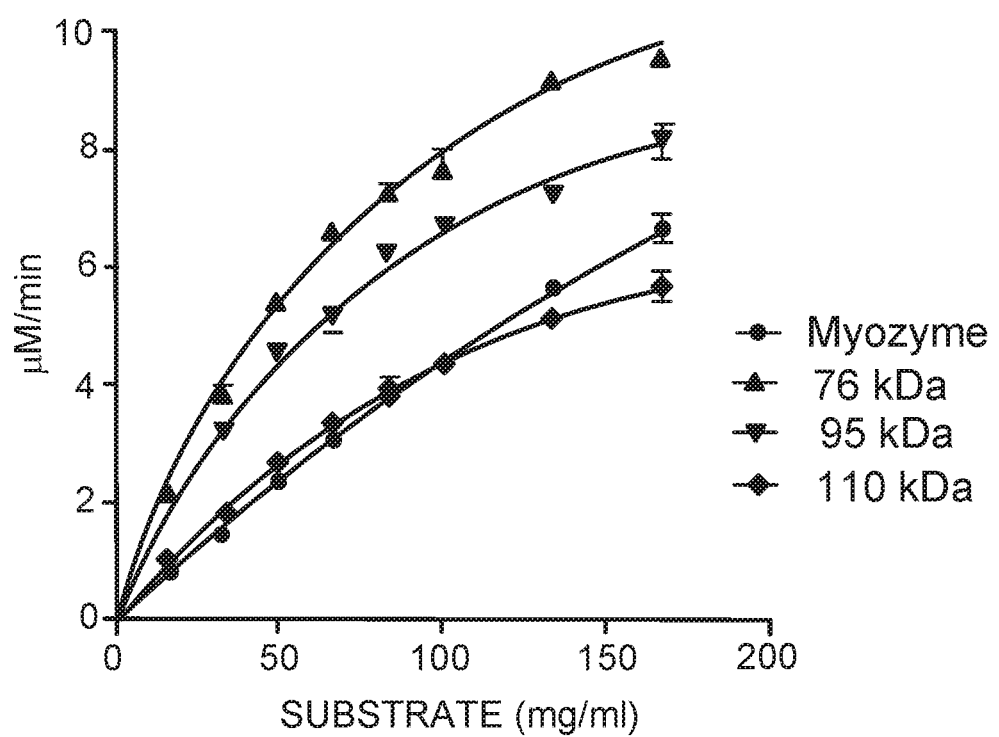
FIG. 4 is a line graph of the amount of glucose formed per minute with Myozyme (•), 76 kDa GAA (▲), 95 kDa GAA (▼), and 110 kDa GAA (♦) using rabbit liver glycogen as substrate.

In this experiment substrate saturation cannot be reached due to the limited solubility of rabbit glycogen (FIG. 4). For Myozyme, only an apparent Km and kcat value were calculated. For the three huGAA variants, lower apparent Km values were determined. The catalytic efficiency of the processed forms is two fold higher than the catalytic efficiency of unprocessed huGAA and Myozyme.

Example 10

Effect of Acid Alpha Glucosidase on Glycogen Clearance in a Mouse Model of Pompe Disease The GAA products from Example 7 (76 kDa, uncapped and demannosylated), Example 6 (95 kDa, uncapped and demannosylated), and Example 2 (110 kDa, uncapped and demannosylated) were administered to a mouse model of Pompe's disease to determine the glycogen clearance from skeletal muscle and heart.

The experiment was performed with FVB GAA knockout mice and FVB wild type mice. This animal model was chosen as a test system since it is a good representative for the early-onset infantile form of the disease. From birth onwards, the KO mice have a generalized and progressive accumulation of lysosomal glycogen (Bijvoet et al., 1998, supra). Male and female FVB GAA KO mice were obtained from the Erasmus University, Rotterdam. At the start of the treatment, mice were between 26-49 weeks of age.

The test substances or vehicle were administered intravenously by slow bolus in the tail veil with a dose volume of 10 ml/kg body weight (bw) once weekly for four weeks. Mice were fasted 16 hours prior to necropsy. Animals were sacrificed four days after the last injection. Details of the study groups are shown in Table 3.

TABLE 3

| Group/color code | Dose level (mg/kg bw) | Dose volume (ml/kg bw) | Type of mice | No of mice |
|---|---|---|---|---|
| 1/White | 0 | 10 | WT | 9 |
| 2/Blue | 0 | 10 | KO | 16 |
| 3/Green | 20 mg/kg 76 kDa | 10 | KO | 16 |
| 4/Red | 20 mg/kg 95 kDa | 10 | KO | 16 |
| 5/Yellow | 20 mg/kg 110 kDa | 10 | KO | 16 |
| 6/Orange | 20 mg/kg Myozyme | 10 | KO | 16 |

Perfusion and Homogenization of Organs

Heart and skeletal muscles (quadriceps femuralis, both sides) were isolated after perfusion with PBS. Tissue was homogenized in 10 weight volumes of ice cold PBS by using an ultra-turrax. Thereafter, the homogenate was sonicated at 16 micron on ice twice for 15 min. After centrifugation for 30 min at 12000 g, supernatant was collected for the measurement of glycogen.

Bioanalysis

The glycogen content in heart and skeletal muscle of each individual mouse was measured using a validated quantitative enzymatic assay. After boiling the tissues, a mixture of amyloglucosidase and α-amylase was added in vitro for the degradation of glycogen towards glucose. The amount of glucose was measured using the glucose-oxidase method with the amplex red substrate. The amount of glycogen is reported as μg glycogen/mg protein.

Statistical Analysis

Glycogen content in heart from groups 2, 3, 4, 5 were analyzed by ANOVA followed by post hoc comparison to group 6 (Myozyme) and to group 2 (placebo) by Dunnet's ttest. Group 1 was left out of the statistical analysis and was used as a quality check for lack of glycogen storage in the WT mouse model.

Because of the presence of outlying observations in the quadriceps data, a Kruskal-Wallis test was used to evaluate potential differential distribution of the glycogen content data of the different products.

Post hoc analysis of the quadriceps data was performed with the Wilcoxon rank sum test. Each product group and the Myozyme group was compared with the placebo (group 2) group, and each product group was compared with Myozyme.

Results

Table 4 shows the average glycogen levels (μg/mg protein) in heart (A) and skeletal muscle (B) of 16 mice per group.

TABLE 4

| Summary | Mean | sd |
|---|---|---|
| A. Average glycogen levels in heart | | |
| WT | 0.58 | 0.95 |
| KO/Placebo | 525.47 | 67.75 |
| KO/76 kDa | 377.75 | 80.20 |
| KO/95 kDa | 380.56 | 78.30 |
| KO/110 kDa | 416.56 | 106.77 |
| KO/Myozyme | 475.83 | 98.16 |
| B. Average glycogen levels in skeletal muscle | | |
| WT | 2.22 | 0.66 |
| KO/Placebo | 191.80 | 34.75 |
| KO/76 kDa | 152.27 | 35.35 |
| KO/95 kDa | 169.27 | 46.68 |
| KO/110 kDa | 160.39 | 36.46 |
| KO/Myozyme | 186.49 | 40.61 |

Figure 5A:
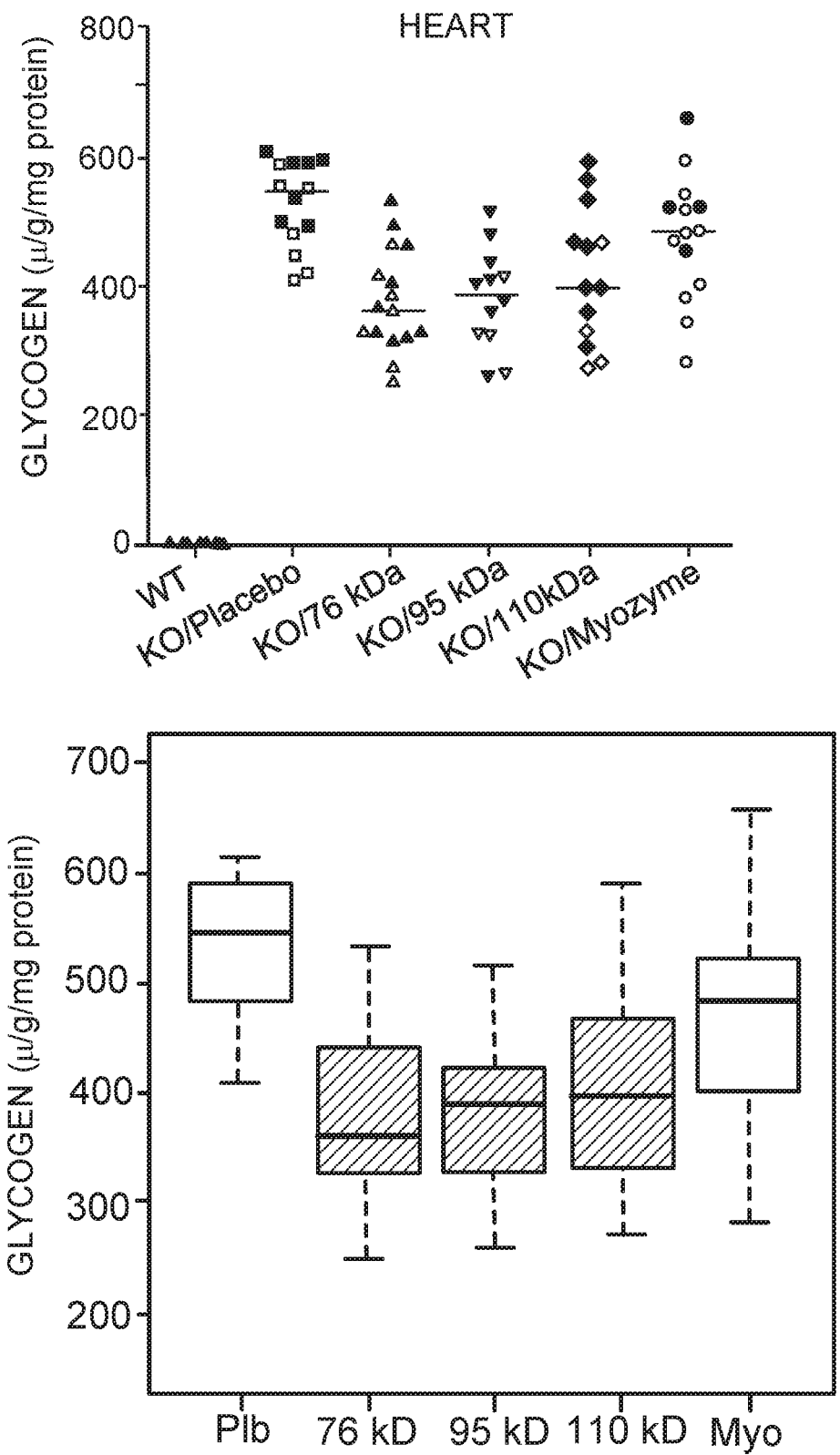
FIG. 5A contains two depictions of the glycogen levels (μg/mg protein) of individual mice in heart.
Figure 5B:
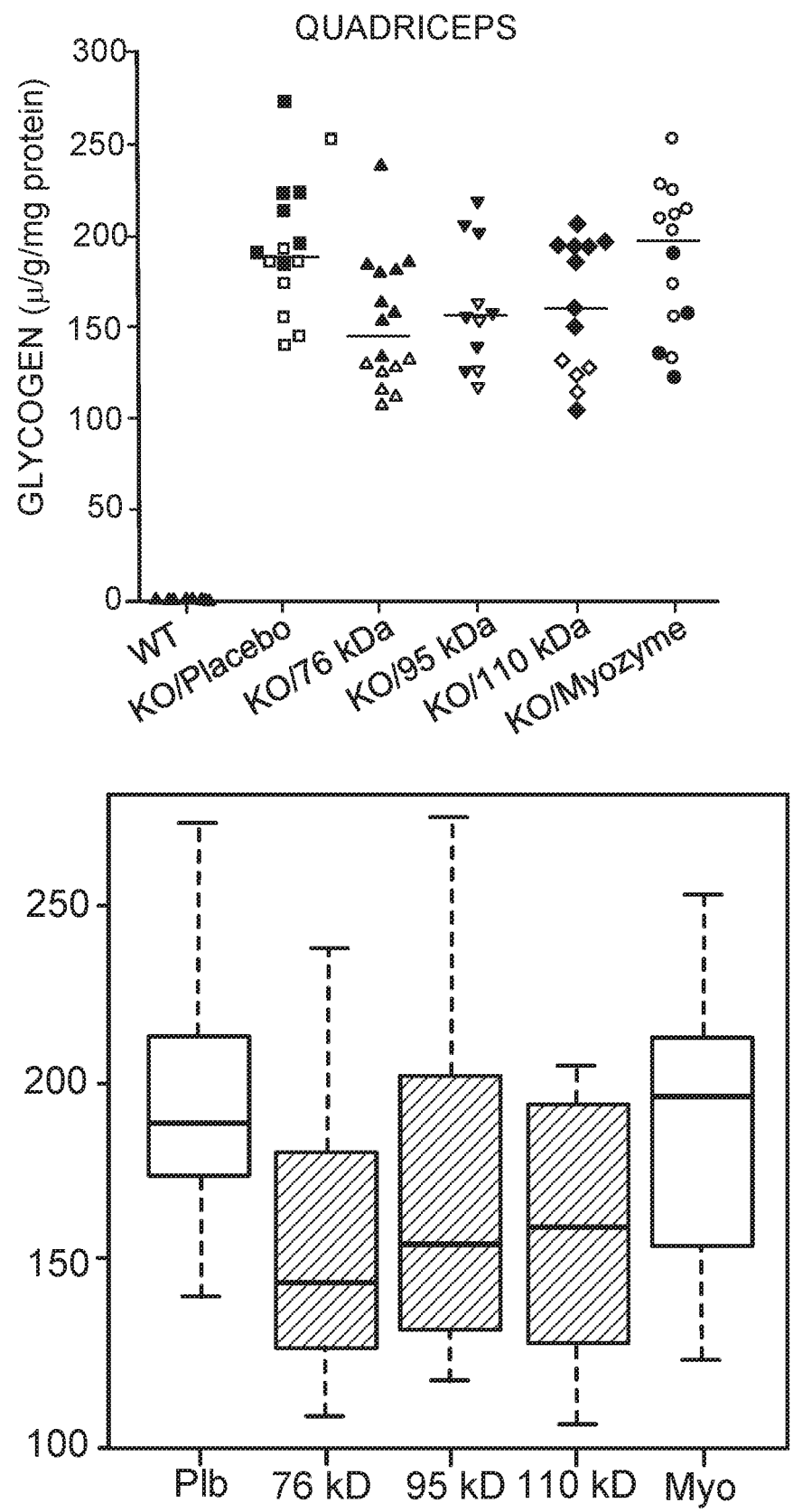
FIG. 5B contains two depictions of the glycogen levels (μg/mg protein) of individual mice in skeletal muscle. Red dots are females, black dots are males. Line represents the median of each group.

FIG. 5 shows the glycogen levels (μg/mg protein) of individual mice in heart (5A) and skeletal muscle (5B). The results show that the GAA products produced herein (110 kDa, 95 kDa, and 76 kDa) statistically reduce glycogen levels in heart compared to placebo-treated mice after four intravenous injections at 20 mg/kg. The same Myozyme® dose did not reduce the amount of glycogen in the heart. The glycogen levels in both the 76 kDa product and the 95 kDa treated groups were statistically different compared to the Myozyme®-treated group. Statistically, there was no difference between the three different GAA products produced herein.

The 76 kDa product produced herein also statistically reduced the amount of glycogen in skeletal muscle compared to placebo-treated or Myozyme®-treated mice. The glycogen levels in both the 95 kDa and the 110 kDa product were not statistically different compared to placebo and Myozyme®-treated mice, likely due to a higher variation between the individual mice. Myozyme® at 20 mg/kg was not capable of reducing the glycogen levels in skeletal muscle compared to placebo.

Example 11

Identification of a Protease from *Aspergillus oryzae*

GAA undergoes specific proteolytic cleavage upon incubation with low quantities of Flavourzyme (Novozymes Corp), a protease mix from *Aspergillus oryzae*, at acidic pH. The resulting GAA product has a molecular weight of approximately 95 kD on SDS-PAGE under reducing conditions. A similar proteolytic activity was observed in certain partially purified GAA preparations containing background proteins from the production strain (*Yarrowia lipolytica*).

To evaluate the proteolytic event, the N-glycans of GAA were removed to a single N-acetyl glucosamine per N-glycosylation site using EndoH, prior to proteolytic treatment. This allows more adequate evaluation via SDS PAGE. The GAA product was then incubated with the Flavourzyme protease cocktail or purified samples thereof. The reaction was performed at 30° C. in a 100 mM sodium acetate buffer pH 5. Samples were taken at different time points and analyzed via SDS-PAGE under reducing conditions. Volumes containing 0.5 µg of GAA were loaded per lane.

To investigate which protease family is responsible for the specific proteolysis of GAA in the protease cocktail, protease inhibitors were included in the assays that are specific to defined protease families to facilitate the identification of the protease. The reactions were performed as described above, with the exception that protease inhibitors were now added to the reaction mixture. The irreversible inhibitors PMSF (Sigma-Aldrich prod. nr. E5134-500G) and E-64 (Calbiochem prod. nr. CALB324890-5) were, prior to the proteolysis reaction, incubated with the diluted protease cocktail at a concentration of 1 mM and 10 µM respectively. The reversible inhibitors chymostatin (Calbiochem prod. nr. CALB230790-5), EDTA, and leupeptin (Calbiochem prod. nr. CALB108976-10MG) were directly added to the reaction mixture at a concentration of 60 µg/ml, 50 mM and 100 µM, respectively.

The specific proteolysis of GAA was inhibited by PMSF and chymostatin, protease inhibitors that abolish the activity of serine and cysteine proteases. The irreversible inhibitor E-64, which inhibits cysteine proteases, did not block the proteolysis. These data suggest that the specific proteolysis is a serine protease family member. More evidence supporting this hypothesis was provided by additional assays where the protease cocktail was incubated with PMSF and the redox agent dithiotheitol (DTT), which reduces disulfide bonds. Addition of this reducer reduces the covalent inactive cysteine protease:PMSF adduct, restoring the cysteine protease activity. When inhibited by PMSF, the activity of serine proteases can not be recovered by DTT. This difference in behavior was used to further discriminate between serine and cysteine proteases acting on GAA.

Incubation of the PMSF-inhibited protease with DTT did not restore the GAA-specific proteolysis activity of the protease cocktail. The GAA-specific proteolysis also was not inhibited by the metallo-protease inhibitor EDTA and a broad spectrum inhibitor leupeptin. All data indicate that a serine protease is responsible for this GAA proteolytic event.

In order to identify the protease from the mixture, the protease was purified using a series of chromatography steps. The first chromatography step used an anion exchange chromatography resin (Q-Sepharose FF, GE healthcare). The protease cocktail material was diluted in a 20 mM TRIS-HCl buffer pH 7 prior to loading. The flow through and the elutions at 100 mM, 300 mM and 500 mM NaCl in a 20 mM TRIS-HCl buffer were collected. All flow-through and elution fractions were analyzed using the assay as described above. The protease acting on GAA was present in the flow-through fraction of the run and was significantly enriched compared to the starting material.

The flow-through material was further processed via cation exchange chromatography (SP sepharose XL (GE Heathcare) at pH5 10 mM Na Acetate; elution with 0-300 mM NaCl). Elution fractions were collected and analyzed via instant blue stained SDS PAGE, and assayed for the presence of the protease of interest using the assay as described above.

The majority of the activity was present in the last fractions of the CEX chromatography eluate. The last two fractions were pooled and analyzed via mass spectrometry as follows. The protein mixture was desalted, reduced and alkylated prior to trypsin digestion and subsequently subjected to an LC-MS/MS methodology. Acquired spectra were matched onto the NCBI database using the Mascot algorithm. The following settings were applied:

Trypsin, Chymotrypsin (up to 4 miscleavages allowed)
Oxidation (M,W), deamidation (N,Q) (variable modifications)
Carbamidomethylation (fixed modification)
Taxonomy: Eukaryotes
MS tolerance: 0.05 Da, MS/MS tolerance: 0.05 Da An alkaline protease from *Aspergillus* (GenBank Accession No. BAA00258.1; gi 217809) was identified from the search. The sequence of the mature protease is:

```
>gi|217809|dbj|BAA00258.1| alkaline protease
[Aspergillus oryzae]
                                         (SEQ ID NO: 8)
GLTTQKSAPWGLGSISHKGQQSTDYIYDTSAGEGTYAYVVDSGVNVDHEE

FEGRASKAYNAAGGQHVDSIGHGTHVSGTIAGKTYGIAKKASILSVKVFQ

GESSSTSVILDGFNWAANDIVSKKRTSKAAINMSLGGGYSKAFNDAVENA

FEQGVLSVVAAGNENSDAGQTSPASAPDAITVAAIQKSNNRASFSNFGKV

VDVFAPGQDILSAWIGSSSATNTISGTSMATPHIVGLSLYLAALENLDGP

AAVTKRIKELATKDVVKDVKGSPNLLAYNGNA.
```

SDS-PAGE gel analysis of the purified protease from *A. oryzae* shows the presence of a band at a MW around 30 kDa (mature protease) and several bands with a MW between 20 and 10 kDa. The low MW bands were excised from the gel, trypsin digested, and analyzed by nano-LC-MS/MS. These bands were identified as products from the *A. oryzae* alkaline protease, indicating the alkaline protease from *A. oryzae* is susceptible to autoproteolysis.

Example 12

Expression of the *Aspergillus oryzae* Protease in *Yarrowia lipolytica*

The present example describes the construction of *Y. lipolytica* expressing the mature protein ALP. The gene encoding the alkaline protease (ALP) from *Aspergillus oryzae* (EC. 3.4.21.63) was codon optimized for *Y. lipolytica* expression and chemically synthesized as a fusion construct. The fusion construct encoded the entire open reading frame (ORF) of the enzyme including signal peptide (21 amino acids), pro-peptide (100 amino acids) and mature protein (282 amino acids) followed by a linker (SGGG) and a His Tag (10× His residue). See FIG. 9. The complete nucleotide sequence of the fusion construct is shown in FIG. 10.

The synthetic ORF of ALP was cloned into the pPT vector series, as BamHI/AvrII fragments, for targeted integration into the *Y. lipolytica* genome, utilizing different loci for stable integration of the expression cassette. In the pPT vectors, the bacterial moiety is derived from the plasmid pHSS6, and comprises a bacterial origin of replication (ori) and the kanamycin-resistant gene conferring resistance to kanamycin (KanR). The integration cassette comprises a) a selectable marker for transformation to *Y. lipolytica* (URA3; LEU2; ADE2), b) the expression cassette composed of a promoter (PDX2; Hp4d) c) a multiple cloning site (MCS) to insert the ALP synthetic construct and d) the terminator of the YlLIP2 gene. The integration cassette is flanked by upstream (P) and downstream (T) sequences of a specific locus for stable single copy targeted integration into *Y. lipolytica* genome by homologous recombination. Two NotI restriction sites enable the isolation of the expression cassette before transformation to avoid integration of the bacterial moiety.

The media and techniques used for *Y. lipolytica* is described by Barth and Gaillardin (*FEMS Microbiol Rev.*, 19(4):219-37, 1997), yeast cells were transformed by the lithium acetate method described by Le Dall et al. (*Curr Genet.*, 26(1):38-44, 1994), using 1 µg of purified integration cassette and standard techniques used for *E. coli*.

The integration of the expression cassette ALP was performed at one free locus and at 2 specific loci based on the fact that the insertion provides elimination of the expression of highly secreted proteins (lipase 2 and lipase 8) unwanted during the fermentation process. The final strain OXYY2184 contains 3 expression cassettes of ALP driven by the semi-constitutive Hp4D promoter.

OXYY2184 produces the recombinant *Aspergillus oryzae* ALP mature form (35 kDa), yielding about 2 to 2.5 g/L fermentation broth on average. Total protein was assayed using the Bradford technique and the protease activity was measured using an assay with azocasein as substrate. Proteases digest the azocasein towards casein and the free azo dye. Precipitation and centrifugation of the digested proteins allow the free azo dye to be measured at alkaline conditions, which is an indication of the proteolytic activity. The absorbance of this product is measured at OD 440 nm. The amount of digested azocasein can be calculated by correlation with an azocasein dilution series with known concentrations of which the absorbance is measured at OD 440 nm.

ALP in the culture supernatant of strain OXYY2184 was assayed by SDS-PAGE and immunodetected with an anti-His polyclonal antibody. The recombinant ALP produced in *Y. lipolytica* was active and had similar properties as the purified native enzyme. These enzyme properties of the recombinant ALP permit its use to process the rhuGAA precursor to obtain the 95 kDa rhuGAA form.

Strain OXYY2122 was constructed to co-express the ALP and rhuGAA. One copy of the ALP expression cassette was integrated into a recipient strain expressing the rhuGAA (4 copies of rhuGAA). Both genes encoding huGAA and ALP are driven under the inducible PDX2 promoter. The resulting strain OXYY2122 produces the mature form of ALP together with the rhuGAA precursor (110 Kda). Recombinant huGAA in the culture supernatant of strain OXYY2122 was assayed by SDS-PAGE followed by immunoblotting, and confirmed that the rhGAA was processed to the 95 kDa form in the supernatant. This processing was complete; no 110 kDa form was detected, whereas in the same cultivation of the strain without ALP no processing occurred.

Example 13

Purification of 95 kDa rhGAA Obtained after Treatment of rhGAA Fermentation Broth with the *Aspergillus oryzae* Alkaline Protease Expressed in *Yarrowia lipolytica*

The 95 kDa form of rhGAA was isolated from strain OXYY1589 as follows. After harvest, the broth was clarified using ceramic membranes (Pall Corporation). The product was concentrated via hollow fiber membranes with a molecular-weight-cut-off (MWCO) of 10 kD. AMS was added to a concentration of 1 M and the solute was heated to 30° C. prior to filtration. The filtrate was treated with *A. oryzae* alkaline protease recombinantly expressed in *Yarrowia lipolytica* (strain OXYY2184) and used after clarification of the fermentation broth without any further purification. A weight:weight ratio of 200:1 for total protein:protease and incubation for 16 h at 30° C. resulted in a full proteolysis to the 95 kDa product.

Analysis after further purification and after uncapping and demannosylation of the phosphorylated N-glycans revealed a 95 kDa GAA product (as observed on SDS-PAGE) with similar specific activity on PNPG as reported in Table 1.

Example 14

Identification of the Proteolytic Cleavage Site in rhGAA after Treatment with *Aspergillus oryzae* Alkaline Protease (ALP)

rhGAA was treated with the *Aspergillus oryzae* ALP and further purified as described in the above examples. To facilitate sequence analysis, the purified sample was treated with PNGaseF to deglycosylate the rhGAA as PNGase F deaminates the N-glycosylated asparagine residues in the sequence to aspartate.

To confirm the sequence of rhGAA, the deglycosylated protein was digested using trypsin following reduction of the disulfide bridges and alkylation of the cysteine residues. The resulting peptide mixture was subjected to LC-MS and MS/MS and the data were matched onto the gene-encoded protein sequence thereby determining identity. Accurate mass (<10 ppm) and fragmentation spectra were criteria used for absolute identification.

Nearly full sequence coverage was obtained from the peptide mixture (residues 23-60, 65-535, and 538-898) and the proteolytic cleavage site was determined to be between amino acids 60 and 65 (sequence numbering according to SEQ ID NO: 1). The gap in the rhGAA sequence between residues 60 and 65 could result from a proteolytic event before Gly62 and/or before Gly65. It is reported in literature that the alkaline protease from *Aspergillus oryzae* degrades the synthetic peptide Ileu-Gln-Asn-Cys-Pro-Leu-Gly-NH2 (SEQ ID NO:12) between Leu and Gly (see Nakadai et al., 1973, *Agr. Biol. Chem.*, 37, 2685-2694).

The proteolytic cleavage site determined in this experiment is in accordance with the proteolytic processing of GAA observed in the lysosomes. See, Moreland et al., 2005, *J. Biol. Chem.*, 280, 6780-6791, where for the 95 kDa polypeptide, the cleavage site was identified between amino acid 59 and amino acid 68 (sequence numbering according to SEQ ID NO: 1). The cleaved N-terminal peptide remains associated via an interchain disulfide bond.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A pharmaceutical composition comprising an isolated molecular complex having acid alpha glucosidase (GAA) activity and consisting of a GAA-derived protein consisting of two polypeptides, a first polypeptide having at least 85% sequence identity to amino acids 22 to 57 of SEQ ID NO: 1, and a second polypeptide having at least 85% sequence identity to amino acids 66-896 of SEQ ID NO: 1, with the proviso that the pharmaceutical composition does not include an isolated molecular complex having GAA activity and at least three or at least four polypeptides, wherein at least one of said two polypeptides includes a phosphorylated N-glycan such that said molecular complex has:

the substantial ability to bind to a mannose-6-phosphate receptor on a mammalian cell and consequently, the ability to be transported to the interior of the mammalian cell; and a pharmaceutically acceptable carrier.

2. The molecular complex of claim 1, wherein said mammalian cell is a human cell.

3. The pharmaceutical composition of claim 1, wherein:
at least one of said phosphorylated N-glycans is uncapped and demannosylated; or
at least 40% of the N-glycans are uncapped and demannosylated; or
at least 60% of the N-glycans are uncapped and demannosylated; or
at least 80% of the N-glycans are uncapped and demannosylated; or
at least 90% of the N-glycans are uncapped and demannosylated; or
said sequence identity for each polypeptide is at least 90%.

4. The pharmaceutical composition of claim 1, wherein:
said molecular complex is lyophilized; or
said molecular complex is lyophilized and said composition is packaged as a single use vial; or
said composition is formulated for intravenous or subcutaneous administration or for intravenous infusion.

5. A method of providing enzyme replacement therapy to a subject diagnosed with Pompe's disease, said method comprising administering said composition of claim 4, to a subject diagnosed with Pompe's disease.

6. The method of claim 5, wherein said subject is diagnosed with infantile onset Pompe's disease or with late onset Pompe's disease.

7. A method of transporting a molecular complex having GAA activity to the interior of a cell, said method comprising:

contacting a mammalian cell with an isolated molecular complex having acid alpha glucosidase (GAA) activity and consisting of a GAA-derived protein consisting of two polypeptides, a first polypeptide having at least 85% sequence identity to amino acids 22 to 57 of SEQ ID NO: 1, and a second polypeptide having at least 85% sequence identity to amino acids 66-896 of SEQ ID NO: 1, with the proviso that the mammalian cell is not in contact with an isolated molecular complex having GAA activity and having at least three or at least four polypeptides, wherein at least one of the two polypeptides includes a phosphorylated N-glycan such that said molecular complex has:

the substantial ability to bind to a mannose-6-phosphate receptor on a mammalian cell; and consequently, the ability to be transported to the interior of the mammalian cell.

8. The method of claim 7, wherein:
said mammalian cell is in vitro; or
said mammalian cell is in a mammalian subject; or
said mammalian cell is a human cell.

9. An isolated fungal cell comprising a nucleic acid encoding a GAA protein having at least 85% sequence identity to the GAA amino acid sequence set forth in SEQ ID NO:1 and a nucleic acid encoding an alkaline protease having at least 85% sequence identity to the amino acid sequence set forth in SEQ ID NO:8, wherein said fungal cell produces a molecular complex having GAA activity and comprising two polypeptides, each polypeptide having at least 85% sequence identity to a segment of the amino acid sequence set forth in SEQ ID NO: 1, each segment being derived by proteolysis of the amino acid sequence set forth in SEQ ID NO: 1 at one or more sites between amino acid 50 and amino acid 74 by said alkaline protease.

10. The fungal cell of claim 9, wherein
said fungal cell further comprises a nucleic acid encoding a mannosidase, said mannosidase being capable of (i)

hydrolyzing a mannose-1-phospho-6-mannose moiety to mannose-6-phosphate and (ii) hydrolyzing a terminal alpha-1,2 mannose, alpha-1,3 mannose and/or alpha-1,6 mannose linkage; or said fungal cell further comprises a nucleic acid encoding a mannosidase, said mannosidase being capable of hydrolyzing a mannose-1-phospho-6-mannose moiety to mannose-6-phosphate; or said fungal cell further comprises a nucleic acid encoding a mannosidase, said mannosidase being capable of hydrolyzing a terminal alpha-1,2 mannose, alpha-1,3 mannose and/or alpha-1,6 mannose linkage; or said fungal cell further comprises a nucleic acid encoding a mannosidase, said mannosidase being capable of (i) hydrolyzing a mannose-1-phospho-6-mannose moiety to mannose-6-phosphate and (ii) hydrolyzing a terminal alpha-1,2 mannose, alpha-1,3 mannose and/or alpha-1,6 mannose linkage and further comprises a nucleic acid encoding a polypeptide capable of promoting mannosyl phosphorylation; or said fungal cell further comprises a nucleic acid encoding a mannosidase, said mannosidase being capable of (i) hydrolyzing a mannose-1-phospho-6-mannose moiety to mannose-6-phosphate and (ii) hydrolyzing a terminal alpha-1,2 mannose, alpha-1,3 mannose and/or alpha-1,6 mannose linkage, and said fungal cell is genetically engineered to be deficient in OCH1 activity.

\* \* \* \* \*